United States Patent [19]

Funk

[11] 4,253,766

[45] Mar. 3, 1981

[54] OPTICAL GRAIN ANALYSIS INSTRUMENT

[75] Inventor: David B. Funk, Auburn, Ill.

[73] Assignee: Dickey-john Corporation, Auburn, Ill.

[21] Appl. No.: 935,635

[22] Filed: Aug. 21, 1978

Related U.S. Application Data

[63] Continuation-in-part of Ser. No. 833,451, Sep. 15, 1977, abandoned.

[51] Int. Cl.³ .............................................. G01J 3/50
[52] U.S. Cl. .................................. 356/418; 356/426; 356/446; 356/447; 364/526
[58] Field of Search ............... 356/300, 332, 418, 419, 356/426, 445–448, 244, 246; 364/498, 526, 556

[56] References Cited

U.S. PATENT DOCUMENTS

| | | | |
|---|---|---|---|
| 3,776,642 | 12/1973 | Anson et al. | 356/418 |
| 3,828,173 | 8/1974 | Knepler | 356/418 X |
| 3,860,344 | 1/1975 | Garfunkel | 356/418 X |
| 3,861,788 | 1/1975 | Webster | 356/418 X |
| 3,864,037 | 2/1975 | Johnson | 356/418 |
| 3,877,812 | 4/1975 | Thompson | 356/418 |
| 4,030,837 | 6/1977 | Kojima et al. | 356/445 |
| 4,040,747 | 8/1977 | Webster | 356/418 |
| 4,082,464 | 4/1978 | Johnson, Jr. | 356/418 |
| 4,149,805 | 4/1979 | Chew | 356/416 |

OTHER PUBLICATIONS

Kubik, Western Electric Technical Digest, No. 3, Jul. 1966, pp. 21 and 22.

Primary Examiner—F. L. Evans
Attorney, Agent, or Firm—Trexler, Wolters, Bushnell & Fosse, Ltd.

[57] ABSTRACT

An analysis instrument for measuring the quantity of a constituent present in a sample of a material comprises a housing having a sample receptacle mounted therein to receive a sample of the material. A filter assembly is mounted in the housing including a plurality of filter elements for passing a corresponding plurality of predetermined frequencies of radiant energy. A motor is provided for selectively providing relative movement between the sample receptacle and filter assembly so as to place individual ones of the filter elements into registry with the sample receptacle. A radiant energy source is mounted within the housing to direct radiant energy onto the surface of the sample through selected ones of the filter elements as each moves into registry therewith, to provide reflected radiant energy at the predetermined frequency of each of the selected filter elements. A sensor is mounted to receive the reflected radiant energy and provide electrical signals corresponding thereto. A second motor is provided for relative movement between the sample receptacle and the sensor so that the sensor receives reflected energy from a plurality of locations on the surface of the sample. Electrical circuits are provided for receiving the electrical signals from the sensor and providing a readout therefrom corresponding to the quantity of the constituent being measured.

34 Claims, 25 Drawing Figures

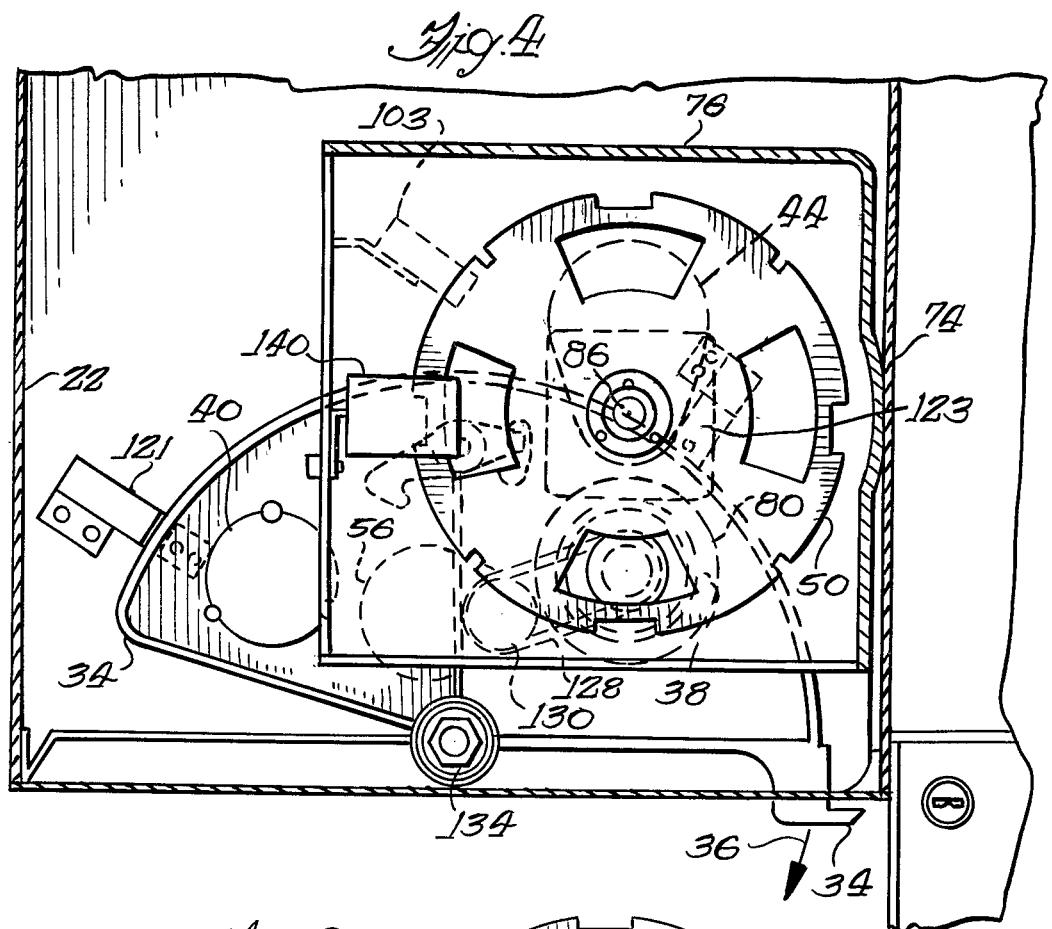
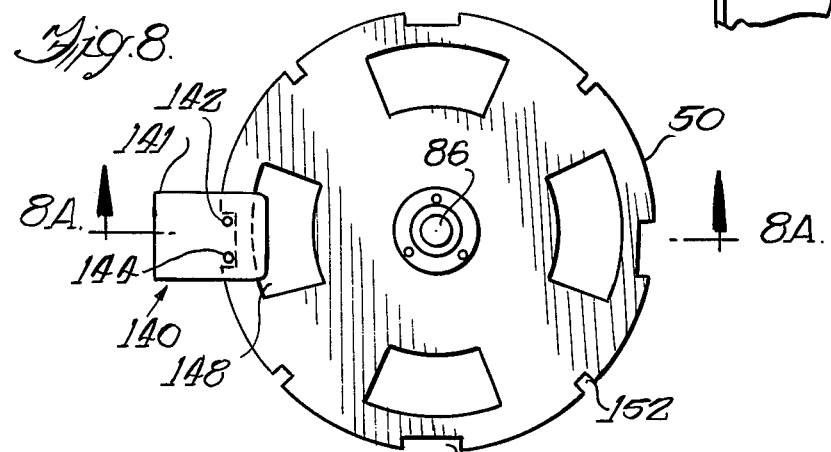
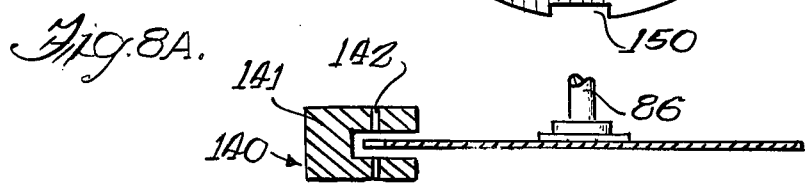

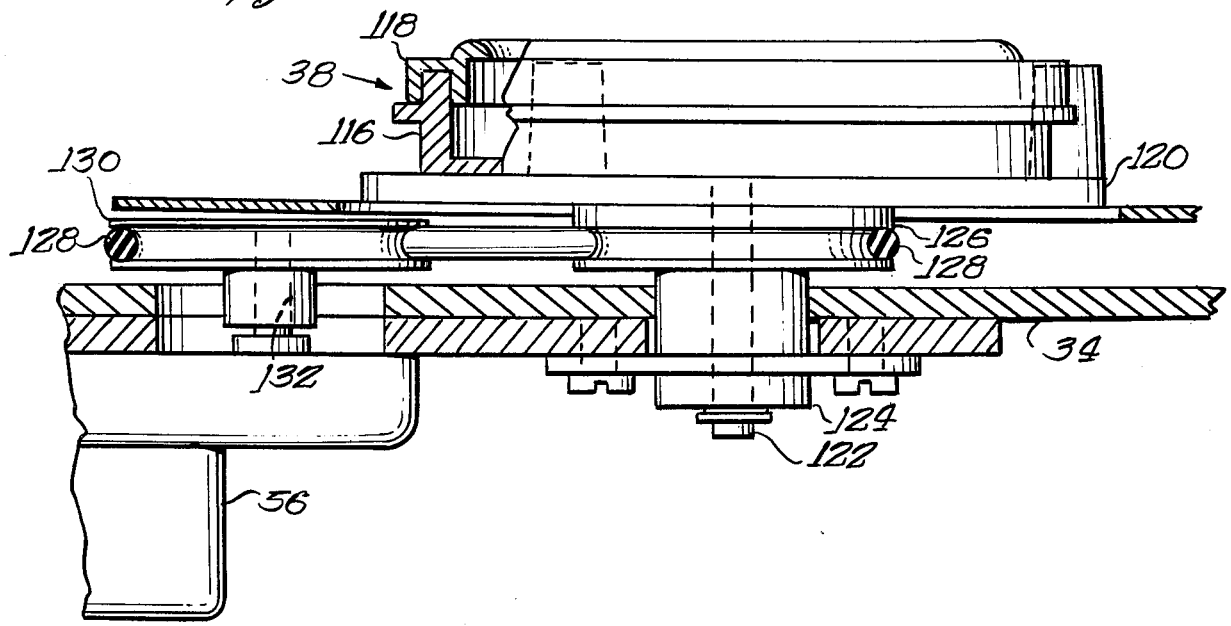
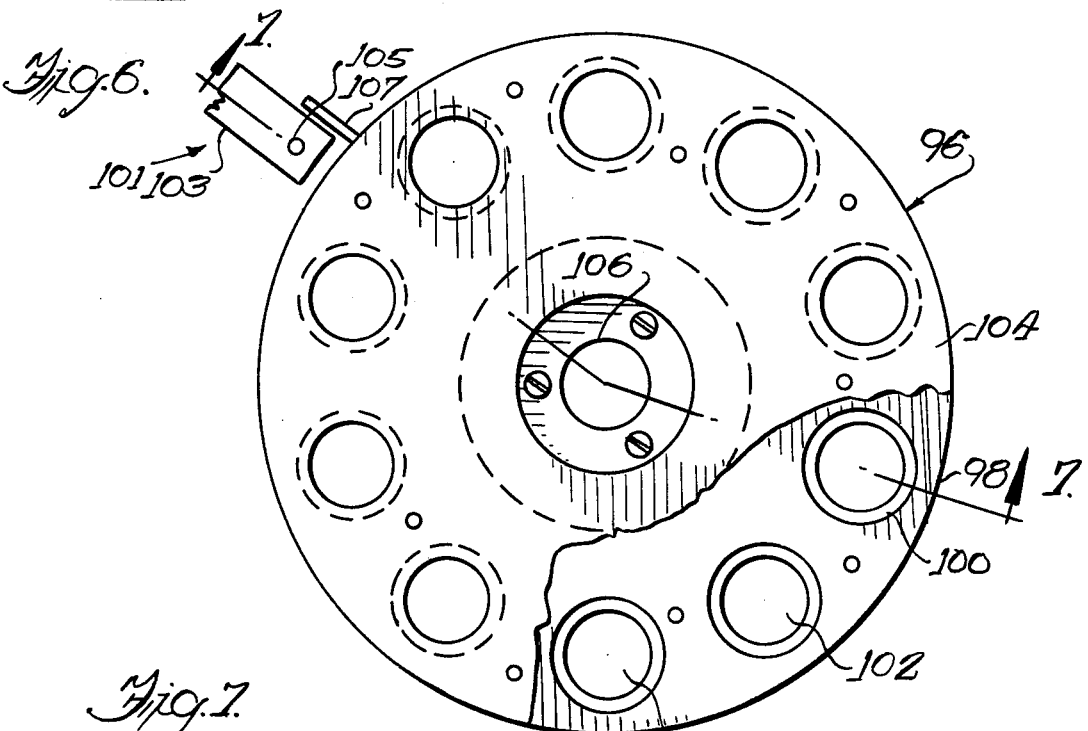
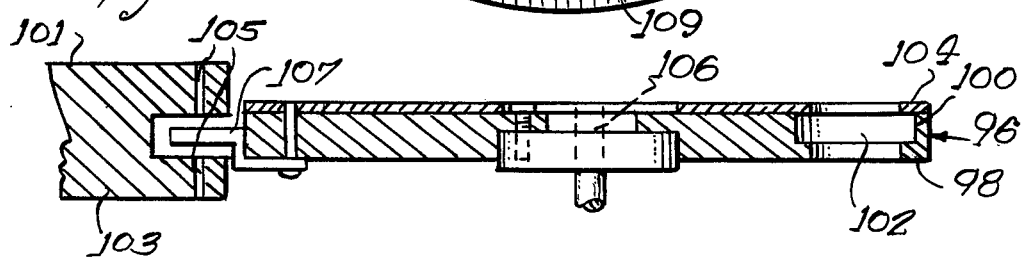

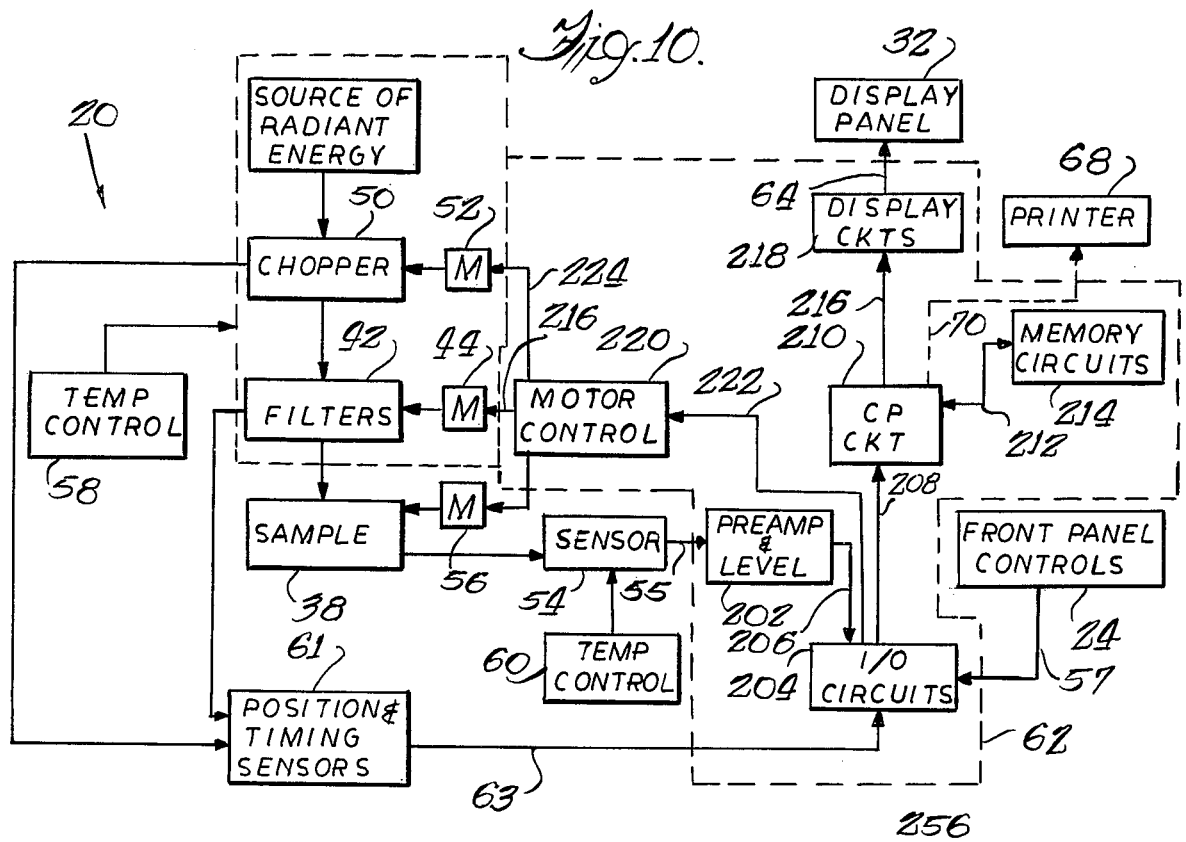
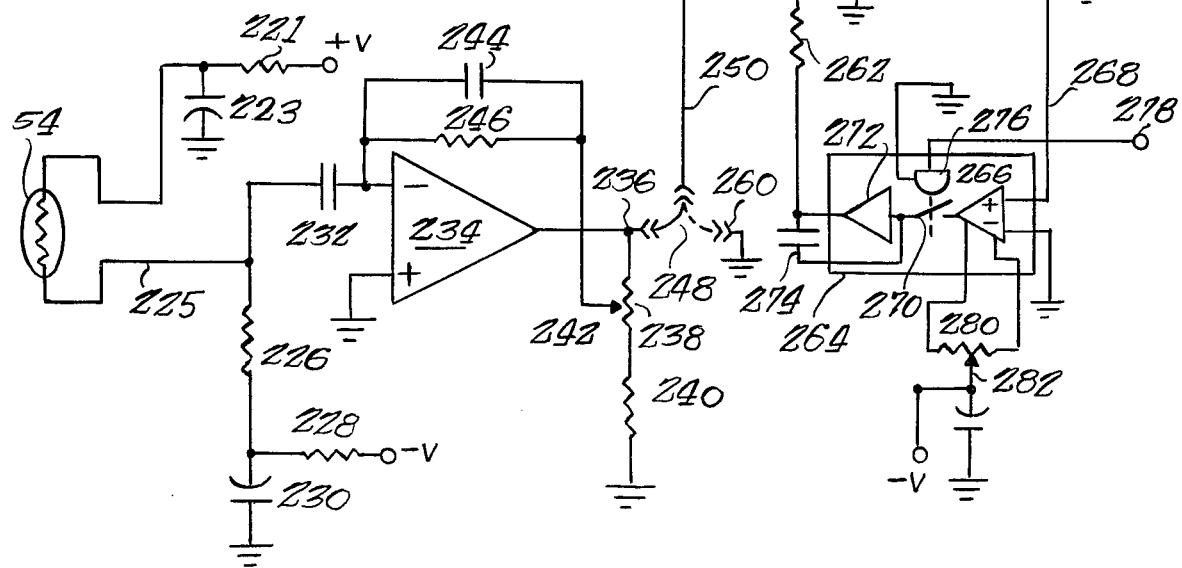

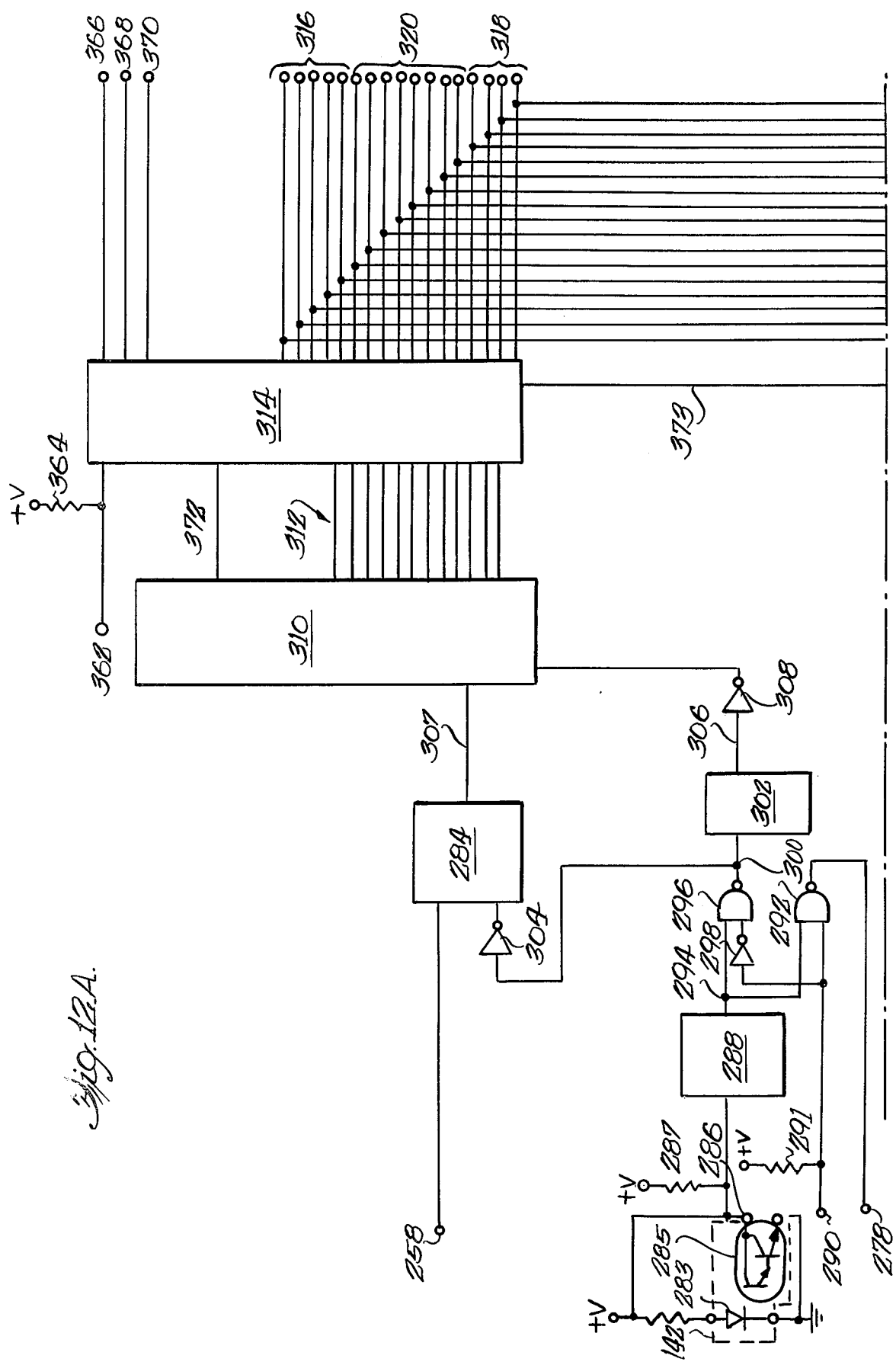

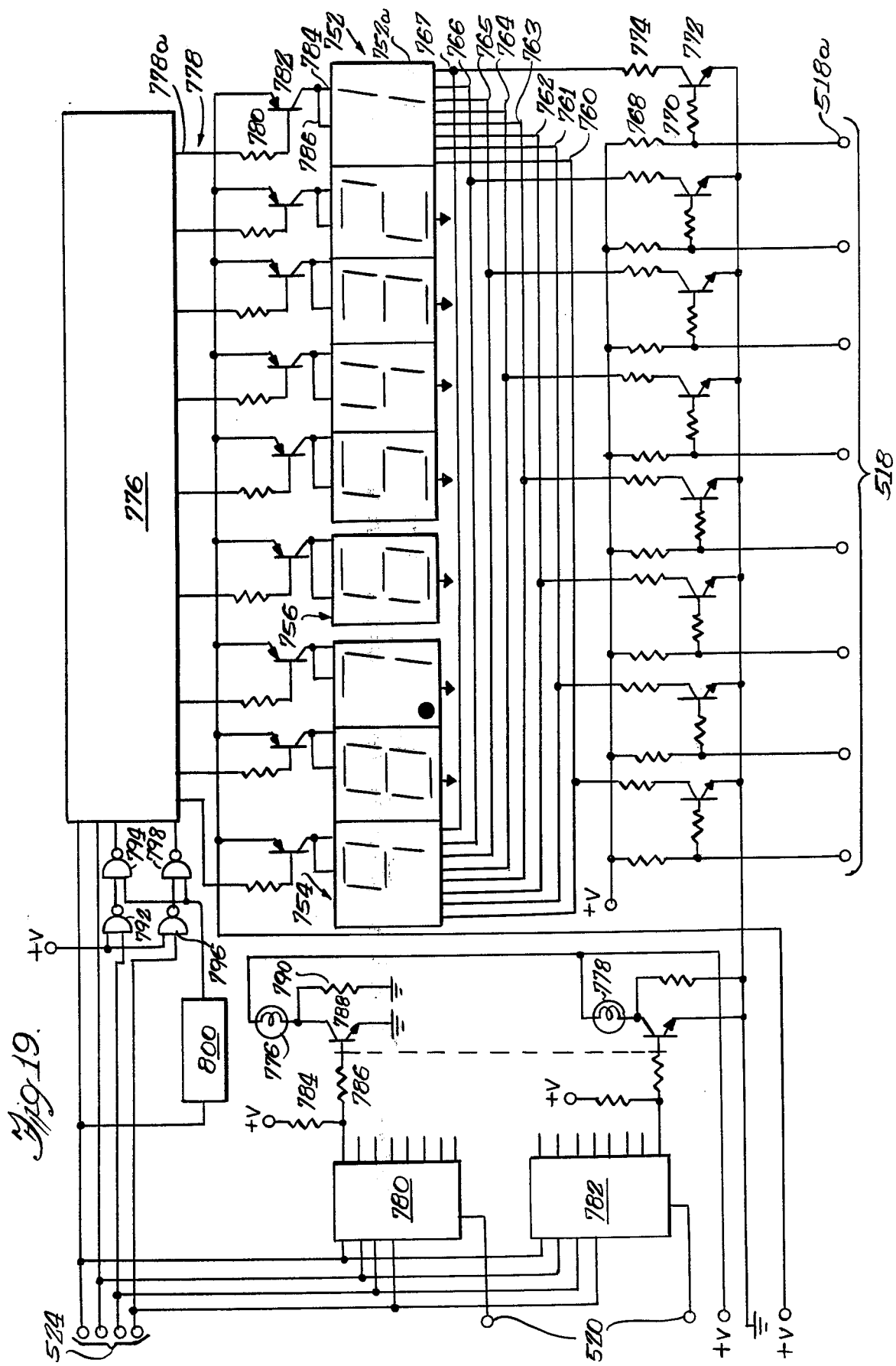

OPTICAL GRAIN ANALYSIS INSTRUMENT

This application is a continuation-in-part of application Ser. No. 833,451, filed Sept. 15, 1977, now abandoned.

BACKGROUND OF THE INVENTION

The present invention relates generally to an analysis instrument, and more particularly to an analysis instrument which is adapted to measure the quantities of specific constituents present in bulk commodities such as agricultural products, as for example, corn, soy beans and the like. Still more particularly, the present invention is directed to an improved analysis instrument for measuring and analyzing optical properties, as for example, optical density, of materials at various frequencies to determine the quantities of certain constituents present in the materials.

Traditional analytical and laboratory techniques for measuring the quantities of constituents present in various materials, as for example, the quantities of moisture, protein or oils present in various agricultural grain products, require the use of relatively complex equipment as well as the efforts of skilled chemists or other skilled technicians. Many users of agricultural products, however, are increasingly interested in obtaining such data as the percentages of moisture, protein and oil contained in these products. Specifically, the practice of selling wheat on the basis of a guaranteed protein content has become widespread. In order to remain competitive, the commodity handler must be able to rapidly and accurately sort grains and other products by their content of various constituents, when such data is specified by the users. Thus, there is a need for a versatile test instrument for rapidly determining the quantity of various constituents present in actual samples of various commodities. Such an instrument must be capable of reliably testing a relatively broad range of materials for a number of constituents, while being relatively easy to operate so that the operator thereof need not possess specialized skills or specific knowledge of the theory or function of the instrument.

An analysis of the optical densities of various materials as, for example, by non-destructive light transmittance or reflectance tests, is indicative of the content of various constituents present in the materials. For example, the amount of light reflected at certain frequencies from a sample of a farm grain is indicative of the content thereof of such constituents thereof as moisture, protein, and oil. The difference in optical density of the material as determined by the ratio of amount of light reflected therefrom to amount of light incident thereon measured at two different frequencies has been found to be a useful measurement in determining various constituent contents. Specifically, the constituent content of the material is a function of the difference in optical density so measured. If the intensity of incident light at both frequencies is held constant, then the difference in optical density may be determined from the difference in reflected light intensities at the two frequencies. Certain frequencies may be selected for their sensitivity to specific constituents and the optical densities at these various specific frequencies are interrelated, such that the content of a plurality of constituents may be determined by correlating measurements taken at frequencies selected for each.

Accordingly, it was necessary in prior art devices to have a large number of frequencies or wavelengths of infrared radiation made available via either a large array of filter elements for passing individual wavelengths from a fixed source or via relatively complex mechanical structures for rotating a number of fixed filters through a variety of angular positions with respect to a light source to obtain varying frequencies therefrom. It will be appreciated that the complexity of the mechanical parts required to handle either such a large number of filter elements or a relatively complex rotation and movement of filter elements, is cumbersome and difficult to manufacture and to properly install, giving rise to excessive expense and potential unreliability of the instrument. Also, prior instruments generally have been designed, constructed and calibrated so as to be capable of handling only a predetermined fixed number of grains and of obtaining readings therefrom representative of only a limited number of constitutents thereof, commonly being limited to percentage content of oil, water and protein. As a practical matter, therefore, it is not possible to expand the capabilities of such prior art instruments to perform measurements on different materials or to measure different constituents than those for which they are already designed. Further, prior art instruments are also subject to temperature variation. For example, changes in the temperature of the optical portions of the instruments, including the filters and the sensors, can cause difficulty in maintaining reliability in measurements performed over a range of temperatures.

OBJECTS AND SUMMARY OF THE INVENTION

Accordingly, it is a general object of the present invention to provide an analysis instrument capable of measuring the content of a constituent in a material quickly and reliably without requiring particular technical skills or specialized knowledge of the theory or operation thereof.

It is another general object of the present invention to provide an analysis instrument having the versatility to perform measurements of a large number of constituents in a correspondingly large number of materials, including agricultural products such as farm grains and the like.

A more specific object of the present invention is to provide an analysis instrument for measuring constituent contents of materials in accordance with the optical density thereof, wherein the optical portions of the instrument are substantially less cumbersome and less complicated than prior art instruments, whereby the instrument is more reliable as well as simpler and less costly to manufacture.

Another object of the present invention is to provide a grain analysis instrument, in accordance with the foregoing objects, which is capable of being relatively easily adapted to analyze different constituents and/or materials than those for which it is initially set up and for measuring constituent contents of materials over different ranges than those for which it is initially set up.

Yet another object of the present invention is to provide an analysis instrument, in accordance with the foregoing objects, which is capable of measuring constituent contents of materials according to presently accepted standards and formulas for obtaining such measurements from optical density measurements and further capable of being readily and easily modified to perform such measurements according to new or different standards or formulas which may hereafter be developed.

It is a further object of the present invention to provide an analysis instrument, in accordance with the foregoing objects, which is capable of prompting the operator with instructive messages and to warn of improper use or malfunctions of the instrument.

A still further object of the present invention is to provide an analysis instrument, in accordance with the foregoing objects, which is adapted to minimize the effects of temperature variation of the optical portions thereof in order to insure reliability of measurements over a relatively broad range of temperatures.

A further object of the present invention is to provide an analysis instrument, in accordance with the foregoing objects, which comprises a single unit for a size suitable for table top operation.

Briefly, the analysis instrument of the present invention is provided with a sample receptacle mounted in a housing to receive a sample of a material to be analyzed. Filter means are mounted in the housing for passing a plurality of discrete predetermined frequencies of radiant energy and means are provided for obtaining relative movement between the sample receptacle on the filter means to selectively place the filter means in registry with the sample receptacle. A radiant energy source is mounted within the housing for directing radiant energy through the filter means in registry with the sample and onto the surface of the sample to provide reflected radiant energy at selected ones of the predetermined frequencies of the filter means. A sensor is mounted within the housing to receive the reflected radiant energy and provide a plurality of electrical signals corresponding thereto. Means are also provided for a relative movement between the sample receptacle and the sensor so that the reflected radiant energy may be received by the sensor means from a plurality of locations upon the surface of the sample. Circuit means are provided for receiving the electrical signals from the sensor means and providing an indication therefrom corresponding to the quantity of selected constituents present in the sample. The circuit means further include control means for automatically controlling the sequence of measurement taking and indication producing in accordance with predetermined instructions stored therein and with operator instructions via a control panel.

Other features, objects and advantages of the present invention will be more readily appreciated upon consideration of the following detailed description together with the accompanying drawings wherein like reference numerals are used throughout to designate like elements and components.

BRIEF DESCRIPTION OF THE DRAWINGS

FIG. 4 is a partially cut away view taken generally along the lines 4—4 of FIG. 3;

FIG. 5 is an enlarged view of a portion of FIG. 3;

FIG. 6 is an enlarged view of a filter wheel assembly portion of the instrument of FIGS. 3 and 4;

FIG. 7 is a view taken generally along the line 7—7 of FIG. 6;

FIG. 8 is an enlarged view of the chopper disc portion of the instrument of FIGS. 1-4;

FIG. 8A is a view taken generally along the line 8A—8A of FIG. 8;

FIG. 10 is a simplified block diagram of the overall arrangement of the analysis instrument of the present invention, including the electrical circuit components thereof;

FIG. 11 is a detailed schematic diagram of the pre-amp and level circuits of the block diagram of FIG. 10;

FIGS. 12A and 12B are a detailed schematic diagram of the input/output circuit of FIG. 10;

FIG. 19 is a schematic diagram of the display circuits of FIG. 10;

DETAILED DESCRIPTION

Figure 1:
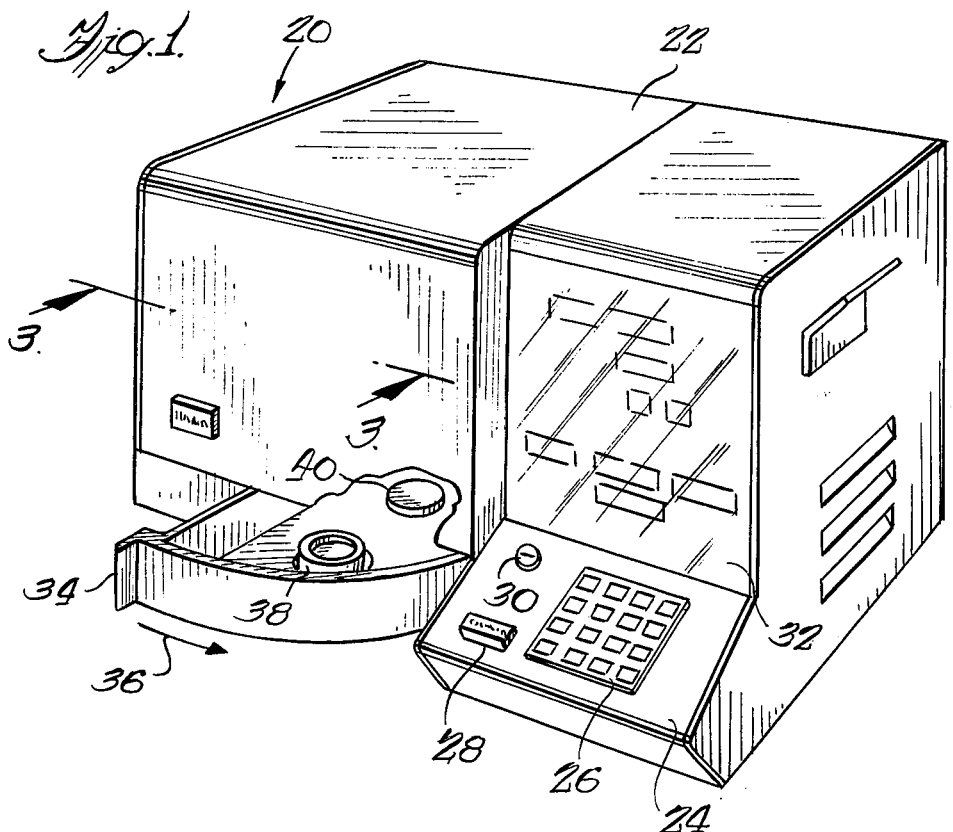
FIG. 1 is a perspective view of an analysis instrument incorporating features of the present invention.

Referring now to FIG. 1, an analysis instrument 20, according to the present invention, comprises a single unit of a size suitable for table-top operation, contained within an exterior housing 22. The instrument 20 is adapted to be operated via a control panel 24 including a keyboard 26 comprising a four-by-four array of pushbuttons, a step switch 28 and a key switch 30. The function and operation of the elements of the control panel 24 will be explained in detail hereinbelow. The analysis instrument 20 also includes a display panel 32 mounted directly above the control panel 24, for providing indications of the operations being performed by the instrument including visual readouts of quantities being measured thereby. A drawer 34 for receiving a sample to be analyzed is provided which drawer is shown in FIG. 1 in the open position and is selectively closable in the direction indicated by the arrow 36. A sample receptacle 38 is provided within the drawer 34 to receive a sample of the material. A reference standard 40 is also mounted within the drawer 34 for calibration purposes and comprises a disc of material of known properties and generally of the same dimensions as the sample receptacle 38. The sample receptacle 38 and reference standard disc 40 are so positioned within the drawer 34 that the sample receptacle 38 is positioned for analysis when the drawer is fully closed, while the reference standard is so positioned when the drawer is fully opened.

Figure 2:
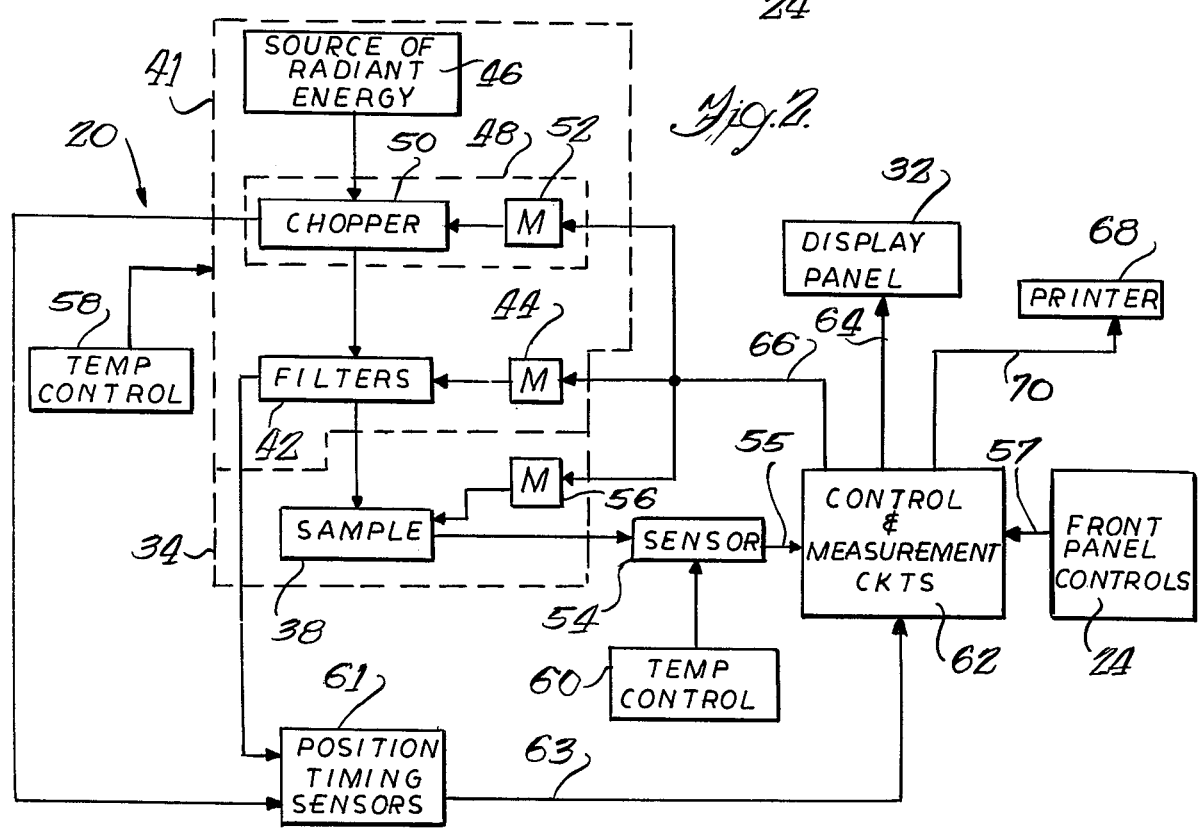
FIG. 2 is a simplified block diagram showing the overall arrangement of the analysis instrument of the present invention.

Referring now to FIG. 2, a simplified block diagram illustrates the overall arrangement of the various elements of the analysis instrument 20 of FIG. 1. The housing 22 has been omitted in FIG. 2 to facilitate clarity of the illustration. The sample receptacle 38 is mounted as described above to receive a sample of the material to be analyzed. An optics module 41 is mounted above the sample receptacle 38. The optics module 41 includes filter means 42 for passing a plurality of discrete predetermined frequencies of radiant energy and means such as motor 44 are provided for causing relative movement between the sample receptacle 38 and the filter means 42 to selectively place the filter means 42 in registry with the sample receptacle 38. The optics module 41 also includes a source of radiant energy 46, mounted to direct radiant energy through the filter means and onto the surface of the sample to provide reflected radiant energy signals at selected ones of the predetermined frequencies provided via the filter means 42. The optics module 41 further includes chopper means 48, provided between the radiant energy source 46 and the filter means 42, for providing radiant energy at a plurality of discrete intervals from the source 46 to the sample receptacle 38 via the filter means 42. The chopper means 48 preferably comprise a chopper disc 50 to be described in detail hereinbelow and means such as a motor 52 for driving the chopper disc 50 to provide the aforementioned discrete intervals. Sensor means 54 are provided for receiving the reflected radiant energy from the surface of the sample in the receptacle 38 and providing electrical signals corresponding thereto. Means such as a motor 56 is provided for causing relative rotation between the sample receptacle 38 and the sensor 54 so that the reflected radiant energy is received by the sensor means from a plurality of locations on the surface of the sample contained in the sample receptacle 38. Temperature control means 58 are provided in the optics module 41 for substantially eliminating any temperature variation therein from a predetermined temperature. Similarly, a second temperature control means 60 is provided for the sensor means 54 to substantially eliminate any variation in temperature thereof from a predetermined temperature. Position and timing sensors 61, to be described in detail below, are provided for sensing the relative position and rotation of the filter means 42 and chopper disc 50 respectively and producing suitable signals corresponding thereto.

Control and measurement circuits 62, to be described in detail hereinbelow, receive the electrical signals from the position and timing sensors 61 via a line 63 and from the sensor means 54 via a line 55 and, in response to operator instructions via the line 57 from the keyboard 26 and other front panel controls 24 connected thereto and provide appropriate signals via a line 64 to the front panel display 32, for providing a visual indication of the various functions and measurements of the instrument, as will be described in detail hereinbelow. The control and measurement circuits 62 are also connected via a line 66 to provide suitable control signals for the operation of the motors 44, 52 and 56. A printer 68, not part of the analysis instrument 20, may also be optionally connected via a line 70 to the control and measurement circuits 62, which are adapted to provide suitable signals via the line 70 to the printer for providing hard copy records of the measurements made by the analysis instrument 20.

Figure 3:
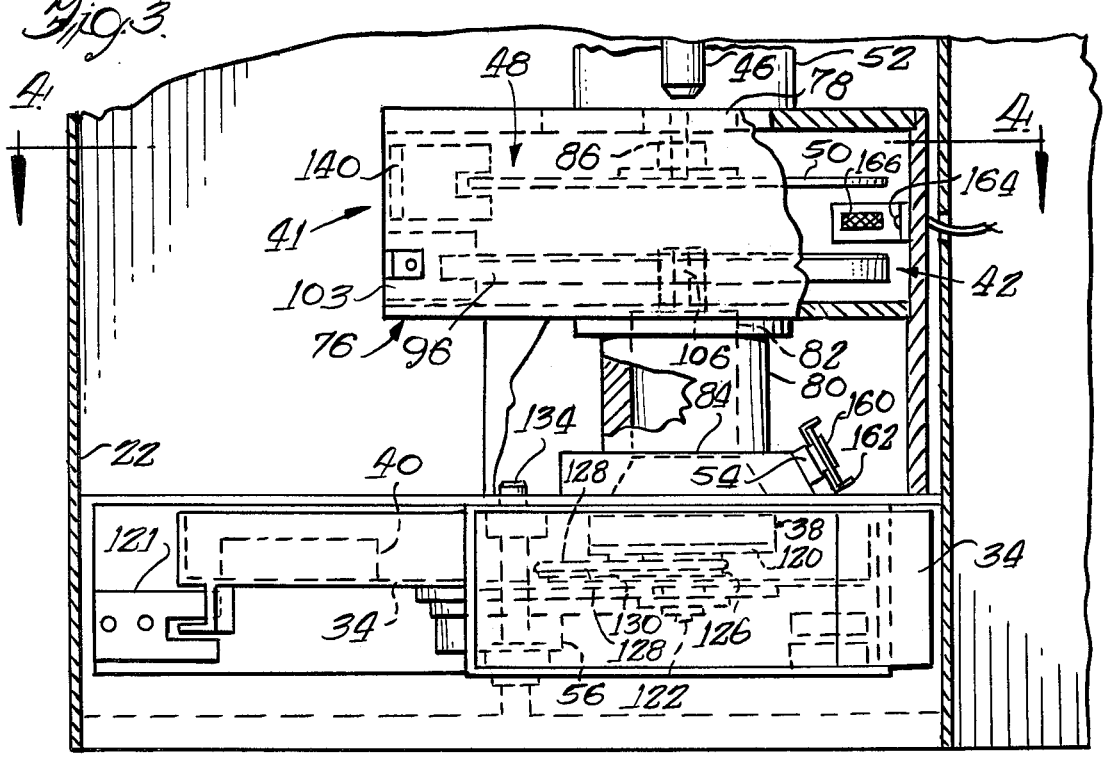
FIG. 3 is an enlarged view, partially cut away, of a portion of the analysis instrument of FIG. 1, taken generally along the line 3—3 of FIG. 1.

Referring now to FIGS. 3 and 4, portions of the interior arrangement of the analysis instrument 20 are illustrated. The radiant energy source 46 preferably comprises a source of infrared radiant energy such as a quartz-iodide or similar type lamp connected to a suitable power source (not shown). The optics module 41 includes a housing 76 for excluding extraneous light radiation from the exterior thereof. Infrared source 46 is positioned in registry with an opening 78 provided therefore in the housing 76. A baffle 80, provided at the opposite end of housing 76 from the infrared source 46, is generally cylindrical in shape and includes open ends 82 and 84 to allow the passage of radiation from the optics module 41 therethrough while excluding any extraneous light radiation from other sources. The sensor 54 is mounted in a side wall of the baffle 80, at a suitable angle for sensing reflected radiant energy from the surface of a sample contained in the sample receptacle 38. Chopper means 48 is included in the optics module and comprises the chopper disc 50 which is mounted upon a drive shaft 86 of the motor 52 for rotation in unison therewith. In a preferred embodiment, the motor 52 rotates the chopper disc at a speed of substantially 1800 rpm.

The filter means 42 comprises a filter disc assembly 96 of substantially the same diameter as the chopper disc 50. As best seen in FIGS. 6 and 7, the filter disc assembly 96 comprises a disc 98 having a plurality of openings 100 disposed circumferentially about a common radius thereof. The openings 100 are generally cylindrical in shape and accommodate a corresponding plurality of filter elements 102, each of which is selected to pass a predetermined frequency of radiant energy therethrough. A protective cover disc 104 is provided of substantially the same diameter as the disc 98 and having a corresponding plurality of openings formed therein to allow the passage of radiant energy through the filter elements 102. The filter disc assembly 96 is mounted upon a drive shaft 106 of the motor 44 for rotation in unison therewith. The motor 44 is preferably a stepping motor, for rotating the filter disc 98 in discrete steps to sequentially bring each of the filter elements 102 into registry with the sample for a fixed increment of time. In a preferred embodiment, the motor 44 is actuated by suitable circuits, described below, to step the filter elements 102 at a rate of substantially one per second, so that each filter element 102 is in registry with the sample for substantially one second. It will be noted that any number of filter elements 102 may be employed in the filter disc assembly 96 in accordance with the present invention. However, 10 filter elements 102 are illustrated in the preferred embodiment of the present invention.

A portion of the position and timing sensor 61 of FIG. 2, associated with the filter disc assembly 96, includes a sensor assembly 101, best seen in FIGS. 6 and 7, comprising a generally U-shaped bracket 103, mounted adjacent the outer periphery of the filter disc 98. The bracket 103 contains a sensor element 105, to be described in detail hereinbelow. The filter disc assembly 96 includes a radially extending flange or finger 107 of substantially the same width as the amount the disc 96 is advanced by each step of the motor 44. Thus, the passage of the finger or flange 107 through the sensor assembly 101, and particularly past the sensor element 105 thereof, actuates the sensor element 105 for providing a suitable indication of the relative position of the filter disc 98. For example, when the filter element 109 is in registry with the sample receptacle 38, the finger 107 will be in registry with the sensor element 105, thereby providing an indication of the position of the filter element 109, which may be arbitrarily named filter element no. 1, and taken as a start and/or end position for the measurements to be made by the instrument. The sensor element 105 preferably comprises a light emitting diode mounted in one arm of the U-shaped bracket 103 and a photoresponsive transistor mounted in the opposite arm thereof. Thus, the flange or finger 107 actuates the sensor element 105 by cutting off the light from the light emitting diode to the photo-transistor, as it passes through the U-shaped bracket 103.

The sample drawer 34 holds the sample receptacle 38 and the reference standard disc 40 as described above. Suitable sensors 121 and 123 are provided adjacent the drawer 34 to produce signals indicative of the position of the drawer, fully opened or fully closed, respectively. The sample receptacle 38, as best seen in FIG. 5, comprises a generally cylindrical cup member 116 to receive a sample of the material to be analyzed, and a cover member 118 constructed of a transparent material such as glass which is adapted to fit tightly over the sample receiving cup 116 to provide an enclosure for the sample material introduced into the sample receptacle 38. The sample receptacle 38 is mounted upon a generally circular platform 120, which is mounted upon a shaft 122 for rotation in unison therewith. It will be noted that the sample receptacle 38 is selectively mountable on the platform 120 for rotation thereon either about the central axis of the sample receptacle or somewhat off-axis, for presenting either a circular or an annular section of the sample surface to the sensor 54. The shaft 122 is mounted for rotation within a suitable bearing member 124 mounted on the bottom portion of the sample drawer 34. The shaft 122 is driven by a pulley 126 mounted thereon which is in turn driven by a belt 128 attached thereto. The belt 128 is also mounted at its opposite end on a similar pulley 130 which is in turn mounted to rotate in unison with a shaft 132 of the motor 56. The motor 56 is mounted upon the underside of the sample drawer 34. As best seen in FIG. 3, the entire sample drawer 34 is mounted upon a shaft 134 to be selectively rotated thereabout for opening and closing the sample drawer 34 generally along the direction indicated by the arrows 36 of FIGS. 1 and 4.

The chopper disc 50, as best seen in FIGS. 8 and 8A, comprises a disc of substantially the same diameter as the filter disc 98 of FIGS. 6 and 7. A further portion of the position and timing sensor 61 of FIG. 2 comprises a sensor assembly 140 including a generally U-shaped bracket 141 positioned overlapping an edge of the chopper disc 50 and having a pair of sensor elements 142, 144 mounted thereon. It will be noted that the chopper disc has four generally arcuate slots 148 disposed about a common radius thereof and situated generally in alignment with the common radius of the filter elements 102 of the filter disc 96 therebelow. Four notches 150 are disposed about the outer circumference of the disc 50, the centers of the radial dimensions thereof being generally in alignment with the corresponding radial centers four arcuate slots 148 respectively. The notches 150 define radially extending openings in the circumference of the chopper disc 50 generally of the same dimension as the dimension between the outer edges of the sensor elements 142 and 144. Four smaller notches, designated generally 152, are similarly provided in the outer circumference of the disc 50 and spaced substantially half way between the adjacent notches 150 thereof. The notches 152 have a radial dimension substantially smaller than that of the notches 150. It will be appreciated that as the disc 50 rotates, the notches 150 and 152 will sequentially come into registry with the sensor assembly 140 and, in particular, the sensor elements 142 and 144 thereof, whereby corresponding signals are produced by the sensor elements 142 and 144 in response thereto. When one of the notches 150 is in registry with both sensor elements 142 and 144, both sensor elements 142 and 144 simultaneously produce a corresponding signal. It will be appreciated that as the notches 150 pass through the sensor assembly 140, first one, then both, then the other of the sensor elements will be activated thereby in sequence. Similarly, when one of the slots 152 moves into registry with the sensor assembly 140, the smaller width of the notch 152 is such that first one and then the other of the sensor elements 142 and 144 will produce a signal consecutively in response thereto. Thus, different signal conditions are provided by the sensor assembly 140 in conjunction with the slots 150 and 152: no signal, a signal from one, and a signal from both of the sensor elements 142 and 144. These signals provide suitable indication to the instrument of the relative position and movement or timing of the chopper disc 50. It will be appreciated from the foregoing description of the filter disc assembly 96 and chopper disc 50 which are mounted substantially concentrically and have substantially the same diameters, that the four slots 148 of the chopper disc are adapted to sequentially pass over a filter element 102 of the filter disc 96 which is in registry with the sample cup 38 therebelow, resulting in alternating passage and blocking of the radiation from the source of radiant energy 46 positioned thereabove. Thus, as the filter disc 98 holds each filter element in place for substantially one second, and the chopper disc rotates at substantially 1800 rpm, the slots 148 thereof produce substantially 120 periods of illumination per filter element, during which measurements of the sample are taken via the sensor 54. The signals produced by the sensor elements 142 and 144 in response to the passage of the slots 150 and 152 through the sensor assembly 140, correspond generally to periods of passage and cutting off of the source of radiant energy, respectively, by the chopper disc 50. Further, as the notches 150 are of a radial dimension less than and substantially on-center with the arcuate slots 148, the signals provided thereby will correspond substantially to the center portions of the slots 148 being in registry with the radiant energy source 46 and the particular filter element 102 which is in registry with the sample receptacle 38. The sensor elements 142 and 144 preferably comprise a pair of light emitting diodes attached to one arm of the U-shaped bracket 141, and a corresponding pair of photoresponsive transistors attached to the other arm thereof. Thus, the chopper disc 50 alternatively cuts off and passes the light from the light emitting diodes to the photoresponsive transistors as the notches 150 and 152 pass through the bracket 141.

Referring again to FIG. 3, a temperature sensor 160 is provided on the radiant energy sensor 54 and similarly, a temperature sensor 164 is provided within the housing 76. A thermal electric cooler 162 is provided adjacent the temperature sensor 160 and also mounted upon the radiant energy sensor 54. Similarly, an electric heating element 166 is mounted within the housing 76 adjacent the temperature sensor 164. The cooling element 162 and heating element 166 are adapted to provide heating and cooling in response to the temperature signals from the respective temperature sensing elements 160 and 164, to hold the radiant energy sensor 54 and the housing 76 substantially at predetermined temperatures. Thus, the radiant energy sensing element 54 and the housing 76 of the optics module 41 are held at a substantially constant temperature to avoid any loss of reliability in the measurements made by the analysis instrument due to temperature variations therein. Suitable circuit elements for accomplishing this temperature control are described in detail hereinbelow.

Figure 9:
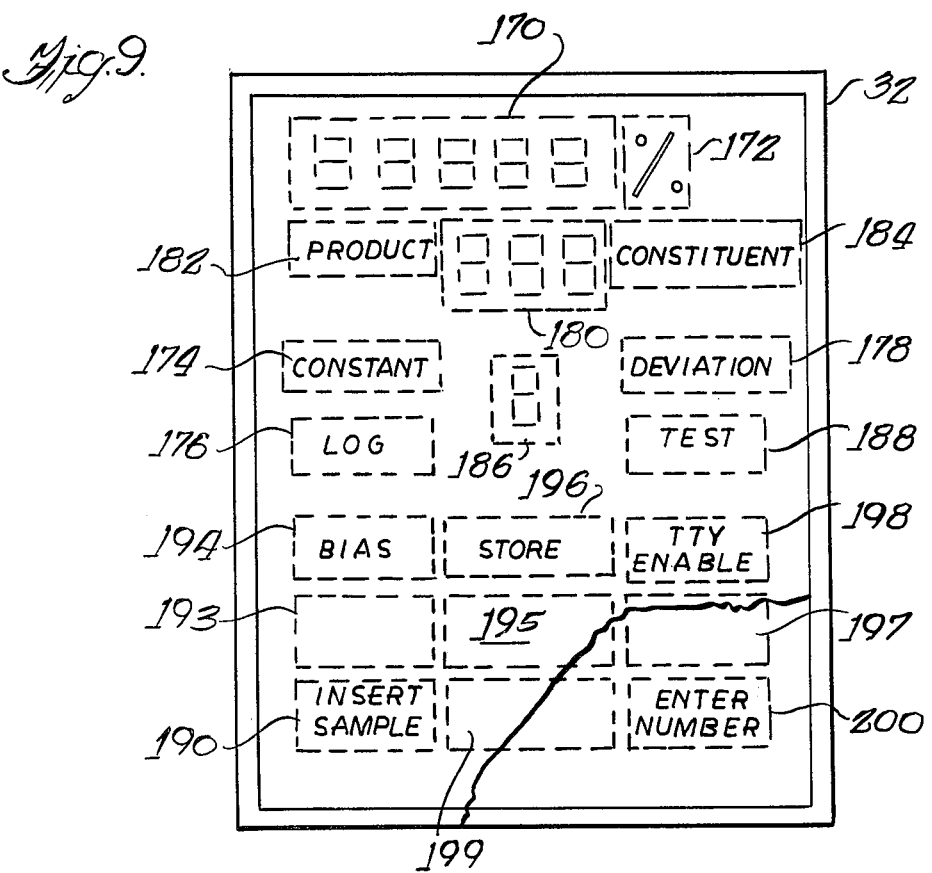
FIG. 9 is an enlarged view of the display panel portion of the instrument panel of FIG. 1.

Referring now to FIG. 9, the display panel 32 of FIG. 1 is illustrated in greater detail. A first line 170 of seven segment numerical displays is provided for giving a visual indication readout of the values of measurements made by the instrument, or may be alternately used, as selected by the operator via the keyboard 26, to give a visual indication of constant values stored in the instrument. A back lighted message portion 172 is selectively lighted to give an indication that the digits being displayed on the line 170 indicate percentages of constituents as measured by the instrument. Similarly, back lighted messages 174, 176 and 178 are selectively lighted to give an indication that the digits displayed on the line 170 represent constant values stored in the instrument, log values of measurements made by the instrument, or a deviation or error indication, respectively. A second line 180 of seven segment numerical displays provide a visual indication corresponding to the constituent whose value is currently being displayed on the line 170 and to the material currently being analyzed by the instrument. Black lighted messages 182 and 184 are selectively lighted to give an indication that the numbers appearing on the line 180 identify a constituent being displayed on the line 170, the product currently being tested by the instrument, or both, respectively. A final seven segment numerical display 186 is used in conjunction with the back lighted messages 174, 176 and 178 to display a number corresponding to the respective log, constant, deviation or error being displayed on the line 170. Other back lighted messages include a test message 188 to indicate that the instrument is in the process of testing a sample of material introduced therein, and an insert sample message 190 to indicate to the operator that the instrument is ready to begin measurements on a new sample. Back lighted messages further include a bias message 194, a store message 196, a teletype (TTY) enable message 198 and an enter number message 200. The foregoing is intended to give a general description of the appearance of the display panel 32 of the analysis instrument. A more complete description of the functioning thereof is given in conjunction with the description of the display circuits, hereinbelow.

Referring now to FIG. 10, a block diagram, similar to FIG. 2, illustrates the overall arrangement of the analysis instrument of the present invention. It will be noted that a number of the elements of FIG. 2 are repeated in FIG. 10 to clarify the illustration and are indicated by the same numbers as in FIG. 2. The control and measurement circuits 62 of FIG. 2 have been sub-divided into a number of functional blocks, to facilitate the description of the electronic circuits included in the analysis instrument, according to the present invention.

The control and measurement circuits 62 include a pre-amp and level circuit 202 for receiving signals from the sensor 54 via the line 55. An input/output circuit 204 is provided for receiving the signals from the pre-amp and level circuits 202 via a line 206, and also receives signals from the front panel controls 24 via the line 57. The input/output circuit 204 is also connected via a line 208 to a central processing (CP) circuit 210. The central processing (CP) circuit 210 is connected via a line 216 to display circuits 218 which are connected to the display panel 32 via the line 64, and via the line 70 to the printer 68. A motor control circuit 220 is connected via a line 222 to the input/output circuit 204, and via lines 224, 226 and 228 to the motors 44, 52 and 56, respectively.

The foregoing circuits will be described in detail hereinbelow. However, it is advantageous here to give a general description of the operation of the circuits thus far described in block diagramatic form. As described above, the sensor 54 receives reflected radiant energy from the surface of the sample contained in the sample receptacle 38 and produces electrical signals corresponding thereto, which electrical signals are a function of the optical density of the material being tested. The optical density of the material bears a known proportion to the quantity of constituents therein which it is desired to measure. The pre-amp and level circuits 202 receive these electrical signals from the sensor 54 via the line 55 and put the signals in a suitable form to be output on the line 206 to the input/output circuits 204. The input/output circuits 204 also receive signals from the position and timing sensors 61 via the line 63, corresponding to the respective position of the filter 42 and the chopper 50. An input on the line 57 to the input/output circuit 204 carries signals corresponding to the operator instructions via the front panel controls 24 including the identity of the material to be tested and the constituent contents thereof to be measured and displayed or printed out. The input/output circuits 204 put the above signals into suitable form to be transferred via the line 208 to the central processing (CP) circuit 210. The CP circuit 210 includes circuits adapted to obtain the constituent values for the material being tested in accordance with the foregoing received signals. As explained above, a plurality of measurements at different frequencies are obtained from the sample material via the sensor 54. Therefore, the central processing (CP) circuit 210 includes memory circuits, described hereinbelow suitable to store the measurements obtained until all the measurements have been completed, at which time the CP circuit 210 is adapted to perform the necessary operations to derive and display the constituent values called for by the operator from the measurements thus stored. To obtain the constituent values of the material being tested from the measurements recorded, the central processing circuit 210 is adapted to perform all the necessary computations. The computations performed include the application to the measurements of a plurality of empirically determined constants for each material and for each constituent thereof to be measured. Thus, memory circuits 214 are also provided to store the necessary constants and produce the constants via the line 212 as called for by the CP circuit 210. The central processing circuit 210 is also adapted to automatically control the sequence of measurement taking and indication producing of the instrument in accordance with initiation thereof via the front panel controls 24 and in accordance with a plurality of predetermined instructions stored in suitable memory devices which comprise a part of the memory circuits 214 and the input/output circuits 204.

Referring now to FIG. 11, the pre-amp and level circuits 202 of FIG. 10 are illustrated in detail. The sensor 54 preferably comprises an infrared sensitive photo-resistor which is connected via a resistor 221 to a positive DC voltage supply. The junction of the resistor 223 with the photocell 54 is connected via a suitable capacitor 221 to ground. The opposite end of the photocell 54 is connected via a line 225 in series with resistors 226 and 228 to a negative DC voltage supply. The junction of resistors 226 and 228 is connected via a suitable capacitor 230 to ground. The line 225 is also connected to a capacitor 232 whose opposite end is connected to the inverting input of an operational amplifier 234. The operational amplifier 234 has its non-inverting input connected to ground and has its output at a terminal 236 connected via a variable resistor 238 in series with a fixed resistor 240 to ground. A wiper arm 242 on the variable resistor 238 is connected via the parallel combination of a capacitor 244 and a resistor 246 to the inverting input of the operational amplifier 234. Thus, the input signal to the operational amplifier 234 is dependent upon the value of the photo-resistor 54 which is in turn dependent upon the intensity of the reflected radiant energy from the sample. The wiper arm 242 of the variable resistor 238 is adjusted to set the gain of the operational amplifier 234 to provide a suitable signal at the output 236 thereof for the following circuits. It will be noted that the operational amplifier 234 and the associated circuitry described above are selected for low input impedance and low noise to improve the stability of the output signal thereof in response to the signal input from the sensor 54, especially with regard to temperature variations.

The output terminal 236 of the operational amplifier 234 is connected via a connector 248 to a line 250 which is connected via a resistor 252 to the inverting input of an operational amplifier 254. The operational amplifier 254 has its non-inverting input connected to ground and has a feedback resistor 256 connected between its output 258 and its inverting input. It will be noted that the connector 248 may be selectively removed from the terminal 236 and connected to ground at a terminal 260, for grounding the inverting input of the operational amplifier 254, in order to calibrate the following circuit at zero input. The operational amplifier 254 serves as a ground referencing circuit for the input signal on line 250 thereto, resulting in the output signal on line 258 being referenced against ground to form a series of positive going pulses as opposed to the positive and negative going signals produced at the output 236 of the amplifier 234, corresponding to the variations of the sensor 54 at the input thereof.

A sample and hold circuit 264 is connected in series with a resistor 262 between the output 258 and the inverting input of the operational amplifier 254. The sample and hold circuit 264 comprises an operational amplifier 266 whose non-inverting input is connected via a line 268 to the output 258 of the operational amplifier 254. The operational amplifier 266 has its inverting input connected to ground and its output connected via a switch 270 to an input of a buffer 272 which has a capacitor 274 connected between its input and its output. The switch 270 is selectively activatable via a two input gate 276 which has one input thereof connected to ground and another input connected to receive a signal from the terminal 278. The terminal 278 is connected to receive a signal from the chopper disc sensors described above and via circuits to be described hereinbelow, corresponding to the periods when the chopper disc is cutting off the light from the radiant energy source and therefore the sample is in darkness.

Thus, when the sensor 54 is receiving no reflected energy from the dark sample, the output signal corresponding thereto at the terminal 258 is connected via the operational amplifier 266 and switch 270 to be held by the circuit comprising the gate 272 and capacitor 274. The same signal is also present via the resistor 262 at the inverting input of the operational amplifier 254, thus causing its output at terminal 258 to go to zero. When the chopper is passing light to the sample, a corresponding signal at the terminal 278 causes the element 276 to open the switch 270, whereby the dark level signal stored in the capacitor 274 is applied via the resistor 262 to the inverting input of the operational amplifier 254. Thus, the operational amplifier 254 has an input corresponding to the difference between the signal from the sensor 54 via the operational amplifier 234 and the dark period signal. Therefore, the circuit of FIG. 11 takes into account any change in the dark period response of the sensor 54 by continuously adjusting its output at terminal 258 in accordance therewith during the periods of illumination. It will be noted that a variable resistor 280 is provided to vary the biasing of the operational amplifier 266. The wiper arm 282 of the variable resistor 280 is connected to a suitable negative DC voltage supply. The wiper arm 282 serves to calibrate the foregoing circuitry at zero input when the connector 248 is connected to ground via the terminal 260, as described above.

Figure 12B:
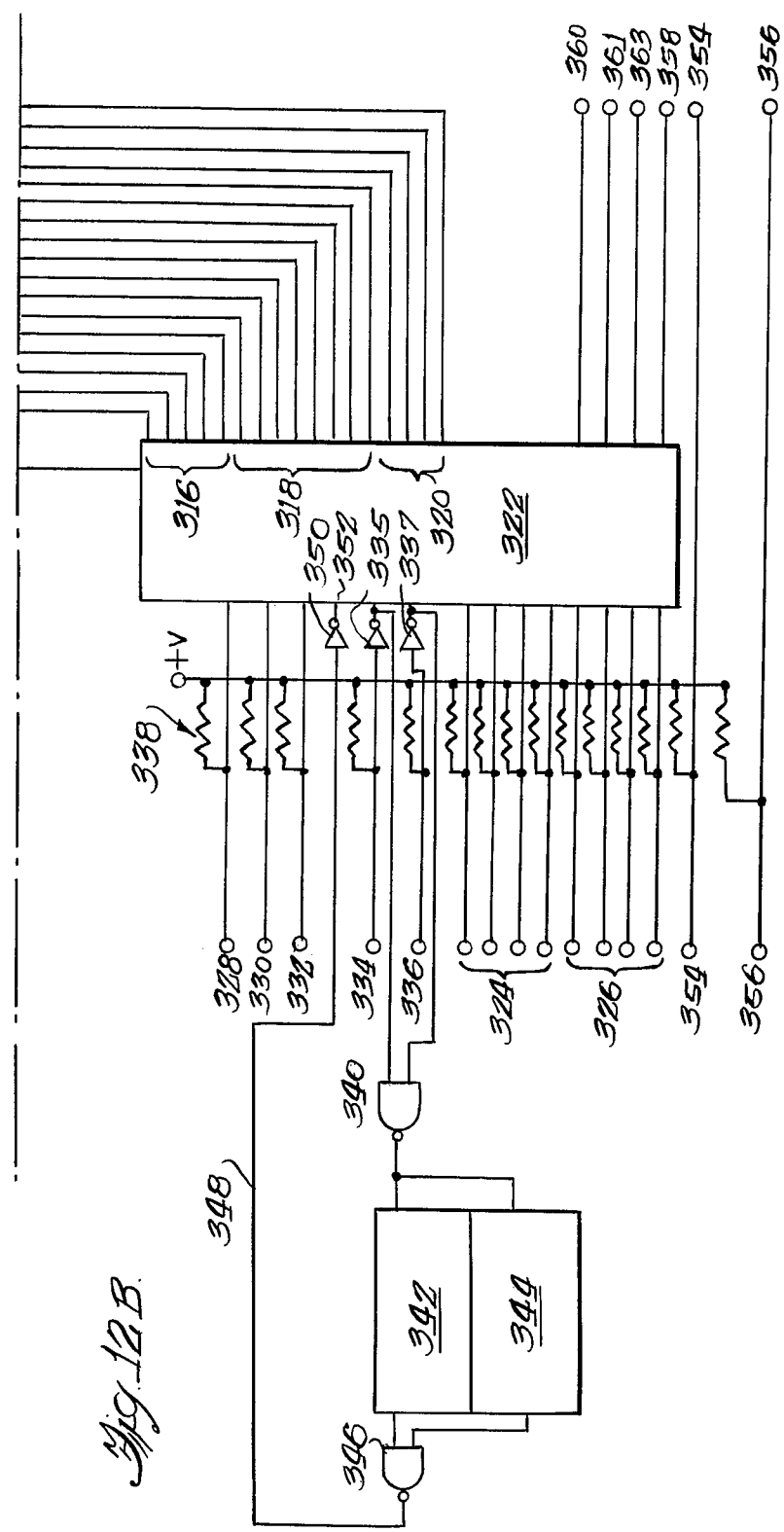

Referring now to FIGS. 12A and 12B, the input/output circuits 204 of FIG. 10 are illustrated in detail. A sample and hold circuit 284 has an input connected to the terminal 258 from the output of the pre-amp and level circuit of FIG. 11. The sensor element 142 of FIG. 8 comprises a light emitting diode 283 and a photo-responsive transistor 285 as described above. The output of the photo-responsive transistor 285 of the sensor element 142 at terminal 286 is connected to an input of a one shot circuit 288. Similarly, a terminal 290 receives the output of the photo-responsive transistor of the sensor element 144 of FIG. 8. The terminals 286 and 290 are each connected by a suitable pull-up resistor 287,291 to a positive voltage supply. Terminal 290 is connected to one input of a two input NAND gate 292, whose other input is connected to an output 294 of the one shot 288. The output 294 of the one shot 288 is also connected to one input of a two input NAND gate 296 whose other input is connected via an inverter 298 to the terminal 290. The output of the NAND gate 292 is connected to terminal 278 which is connected to activate the switch 270 in the sample and hold circuit 264 of FIG. 11. Thus, the gate 292 provides appropriate logic signals to open and close the switch 270 as the sample is respectively lighted and dark, due to the action of the chopper disc, as described above.

Output 300 of the NAND gate 296 is connected to a one shot circuit 302 and, via an inverter 304 to a control input of the sample and hold circuit 284. The output of the sample and hold circuit 284 is connected to an input of an analog to digital converter 310. The output 306 of the one shot 302 is connected via an inverter 308 to a convert input of the analog to digital converter 310. Thus, the sample and hold 284, in response to the logic signals developed by the gate 296, samples and holds signals from the pre-amplifier and level circuits of FIG. 11 substantially at the same portion of each signal during the passage of the slots 148 of the chopper disc 50 between the radiant energy source and the filters, as described above.

The sample and hold circuit 284 has an output on line 307 connected to the analog digital converter 310 whereby, in the manner known in the art, the received signals are sequentially passed to the analog to digital converter 310, the signal currently being held passing over the line 307 as a subsequent signal is being sampled from the input terminal 258. The analog to digital converter 310 has a 12 bit output, for high accuracy and resolution, over twelve lines designated generally 312. Thus, the lines 312 carry a twelve bit digital signal corresponding to the input signal set in on line 307. The lines 312 are connected to inputs of a peripheral storage unit (PSU) 314.

The peripheral storage unit 314 includes five control lines designated generally 316, four control lines designated generally 318 and an 8 bit bidirectional data input/output on eight lines designated generally 320. The lines 320 serve as data bus lines as will become apparent later. The lines 316, 318 and 320 are connected in commmon with corresponding control and data input/outputs on a second peripheral storage unit (PSU) 322 of FIG. 12B. The peripheral storage unit 322 has four input lines designated generally 324 and four input lines designated generally 326 connected to the four-by-four keyboard 26 of FIG. 1, the lines 324 corresponding to the vertical rows of the keyboard and the lines 326 corresponding to the horizontal rows thereof. Thus, a combination of input pulses to one of the lines 324 and one of the lines 326 corresponds to a unique one of the keys of the keyboard 26 of FIG. 1. Input lines 328, 330 and 332 to the peripheral storage unit 322 carry signals corresponding, respectively, to three possible positions of the key switch 30 of FIG. 1. Lines 334 and 336 are connected to the sensors 121 and 123 to receive signals therefrom corresponding to position of the drawer 34 of FIG. 1 when it is closed and opened, respectively. The lines 324, 326, 328, 330, 332, 334 and 336 are each provided with a suitable pull-up resistor, designated generally 338 to a positive voltage supply. The lines 334 and 336 are connected to the peripheral storage unit 322 via inverters 335 and 337, respectively, to provide suitable logic signals to the peripheral storage unit 322 from the drawer closed and drawer open signals, respectively. The junctions of the inverters 335 and 337 with the peripheral storage unit 322 are also connected to two inputs of a two input NAND gate 340 whose output is connected to an input of a one shot 342 and to an input of a one shot 344. The outputs of the one shots 342 and 344, respectively, are connected to two inputs of a two input NAND gate 346 whose output is connected via a line 348 and an inverter 350 to another input 352 of the peripheral storage unit 322. The input 352 provides a suitable logic signal to the peripheral storage unit 322, in addition to those provided via the lines 334 and 336 and inverters 335 and 337, corresponding to the position, completely closed or completely open, of the drawer 34. These signals indicate either that a sample contained in the sample receptacle 38 is to be analyzed or that the reference standard disc 40 is to be analyzed for calibration purposes. Terminals 354 and 356 are connected to receive signals corresponding to the actuation of the step switch 28 of FIG. 1 and are also provided with suitable pull-up resistors 338 to a positive voltage supply. An output 358 of the peripheral storage unit 322 produces an output signal each time a key of the keyboard 26 of FIG. 1 is depressed, to actuate a circuit for producing an audible sound to indicate to the operator that a key has in fact been depressed. Three outputs, 360, 361 and 363, of the peripheral storage unit 322, carry additional control signals.

Referring back to FIG. 12A, an input 362 to the peripheral storage unit 314 is provided with a pull-up resistor 364 to a positive voltage supply and carries the signal from the filter wheel sensor 105 indicative of the position of the filter wheel 98. An output line 366 of the peripheral storage unit 314 carries a control signal and output lines 368 and 370 of the peripheral storage unit 314 carry signals to the motor control circuit 220 for actuating the sample receptacle motor 56 and the filter disc motor 44, respectively. A line 372 connects an output of the analog to digital converter 310 with an input of the peripheral storage unit 314 to provide an additional control signal thereto. A line 373 connects a control terminal of the peripheral storage unit 314 with a control terminal of the peripheral storage unit 322.

Figure 14:
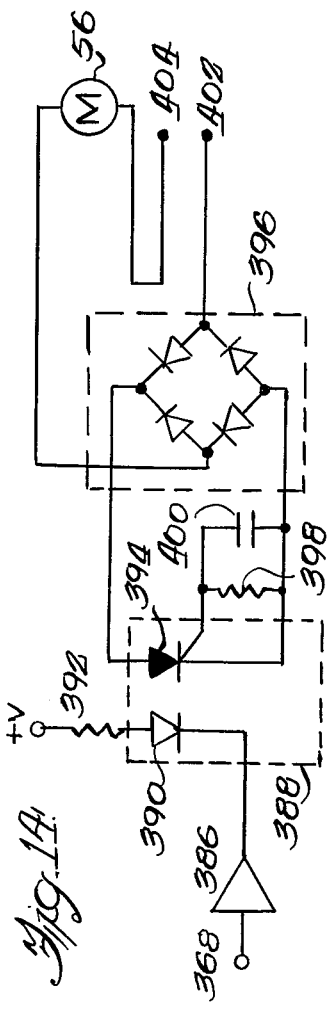
FIGS. 14 and 15 are a schematic diagram of the motor control circuits of FIG. 10.
Figure 13:
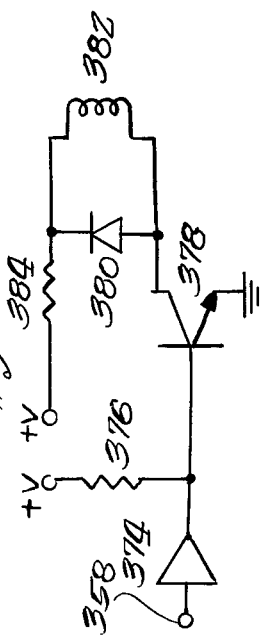
FIG. 13 is a schematic diagram of a circuit associated with keyboard controls of FIG. 10.
Figure 15:
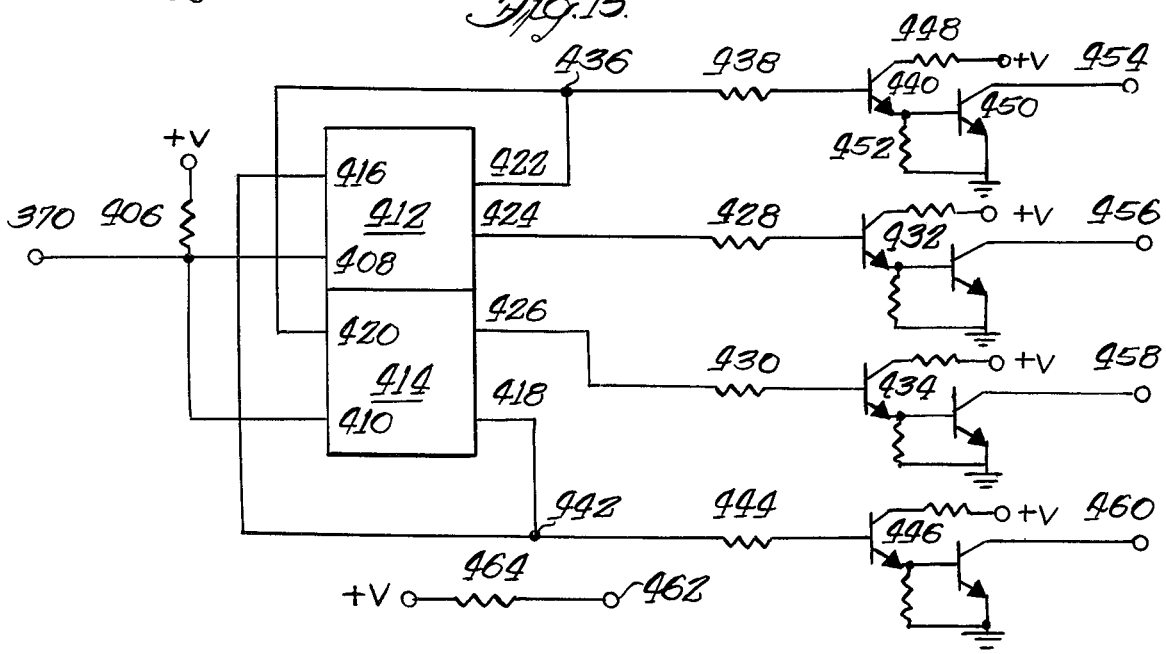

Referring now to FIGS. 13, 14 and 15, driver circuits for the audible key closures signal, sample motor 56 and filter disc motor 44, respectively, are illustrated. The circuits of FIGS. 14 and 15 comprise a portion of the motor control circuit 220 of FIG. 10. The audible keyboard response driver of FIG. 13 includes an input connected to terminal 358 of the peripheral storage unit 322 which activates the driver circuit in response to key closures at the inputs 324 and 326 thereof. The terminal 358 is connected to an input of a buffer 374 whose output is connected via a resistor 376 to a positive voltage supply and to the base electrode of a transistor 378. The transistor 378 has its emitter electrode connected to ground and its collector electrode connected to the anode of a diode 380 and one end of a solenoid 382. The diode 380 and solenoid 382 are connected in parallel and have their end opposite the collector of transistor 378 connected in series with a resistor 384 to a positive voltage supply. Thus, the driver of FIG. 13 converts the signal from the terminal 358 of the peripheral storage unit 322 to a suitable signal to drive the solenoid 382 to produce an audible sound responsive to the closure of a key on the keyboard. The motor driver circuit of FIG. 14 has an input connected to the terminal 368 of the peripheral storage unit 314 of FIG. 12A to receive a signal therefrom for actuating the sample receptacle motor 56 at the proper time. The terminal 368 is connected to the input of a buffer 386 whose output is connected to an input of an optoisolator 388, the input being the cathode of a light emitting diode 390. The anode of the light emitting diode (LED) 390 is connected in series with a resistor 392 to a positive voltage supply. The LED 390 turns on a photosensitive silicon controlled rectifier (SCR) 394 when energized by the signal at terminal 368 via the buffer 386. The SCR 394 is connected across a full wave rectifier circuit 396 and the gate electrode of the SCR 394 is connected to the cathode electrode thereof via the parallel combination of a resistor 398 and a capacitor 400. A suitable power source for the motor such as a 120 volt AC line is connected across terminals 402 and 404. Terminal 402 is connected to the full wave rectifier 396 and terminal 404 is connected to one end of the motor 56 the other end thereof being connected to the full wave rectifier circuit 396.

A driver circuit for the stepping motor 44 for the filter disc 98 is illustrated in FIG. 15. An input thereto is connected to the terminal 370 of the peripheral storage unit 314 of FIG. 12A to provide a signal thereto suitable for energizing the stepping motor at the proper intervals. The input at the terminal 370 is connected in series with a resistor 406 to a positive voltage supply. The input at terminal 370 is also connected to a pair of clock inputs 408 and 410 of a pair of D flip-flops 412 and 414. The D flip-flops 412 and 414 are connected as a sequence generator, the D output 416 of the flip-flop 412 being connected to the Q̄ output 418 of the flip-flop 414 and the D output 420 of the flip-flop 414 to the Q output 422 of the flip-flop 412. The $\overline{Q}$ and Q outputs 424 and 426 of the flip-flops 412 and 414, respectively, are connected via resistors 428 and 430 to the base electrodes of transistors 432 and 434, respectively. The outputs 420 and 422 are connected via a resistor 438 to the base electrode of a transistor 440. Similarly, the outputs 416 and 418 are connected via a resistor 442 to the base electrode of a transistor 446. The transistors 432, 434, 440 and 446 each comprise an input stage to one of four identical driver circuits, so that only one driver circuit need be described in detail. The collector electrode of the transistor 440 is connected via a resistor 448 to a positive voltage supply and the emitter electrode of the transistor 440 is connected to the base electrode of a transistor 450 and via a resistor 452 to ground. The transistor 450 has its emitter electrode connected to ground and its collector electrode connected to an output terminal 454 of the driver. Similarly, the other drivers have their outputs at terminals 456, 458 and 460, respectively. Thus, the driver circuit outputs at terminal 454, 456, 458 and 460 provide signals in the proper sequence as controlled by the sequence generator comprising the flip-flops 412 and 414 to energize or step the stepper motor 44 at the desired rate. A suitable positive voltage to the side of the motor 44 opposite the above described drivers is provided at the terminal 462 which is connected via a resistor 464 to a positive voltage supply.

Figure 16A:
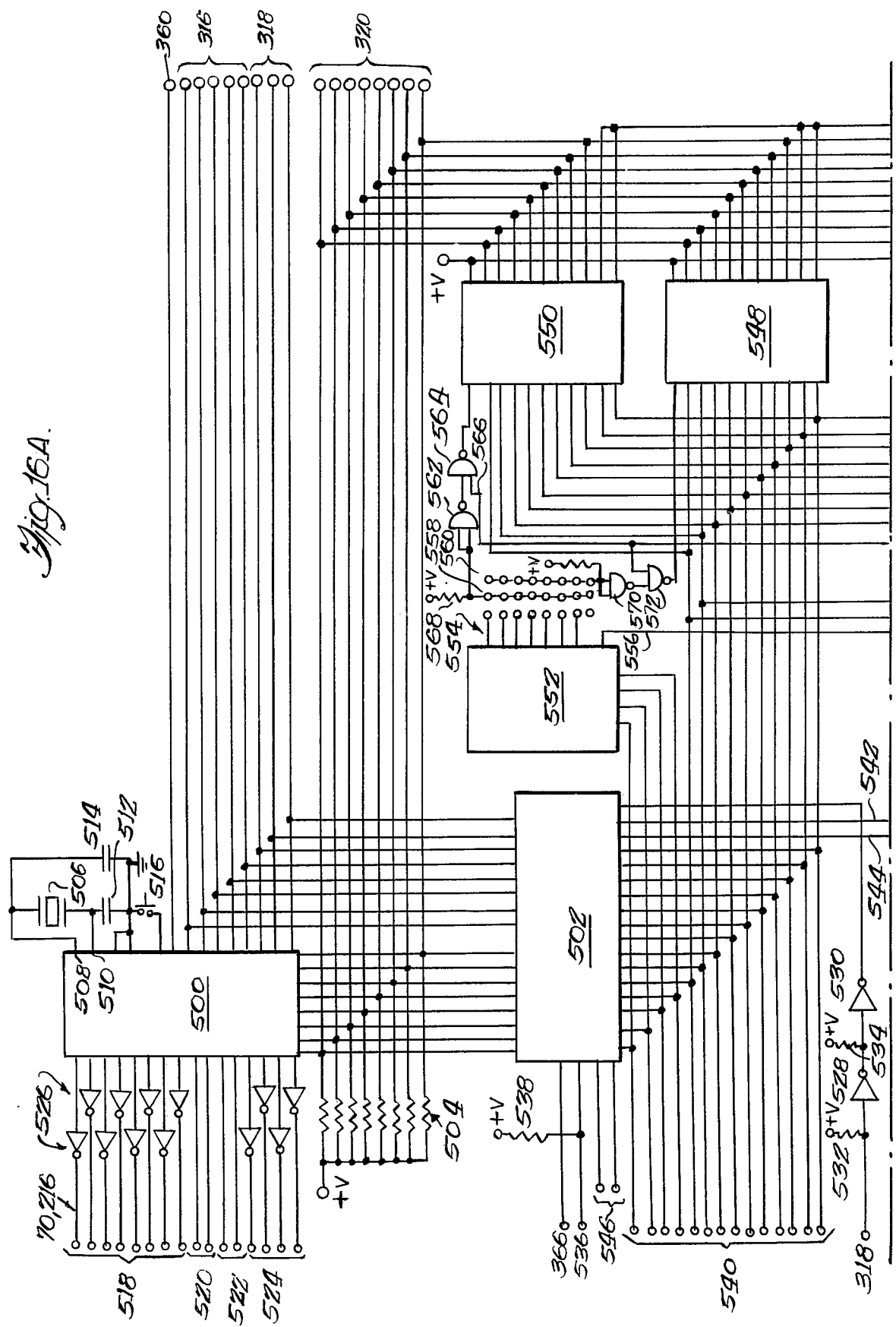
FIGS. 16A and 16B are a detailed schematic diagram of the central processing circuits of FIG. 10.
Figure 16B:
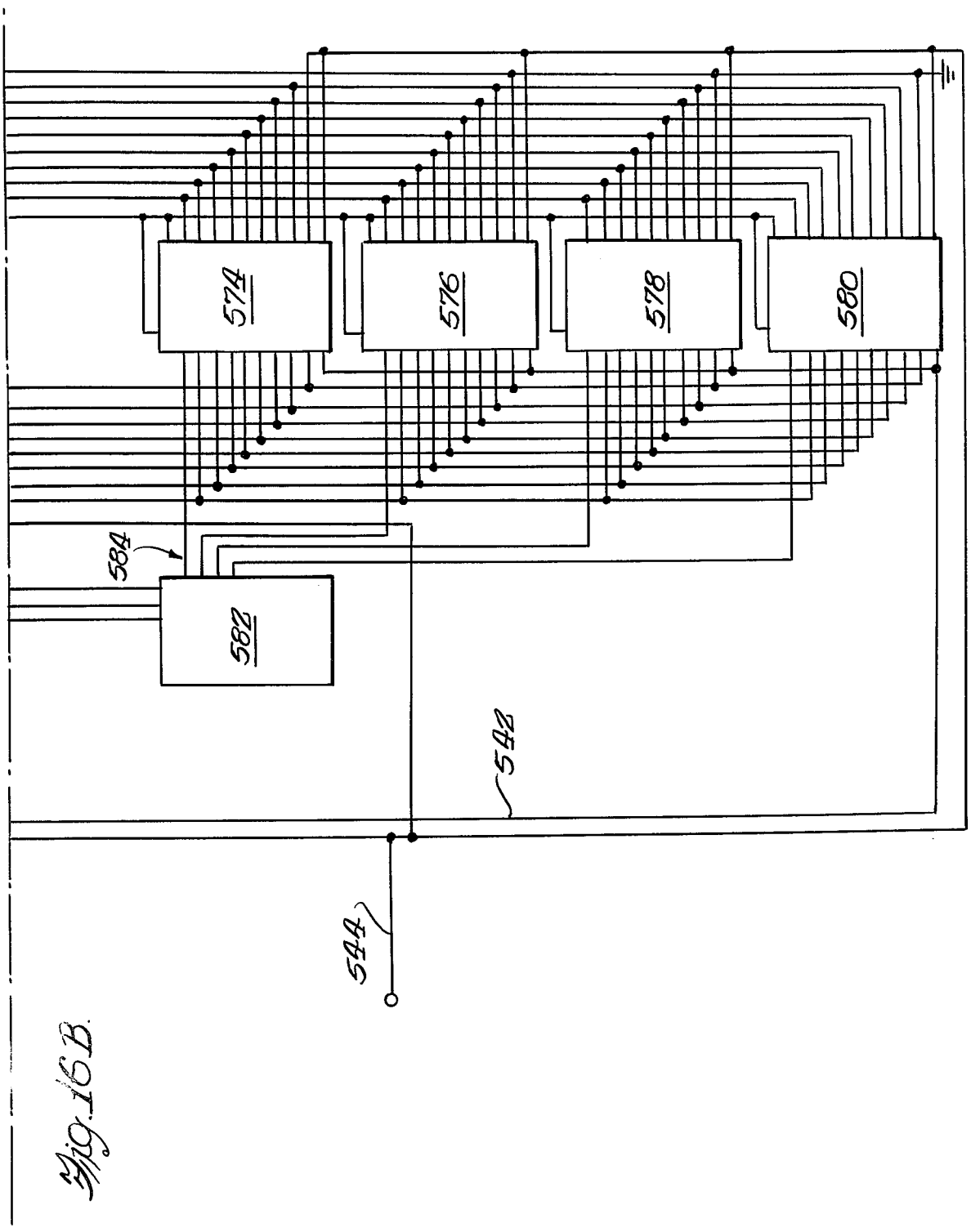

Referring now to FIGS. 16A and 16B, a central processing circuit 210 of FIG. 10 is illustrated in detail. The central processing circuit 210 includes a central processing unit (CPU) 500 which includes control terminals connected to the lines 316, and three of the lines 318 of the peripheral storage units 314 and 322 of FIG. 12A and bidirectional data terminals connected to the lines 320 of the peripheral storage units 314 and 322 of FIGS. 12A and 12B. The control signals over the lines 316 and 318 originate in the CPU 500 and control the operation of the respective peripheral storage units 314 and 322 connected thereto. The control lines 316 and 318 and the bidirectional data lines 320 are also connected to corresponding terminals of a static memory interface (SMI) unit 502. The bidirectional data lines 320 are each connected via suitable pull-up resistors, designated generally 504 to a positive voltage supply.

The central processing unit 500 includes an internal oscillator for generating appropriate clock signals for sequencing of overall system functions, via one of the control lines 318. The main clock oscillator frequency is controlled via a crystal element 506 connected at one end thereof to a terminal 508 of the CPU 500 and at the other end thereof to a terminal 510 of the CPU 500. The external connections for the clock oscillator portion thereof are made to suitable external elements such as capacitors 512 and 514, a reset switch 516, and to ground. These connections are made in the manner suitable for setting the frequency of the internal clock oscillator of the CPU 500 to a frequency of substantially two megahertz. The central processing unit 500 includes a plurality of output lines, designated generally 518, 520, 522 and 524 and corresponding to the connecting lines 70 and 216 of the block diagram of FIG. 10, for providing appropriate output signals to the display circuits 218 and printer 68. The individual lines of the display and printer outputs 70,216 are as follows: the lines 518 carry appropriate signals from the CPU 500 to operate both the display circuits and the printer; the lines 520 carry signals to the display circuits only; the lines 522 carry signals to the printer only; and the lines 524 carry signals to both the printer and the display circuits. It will be noted that the lines 518 and 524 each include an inverter-type buffer, designated generally 526 having an input connected to the corresponding terminal of the CPU 500 and an output comprising individual ones of the lines 518 and 524, respectively. The remaining one of the four control lines 318 of the peripheral storage unit 314 of FIG. 12A is connected to an input of the static memory interface 502 via inverters 528 and 530 connected in series and each having a pull-up resistor 532 and 534, respectively, to a positive voltage supply at its respective input. An additional control line 536 is connected to a terminal of the static memory interface 502 and has a pull-up resistor 538 to a positive voltage supply connected thereto. The line 536 receives a suitable control signal from the printer 68.

The static memory interface (SMI) 502 receives control inputs via the lines 316 and 318 from the central processing unit 500 and is adapted to receive and transmit data to and from the central processing unit 500 via the data bus lines 320. The SMI 502 is adapted to provide an appropriate data interface between the central processing unit 500 and the 8-bit data output thereof connected to the data bus lines 320 and memory devices to be described below. The static memory interface 502 is provided with 16 address lines, designated generally 540 and 546 to address the memory devices and with control lines 542 and 544 to provide suitable control signals for the memory devices in response to control signals from the CPU 500 via the lines 316 and 318. In the embodiment shown for purposes of illustrating the invention, the two address lines designated generally 546 are not used.

Suitably wired sockets 548 and 550 are provided for read-only memory devices of 1024 by 8-bit configuration and preferably of the ultra-violet erasable and programmable type. Suitable memory devices may optionally be inserted in the sockets 548 and 550 to provide capacity for read-only memory as will be explained in detail hereinbelow. Suffice it to say that the sockets 548 and 550 have a plurality of bi-directional data input-/output lines connected in common with corresponding ones of the data bus lines 320 and 10 address lines connected in common with corresponding ones of the last ten of the address lines 540 of the static memory interface 502.

A decoder 552 is provided including four inputs connected to the first four of the address lines 540 of the static memory interface 502. The decoder 552 is adapted to receive address signals from the static memory interface 502 and decode them onto eight outputs thereof designated generally 554 and a ninth output 556 thereof. The eight outputs 554 of the decoder 552 are selectively connectible to one or both of two groups of corresponding terminals connected along two lines designated generally 558 and 560 which are connected to appropriate logic for selecting one or both of the memory devices which may be optionally inserted in the sockets 548 and 550 as described above, to be addressed by the address lines 540 of the static memory interface 502. The line 558 is connected to both inputs of a two input NAND gate 562 whose output is connected to one input of a two input NAND gate 564 whose output is connected to a chip select input of the socket 550. The opposite input of the NAND gate 564 is connected via a line 566 to the control line 544 from the static memory interface 502. A pull-up resistor 568 to a positive voltage supply is also connected to the line 558. Similarly, the line 560 is connected to a pull-up resistor to a positive voltage supply and to the two inputs of a two input NAND gate 570. The output of the NAND gate 570 is connected to one input of a two input NAND gate 572 whose output is connected to the chip select terminal of the socket 548. The other input of the NAND gate 572 is also connected to the line 566 from the control line 544 of the SMI 502.

Similarly, four sockets 574, 576, 578 and 580 are provided for accommodating up to four random access memories of 256 by 8-bit configuration, which may be inserted to provide additional random access memory capacity. The sockets 574, 576, 578 and 580 are provided with connections to a suitable positive voltage supply, bi-directional data lines connecting corresponding data input/output terminals thereof with the data bus lines 320, and connections to the control lines 542 and 544 of the static memory interface 502. A second decoder 582, substantially identical to the decoder 552 is provided having a first input connected to the line 556 from the output of the decoder 552 and two inputs connected to the first two of the ten address lines 540 from the address inputs of the sockets 548 and 550. The decoder 582 includes four output lines designated generally 584 which are connected to the chip select inputs of the four sockets 574, 576, 578 and 580, respectively.

The decoder 582, in response to signals from the control lines 542 and 544, the line 556 from the decoder 552 and the address lines 540 of the static memory interface 502, is adapted to select and address a random access memory device which may be optionally installed in one of the sockets 574-580 to read and write data therefrom via the data bus lines 320 connected thereto.

In the instrument according to the present invention, all four of the sockets 574, 576, 578 and 580 are occupied by random access memories (RAM's) of 256 and 8-bit configuration. The aforementioned control and address signals are adapted to effect the storage of data in these random access memories corresponding to the multiple readings taken by the sensor 54 of FIG. 10, in accordance with the action of the chopper disc 50 and filter wheel 42 as described above. Similarly, and under the control of the aforementioned decoder 582 and control lines 542 and 544 of the static memory interface 502, the RAM's in the sockets 574 through 580 are adapted to transfer the data thus stored therein via the data bus lines 320 to the central processing unit 500, as called for thereby.

Figure 17:
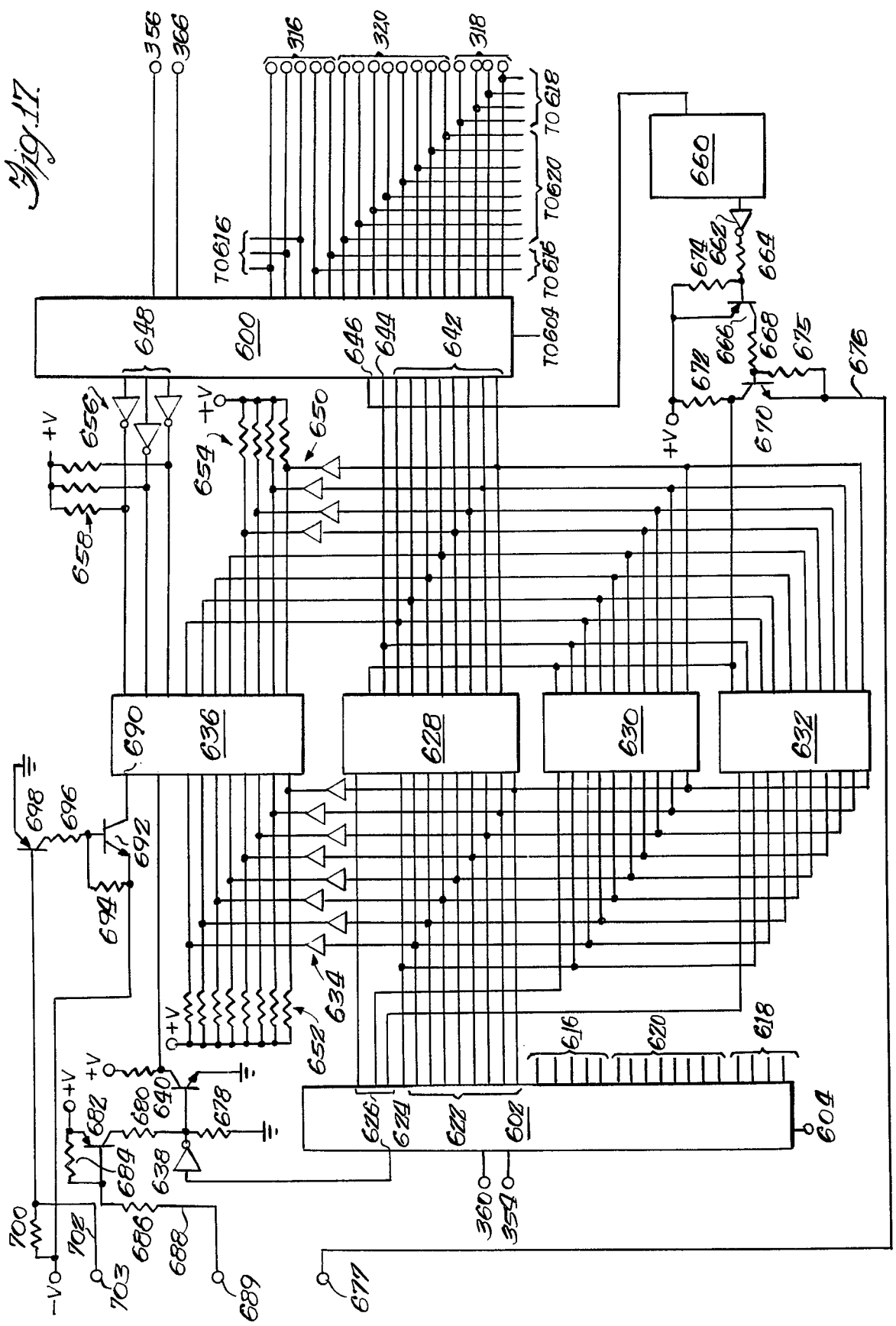

Referring now to FIG. 17, the memory circuits 214 of FIG. 10 are illustrated in detail. Peripheral storage units (PSU's) 600 and 602 are substantially identical to the peripheral storage units 314 and 322 of FIGS. 12A and 12B hereinbefore described. The peripheral storage unit 600 includes inputs from the control lines 316 and 318 to receive control signals from the central processing unit 500 of FIG. 16A and is also provided with input/output terminals connected to the data bus lines 320. Similarly, the peripheral storage unit 602 is connected at the terminals 616, 618 and 620 thereof to the lines 316, 318 and 320. The peripheral storage unit 600 includes additional control inputs at terminals 356 and 366 which are the same terminals as the like numbered terminals of FIGS. 12A and 12B. Similarly, the peripheral storage unit 602 includes additional control inputs at the terminals 354 and 360 which are the same terminals as the like numbered terminals of FIG. 12B. It will be noted that the signals on the terminals 354 and 360 correspond to the signals on a common line of the keyboard 26 and the step switch 28 of FIG. 1, respectively, for providing a suitable indication of the operation thereof to the peripheral storage unit 602, which is adapted to provide a suitable control signal in response thereto. A line 604 connects a control terminal of the PSU 600 with a corresponding terminal of the PSU 602 to carry suitable control signals therebetween.

The peripheral storage unit 602 includes a plurality of input/output lines 622, 624 and 626. Each lines designated 622 and the line 624 are connected as address lines to memory chips 628, 630 and 632, the corresponding address inputs of each being connected in common. The eight address lines 622 are also connected via eight buffers, designated generally 634, as address lines to a fourth memory chip 636. Three of the lines 626 are connected as chip select lines directly to the chips 628, 630 and 632, respectively, and a fourth line 626 is connected as a chip select line for the memory chip 636 via an inverter 638 connected to the base electrode of a transistor 640 whose collector electrode is connected to the chip select input of the memory chip 636. The memory chips 628, 630 and 632 preferably comprise ultraviolet erasable and programmable read-only memories of a 512 by 8-bit configuration. Similarly, the memory chip 636 preferably comprises an electrically erasable and programmable read-only memory of a 256 by 4-bit configuration.

The peripheral storage unit 600 includes a plurality of input/output lines 642, 644, 646 and 648. Eight lines designated generally 642 are connected as bi-directional data lines to the data input/output terminals of the memory chips 628, 630, 632 and 636, respectively, and are connected in common to the corresponding data terminals thereof. The lower four data lines 642 are connected to the memory chip 636 via suitable buffers designated generally 650. The buffers 634 and 650 are provided with suitable pull-ups to a positive voltage supply comprising resistors designated generally 652 and 654, respectively. Suitable control signals are also provided to the memory chip 636 via lines 648 of the PSU 600 which are connected to control inputs of the memory chip 636 via three inverter-type buffers, designated generally 656. The buffers 656 are provided with suitable pull-ups to a positive voltage supply comprising resistors 658.

Suitable read/write control signals are provided to the chips 628, 630 and 632 via the line 644 of the peripheral storage unit 600. Similarly, suitable program control signals are provided via the line 646 of the peripheral storage unit 600 to the memory chips 628, 630 and 632 via a suitable intervening circuit for preventing undesired programming instructions and the like thereto as, for example, due to transients which may be present during on and off switching of the main power to the instrument. This intervening circuit includes a one shot 660 whose input is connected to the line 646 from the PSU 600 and whose output is connected to an inverter 662. The output of the inverter 662 is connected via a resistor 664 to the base electrode of a PNP transistor 666 whose collector electrode is connected via a resistor 668 to the base electrode of a transistor 670. The collector electrode of the transistor 670 is connected in common to the program inputs of the memory chips 628, 630 and 632. Suitable biasing resistors 672 and 674 are provided to a positive voltage supply from the collector electrode of the transistor 670 and from the base electrode of the transistor 666, respectively. The emitter electrode of the transistor 666 is connected to a positive voltage supply. A resistor 675 is connected between the base and the emitter electrodes of the transistor 670 and a line 676 is connected to the emitter terminal thereof to provide a suitable signal thereto from a terminal 677 connected to a power up/down sensing circuit, to be described below, to protect the program inputs of the memory chips 628, 630 and 632 during power on/off switching.

Similarly, protection is provided for the chip select input of the memory chip 636 during power up/down switching by the transistor 640 and associated elements. The base electrode of the transistor 640 is connected via a resistor 678 to ground and via a resistor 680 to the collector electrode of a PNP transistor 682. The emitter electrode of the transistor 682 is connected to a positive voltage supply and connected via a resistor 684 to the base electrode thereof. The base electrode of the transistor 682 is connected via a resistor 686 to a line 688 which is connected to a terminal 689 to receive a suitable signal from the aforementioned power up/down sensing circuit to protect the chip select input of the memory chip 636 during power switching. A voltage supply terminal 690 of the memory chip 636 is also protected during power on/off switching by a transistor 692 and associated elements. The collector electrode of the transistor 692 is connected to the voltage supply terminal 690 and the emitter electrode thereof is connected to a negative voltage supply and via a resistor 694 to the base electrode thereof. The base electrode of the transistor 692 is connected via a resistor 696 to the collector electrode of a PNP transistor 698 whose emitter electrode is connected to ground. The base electrode of the transistor 698 is connected via a resistor 700 to a negative voltage supply and via a line 702 connected to a terminal 703 to receive an appropriate signal from the aforementioned power up/down sensing circuit to protect the power supply input 690 of the chip 636 from transients during power on/off switching.

The memory circuit of FIG. 17 is adapted to provide storage for a sufficient number of constants for the instrument to calculate the contents of a plurality of constituents for a plurality of different materials. It will be noted that the memory chips 628, 630, 632 and 636 include sufficient memory capacity to store a plurality of additional constants which may later be introduced via the keyboard for determining yet further constituents of the same or different materials or for revising constants already stored therein. In the latter case, a stacking concept is provided via the peripheral storage units 600 and 602 for reading out of the memory chips 628, 630, 632 and 636 only the latest or most recent constant stored therein for a particular constituent of a particular material when called for by the central processing unit 500 of FIG. 16A. it will be noted that the peripheral storage units 600 and 602 are substantially identical to the peripheral storage units 314 and 322 of FIGS. 12A and 12B.

The central processing unit 500 and static memory interface 502 of FIG. 16A together with the peripheral storage units 314 and 322 of FIG. 12A and 12B and the peripheral storage units 600 and 602 of FIG. 17 comprise the basic units of a microprocessor, preferably of the type generally designated F8 and manufactured by Fairchild. The central processing unit 500 preferably comprises an integrated circuit of the type generally designated 3850 and manufactured by Fairchild. Similarly, the peripheral storage units 314, 322, 600 and 602 preferably comprise integrated circuits of the type designated 3851 and manufactured by Fairchild, and the static memory interface 502 comprises an integrated circuit of the type designated 3853 and manufactured by Fairchild. The structure and function of these units is described in publications entitled "F8 User's Guide" and "Guide to Programming the F8 Micro Computer" copyright 1976, published by the Fairchild Camera and Instrument Corporation, which are incorporated herein by reference. Briefly, the central processing unit (CPU) 500 includes suitable components for directing and controlling, in proper sequence, of the measurement taking of the instrument via the optical module 41 and sensor 54 of FIG. 10, the accumulation of data therefrom, and calculation and display of the constituents of particular materials desired to be measured, in accordance with instructions via the keyboard and front panel controls 24 and with instructions contained in memory portions of the peripheral storage units (PSU's) 314, 322, 600 and 602. The peripheral storage units 314, 322, 600 and 602 include suitable input/output ports for connection to the other elements and components of the measurement instrument as described above, as well as permanent memory storage capacity for a complete set of instructions required by the CPU 500 to control the overall operation of the instrument. The static memory interface (SMI) 502 is adapted to provide a suitable interface between the CPU 500 and the memory devices 574, 576, 578 and 580 of FIG. 16B to store measurement data therein as accumulated and to return this data to the CPU 500 as called for to determine contents of constituents of the material being analyzed therefrom. Similarly, the input/output ports of the PSU's 600 and 602 are utilized as an interface between the CPU 500 and the memory devices 620, 630, 632 and 636 of FIG. 17 to select and transmit to the CPU 500 data contained therein, as called for, to perform, together with the measurement data, the necessary calculations to determine the desired constituents of the material being tested. The CPU 500 provides suitable control signals to all of the other units of the microprocessor via the control lines 316, 318 and 360, described above. The data bus lines 320 provide bidirectional lines for the transmission of data selectively throughout the system. It will be noted that the sockets 548 and 550 provided in the circuit of FIG. 16A are adapted to receive additional memory units, as described above, to supplement, or otherwise alter as desired, the instructions contained in the PSU's 314, 322, 600 and 602 for overall system operation.

Figure 18:
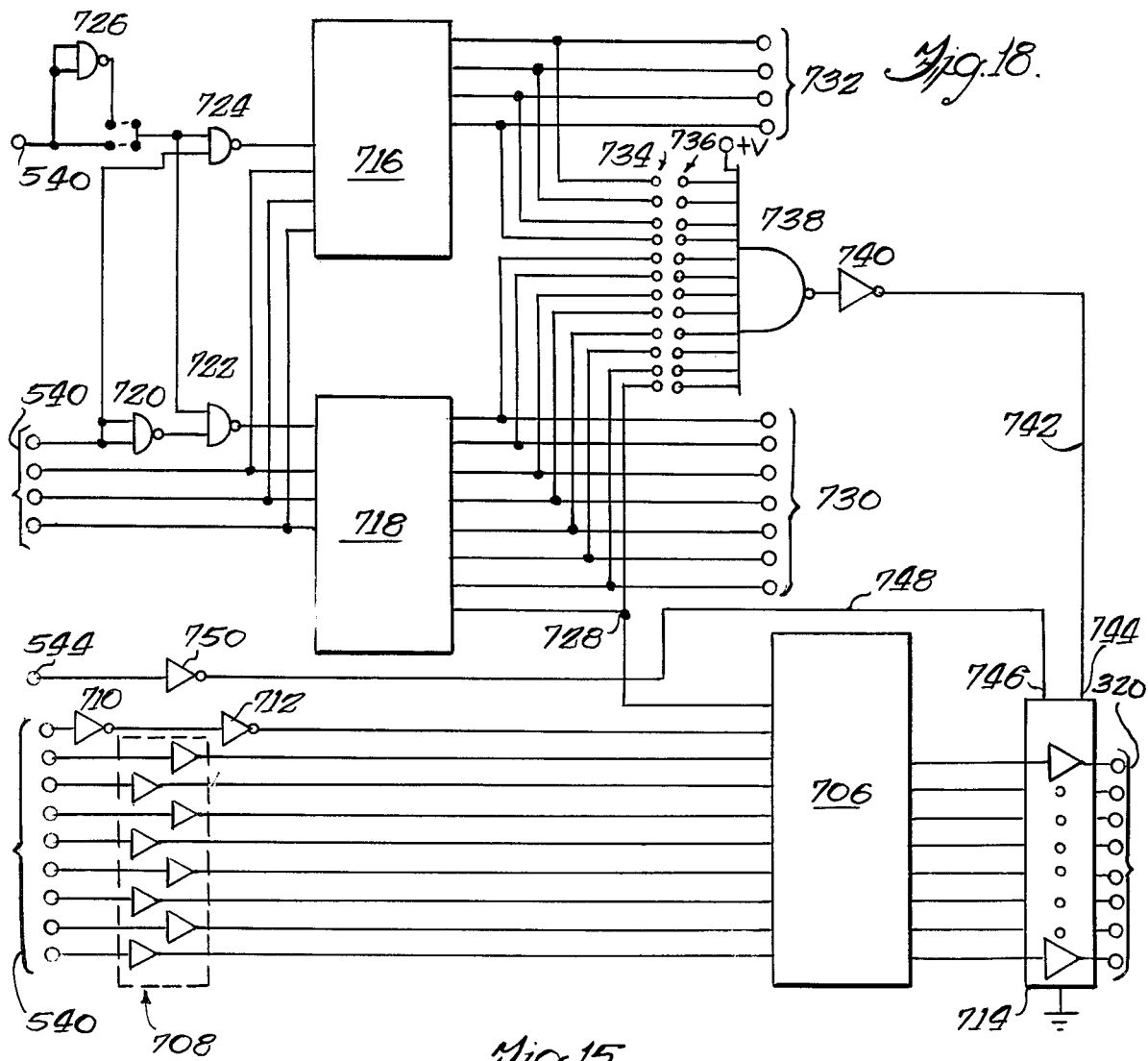
FIGS. 17 and 18 are schematic diagrams of the memory circuits of FIG. 10.

Referring now to FIG. 18, a circuit which may be used in an alternate embodiment of the microprocessor is illustrated. In the case where it is desirable to provide a set of instructions for the CPU 500 which may be changed or altered as desired, the circuit of FIG. 18 may be employed. In this alternate embodiment, the peripheral storage units 314, 322, 600 and 602 comprise peripheral input/output (PIO) integrated circuits designated 3861 and manufactured by Fairchild rather than the circuits designated 3851 of the preferred embodiment. All external terminals and connections thereof with other elements remain the same as described above. However, the 3861 integrated circuits serve only as peripheral input/output circuits and have no memory elements therein for the storage of instructions for the CPU 500. It will be noted, in this regard, that the instructions stored in the memory elements of the 3851 devices are permanent and un-alterable once inserted therein. The circuit of FIG. 18, therefore, provides alternative memory capacity for storing the instructions for the system in alterable form in a plurality of memory chips of the ultra-violet erasable and programmable ROM type and preferably of a 512 by 8-bit configuration. One such memory chip 706 is illustrated in FIG. 18, but it will be understood that up to twelve memory chips identical to the chip 706 may be employed in the circuit of FIG. 18, each chip having its corresponding address lines and data lines connected in common with those of the memory chip 706. The memory chip 706 includes nine address inputs connected to nine of the address lines 540 of the static memory interface 502 of FIG. 16A, eight of which are connected thereto via suitable buffers designated generally 708 and the ninth via a series connected pair of inverter-type buffers 710 and 712. Data input/output lines of the memory chip 706 are connected to the system data bus lines 320 via suitable buffers designated generally 714 which are preferably tri-state buffers.

Suitable chip select logic for selecting either the memory chip 706 or one of the additional chips which may be included as described above, includes decoders 716 and 718. The decoders 716 and 718 each include three inputs connected to three of the remaining address lines 540 of the static memory interface 502 of FIG. 16A. Fourth inputs of the decoders 716 and 718, respectively, are connected to the remaining two address lines 540 of the SMI 502 of FIG. 16A via suitable logic elements comprising two-input NAND gates 720, 722, 724 and 726. The first of the remaining two address lines 540 is connected to both inputs of the two input NAND gate 720 and to one input of the two input NAND gate 724. The output of the NAND gate 720 is connected to one input of the two input NAND gate 722 whose output is connected to the fourth input of the decoder 718. The second inputs of the NAND gates 722 and 724 are connected in common and may be selectively connected directly to the remaining address line 540 or to the output of a two input NAND gate 726, both of whose inputs are connected to the remaining address line 540. Which connection is chosen for the second inputs of the NAND gate 722 and 724 is dependent upon how many memory chips such as the memory chip 706 are utilized in the circuit of FIG. 18. The decoder 718 is adapted to select one of up to eight memory chips via output lines 728 and 730 thereof. The output line 728 is connected to the chip select input of the memory chip 706, while the seven output lines designated 730 are selectively connectable to corresponding chip select inputs of up to seven additional memory chips. Similarly, the decoder 716 includes four outputs lines 732 which are selectively connectable as chip select lines to the chip select inputs of up to four additional memory chips. The twelve chip select lines 728, 730 and 732 are also connected to twelve corresponding terminals designated generally 734 which are in turn selectively connectable to corresponding ones of twelve terminals designated generally 736 which comprise twelve inputs to a 13 input NAND gate 738 whose thirteenth input is connected to a positive voltage supply. One of the terminals 734 is connected to a corresponding one of the terminals 736 for each memory chip to be used in the circuit of FIG. 18. The output of the NAND gate 738 is connected via an inverter 740 and a line 742 to a common control input 744 of the tri-state buffers 714. Similarly, a second control input 746 of the tri-state buffers 714 is connected via a line 748 and an inverter 750 to the control line 544 of the static memory interface 502 of FIG. 16A. The signals received at the inputs 744 and 746 of the tri-state buffer 714 are suitable for driving a common control line for the individual buffers of the tri-state buffer 714. The tri-state buffer 714 is preferably of the type generally designated 81LS 95.

Referring now to FIG. 19, the display circuits 218 of FIG. 10 are illustrated in detail. Five seven segment display elements designated generally 752 correspond to the display elements of the line 170 of the display panel FIG. 9, as described above. Similarly, three seven segment display elements designated generally 754 and a seven segment display element 756 correspond to the display elements of the lines 180 and 186 of the display panel of FIG. 9. The seven segment display elements 752 and 754 also include a selectively energizable decimal point associated with each of the seven segment elements thereof. Thus, the segment driver inputs for each of the display elements 752 and 754 include seven inputs for selectively driving the seven segments of the digital display portion thereof and an eighth input for selectively driving the decimal point thereof.

To facilitate clarity in the illustration of FIG. 19 only the driver terminals of the first element of the three elements 754 and the last element of the five elements 752 are shown. It will be understood, however, that all of the remaining digital display elements 752, 754 and 756 include eight identical driver terminals, each of which is connected in common with the corresponding terminals of each of the other elements. The common lines connecting the corresponding driver terminals of the display elements are designated 760 through 767, respectively. Driver circuits connected to each of the lines 760 through 767 are identical and therefore, only one such driver circuit need be described in detail.

The output terminals 518 of the CPU 500 of FIG. 16A are the same as the terminals designated 518 of FIG. 19. Each of the terminals 518 is connected, respectively, to a corresponding one of the lines 760 through 767, thereby driving corresponding segments of each of the seven segment elements of display. A typical terminal 518a is connected via a resistor 768 to a positive voltage supply and via a resistor 770 to the base electrode of a transistor 772. The transistor 772 has its emitter electrode connected to ground and its collector electrode connected via a resistor 774 to the line 767. A BCD to decimal decoder 776 is provided for selecting individual ones of the digital display elements 752, 754 and 756. The decoder 776 includes nine output lines 778, one of which is connected to each of the display elements 752, 754 and 756 by identical circuits, whereby only one such circuit will be described in detail. An output line 778a of a decoder 776 is connected via a resistor 780 to the base electrode of a PNP transistor 782. The transistor 782 has its emitter electrode connected to a positive voltage supply and its collector electrode connected to digit driver terminals 784 and 786 of the display element 752a.

Lamps for selectively back-lighting the message panels 172, 174, 176, 178, 182, 184, 188, 190 and 193 through 200 of the display panel of FIG. 9, are illustrated as lamps 776 through 778. It will be understood that the lamps 776 and 778 correspond to the back-lighted message panels 172 and 200, respectively, the remaining panels being back-lighted by identical lamps driven by identical circuits, whereby only the first and last ones thereof comprising the lamps 776 and 778, have been illustrated. A pair of eight-output latches 780 and 782 include one output connected to a driver circuit for each of the aforementioned lamps. As the driver circuits are identical only that associated with the lamp 776 will be described in detail. A first one of the outputs of the latch 780 is connected via a resistor 784 to a positive voltage supply and via a resistor 786 to the base electrode of a transistor 788. The transistor 788 has its emitter electrode connected to ground and its collector electrode connected to one side of the lamp 776 whose other side is connected to a positive voltage supply. A resistor 790 is connected between the collector electrode of the transistor 788 and ground.

The latches 780 and 782 each include a control input connected to one of the two lines designated 520 for receiving a suitable control signal from the central processing unit 500 of FIG. 16A. Suitable signals to the decoder 776 and the latches 780 and 782 for selecting the proper digital display elements and lamps, respectively, to be energized thereby, are provided via the lines 524 from the central processing unit 500 of FIG. 16A. The latches 780 and 782 each have four inputs connected to the four lines designated 524. The decoder 776 is connected directly to two of the lines 524. A third one of the lines 524 is connected to one input of a two input NAND gate 792 whose output is connected to one input of a two input NAND gate 794 whose output is connected to an input of the decoder 776. Similarly, the remaining one of the lines 524 is connected to one input of a two input NAND gate 796 whose output is connected to one input of a two input NAND gate 798 whose output is connected to a remaining input of the decoder 776. The second inputs of the NAND gates 792 and 796 are connected to a positive voltage supply. The second input of the NAND gates 794 and 798 are connected to the output of a one-shot 800 whose input is connected to the first one of the lines 524.

Figure 20:
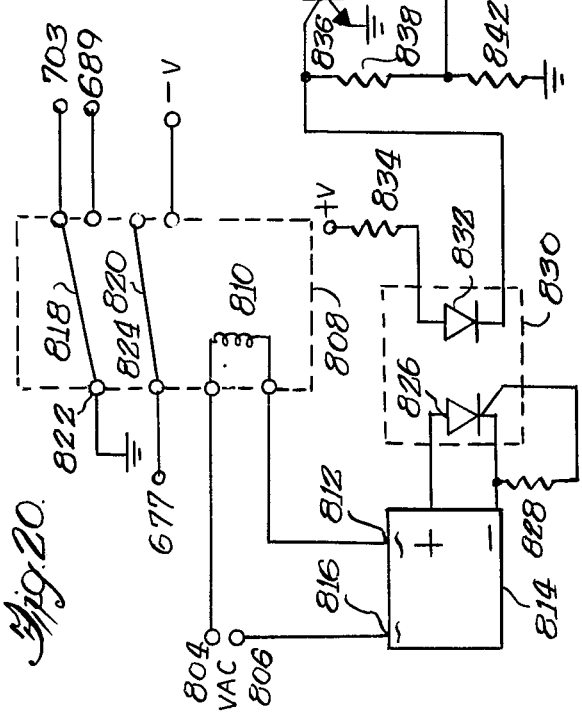
FIG. 20 is a schematic diagram of a circuit associated with the memory circuit of FIG. 17.

Referring now to FIG. 20, a power up/down circuit for providing suitable signals to the terminals 677, 689 and 709 if the memory circuit of FIG. 17 for protecting the memory chips thereof during power on/off switching is illustrated. Terminals 804 and 806 are connected to a suitable source of AC voltage. A relay 808 includes a coil 810 connected between the AC terminal 804 and one terminal 812 of a full wave rectifier 814 whose terminal 816 is connected to the AC terminal 806. The relay 808 includes two movable contactors 818 and 820. The contactor 818 has one end 822 thereof connected to ground and the other end thereof selectively movable between a normally closed and a normally open position. In the normally closed position the contactor 818 completes a connection between ground and the terminal 703 of FIG. 17. When the coil 810 is energized, the contactor 818 is activated thereby to normally open terminal, which completes a connection between ground and the terminal 689 of FIG. 17. Similarly, the movable contactor 820 has one end 824 thereof connected to the terminal 677 of the circuit of FIG. 17 and the other end thereof selectively movable between a normally closed and a normally open position. When the contactor 820 is in the normally closed position the terminal 677 is open circuited thereby. When the contactor 820 is actuated by the coil 810 to its normally opened position the terminal 677 is connected to a negative voltage supply thereby. The coil 810 is energized at power on by the AC voltage at terminals 804 and 806 via the full wave rectifier 814, the passage of current therethrough being controlled by a silicon controlled rectifier (SCR) 826. The anode of the SCR 826 is connected to the positive terminal and the cathode of the SCR 826 is connected to the negative terminal of the full wave rectifier 814. A resistor 828 connects the gate of the SCR 826 to the cathode thereof. The SCR 826 comprises a photo-responsive-type SCR and is part of an opto-isolator 830, the other portion thereof comprising a light emitting diode (LED) 832 for selectively energizing the photo-responsive SCR 826 into conduction. The LED 832 has its anode connected via a resistor 834 to a source of positive voltage which is energized when power is on. The cathode of the LED 832 is connected to the collector terminal of the transistor 836 and via a resistor 838 to the base electrode of a transistor 840. The transistor 840 has its emitter connected to ground, its base connected via a resistor 842 to ground and its collector connected via a resistor 844 to the base electrode of the transistor 836, whose emitter is connected to ground. The base electrode of the transistor 836 is connected via a resistor 846 to the anode of a diode 848 whose cathode is connected to a positive voltage supply, which is energized when the power is on. The anode of the diode 848 is also connected to one side of a capacitor 850 whose other side is connected to ground and a resistor 852 is connected in parallel with the diode 848. Thus, when power is switched on the positive voltage supplies will be energized whereby the LED 832 will be energized thereby causing the SCR 826 to go into conduction, completing the current path through the full wave rectifier 814. Therefore, the AC voltage at the terminals 804 and 806 will be transmitted via the full wave rectifier 814 to the coil 810 for actuating the movable contactors 818 and 820 from their normally closed to their normally open positions as described above.

Figure 21:
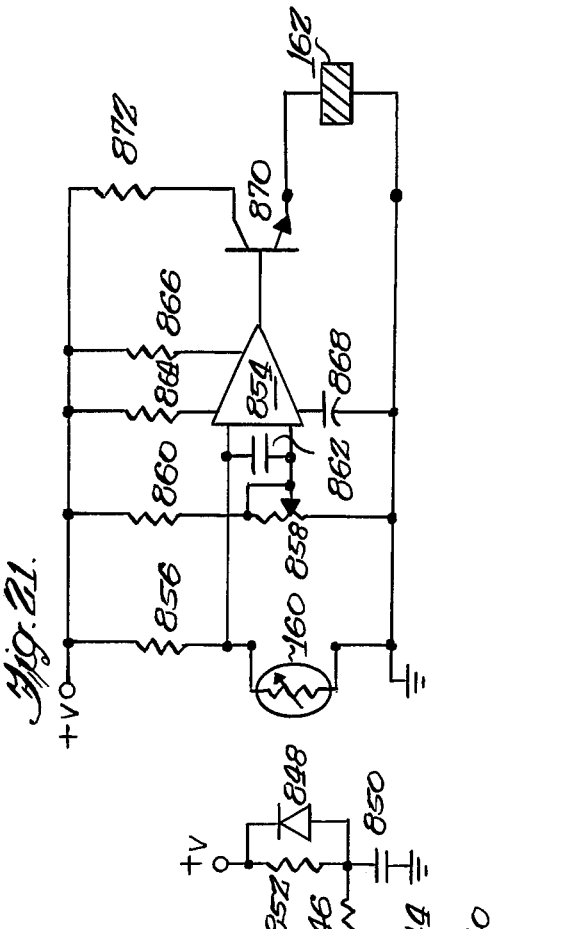
FIGS. 21 and 22 are schematic diagrams of the temperature control circuits of FIG. 10.

Referring now to FIG. 21, the temperature control circuit 60 of FIG. 10 is illustrated in detail. The temperature sensor 160 mounted on the infrared sensor 54, as best seen in FIG. 3, preferably comprises a temperature sensitive resistor. One end of the temperature sensor 160 is connected to ground and the opposite end is connected to one input of a comparator 854 and via a resistor 856 to a positive voltage supply. The opposite input of the comparator 854 is connected to the wiper arm of a variable resistor 858 which is connected, in series with a resistor 860, between the positive voltage supply and ground to form a voltage divider. Thus, the comparator 854 compares the signal across the temperature sensor 160 with a signal set by the movement of the wiper arm on the variable resistor 858, which corresponds to a desired temperature setting. The two input terminals of the comparator 854 are connected via a capacitor 862. The comparator 854 is also provided with suitable connections to the positive voltage supply via resistors 864 and 866 and to ground via a capacitor 868. The output of the comparator 854 is connected to the base electrode of a transistor 870 whose collector electrode is connected via a resistor 872 to the positive voltage supply. The emitter electrode of the transistor 870 is connected to one side of the thermo-electric cooler 162 whose opposite side is connected to ground. Thus, the thermo-electric cooler 162 is energized via the transistor 870 and the comparator 854 when the signal from the temperature sensor 160 indicates that the temperature thereof exceeds the temperatuure set by the variable resistor 858.

Figure 22:
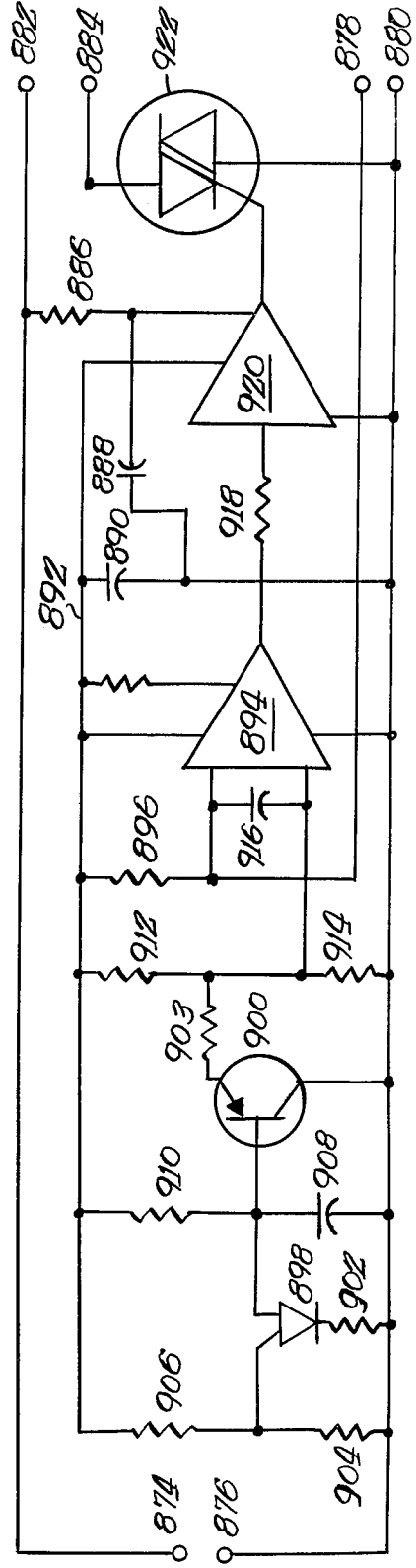

Referring now to FIG. 22, the temperature control circuit 58 of FIG. 10 is illustrated in detail. Terminals 874 and 876 are across a 120 volt AC line. The temperature sensor 164, illustrated in FIG. 3, preferably comprises a thermister and is connected across terminals 878 and 880. The heater 166, best seen in FIG. 3 preferably comprises a resistive heating element of substantially 75 watts and is connected across the terminals 882 and 884. It will be noted that the terminals 880 and 882 are connected directly to the terminals 876 and 874, respectively. The side of the 120 volt AC powerline at terminals 874 and 882 is connected via a resistor 886, a capacitor 888 and a capacitor 890 to a line 892. The terminal 878 is connected to one input of a comparator 894 for transmitting a signal proportional to the temperature from the temperature sensor 164 thereto. The terminal 878 is also connected via resistor 896 to the line 892. A second input signal to the comparator 895 is provided by a ramp generator comprising a programmable unijunction transistor (PUT) 898 and a PNP transistor 900. The PUT 898 has it cathode electrode connected via a resistor 902 to the terminal 876 of the AC line, a gate electrode connected via a resistor 904 to the terminal 876 and via a resisotr 906 to the line 892, and its anode electrode connected via a capacitor 908 to the terminal 876 and via a resistor 910 to the line 892. The anode electrode of the PUT 898 is also connected to the base electrode of the transistor 900 whose collector electrode is connected to the terminal 876. The emitter electrode of the transistor 900 is connected via a resistor 903 to the opposite input of the comparator 894. The junction of the resistor 903 with the opposite input of the comparator 894 is also connected via resistor 912 to the line 892 and via a resistor 914 to the terminal 876. A capacitor 916 is connected between the two inputs of the comparator 894. The comparator 894 is also provided with suitable connections to line 892 and the AC terminal 876. The output of the comparator 894 is connected via a resistor 918 to the input of a buffer 920 which is connected to function as a zero voltage switch. The buffer 920 is provided with suitable connections to the line 892 and to the AC terminal 876 and to the junction of the resistor 886 and the capacitor 880. The output of the buffer 920 is connected to the gate input of a power triac 922 which is provided with suitable connections to the heater at terminal 884 and to one side of the AC power line at terminals 876 and 880. Thus, the comparator 894 serves to compare the temperature-proportional output of the temperature sensor 164 at the terminal 878 with a signal proportional to a predetermined desired temperature and, via the zero voltage switch 920, to turn the power triac 922 on and off to supply power to the heater 166 when the temperature at the sensor 164 falls below the predetermined desired temperature.

It will be noted that the integrated circuit components described above are further provided with suitable power supplies and suitable connections thereto in the manner known in the art. The power supplies and many of the connections thereto have been omitted in the description and drawings to facilitate clarity therein, but will be understood as being included.

For purposes of affording a more complete understanding of the invention, it is advantageous now to provide a brief functional description of the operation thereof. It will be noted that the four-by-four pushbutton array keyboard 26 may have the individual pushbuttons thereof labelled in appropriate fashion. For example, ten of the pushbuttons may be labelled 0 through 9 and located similarly to the arrangement of the pushbuttons on a calculator. The remaining six pushbuttons may be labelled with appropriate words or symbols to indicate additional functions, to be described below.

The sample receptacle 38 may be removed from the drawer 34 and filled with a sample of the material to be analyzed. Alternatively, any number of identical sample receptacles may be filled in advance with one of a plurality of materials to be analyzed, and inserted, one at a time, into the drawer 34.

To initiate a measurement, the drawer 34 is closed and the instrument is actuated thereby to begin collecting measurement data from the sample, as described above, at which time the test message 188 of the display panel 32 is lighted. A numbered pushbutton of the keyboard 26 is actuated followed by actuation of a second pushbutton thereof which may be labelled "grain" to indicate the identity of material in the sample receptacle. One or more of the digits 180 will be lighted along with the product message 182 to indicate the identity of the material thus selected.

Upon completion of measurements and computations, the readout of constituent percentages via the digits 170 occurs. A first constituent percentage is indicated by the lighting of the percent message 172, the constituent message 184 and digits of the elements 180 to identify the constitutent being displayed. Remaining constitutent percentages for the selected material are displayed by depressing the step switch 28, which causes successive constituent percentages to be displayed in the same manner. When all the constituent percentages have been displayed, the sample drawer is opened, actuating the instrument to begin testing the reference standard 40 as a built-in test or check on the accuracy of the instrument. If the reference standard 40 fails to test correctly an error message will be presented. If the reference sample 40 tests out correctly, the insert sample message 190 will be lighted to indicate that the instrument is ready to perform measurements on another sample of material.

In order to enter new constants into the memory for expanding or updating the measurement capabilities of the instrument, the key switch 30 may be actuated by a key to the appropriate position and the constants to be written into memory are entered by depressing the appropriate number pushbuttons of the keyboard 26. The constants are first entered into volatile or RAM memory elements and verified by the display digits of the display panel 32. Numbered pushbuttons on the keyboard 26 are then actuated to identify the material and constituent number of the constant so entered, followed by actuation of another pushbutton of the keyboard 26 to enter the constant to non-volatile memory. Appropriate messages and digits of the display panel 32 are lighted in response to the foregoing keyboard pushbutton actuations, to verify the response of the instrument thereto to the operator.

It will be appreciated that the instrument described in the foregoing will be suitable for many applications. In particular, the optical portions thereof are applicable to other systems using optical measuring techniques such as spectro photometers, thermal sensors, pollution sensors and the like, as well as for measuring the optical properties associated with certain constituents of grain products. In particular, the use of the described microprocessor in connection with the instrument of the present invention renders the instrument extremely versatile. For example, the programable memory circuits described make it possible to alter the specific instructions carried out by the central processing unit to adapt the instrument to perform measurements and calculate results therefrom according to a variety of sequences of operations and calculations. Also, a wide variety of constant data information may be selectively stored in the programmable memory units of the instrument for providing a constant data base upon which a wide variety of measurements and calculations may be based.

The instrument according to the present invention, due to the unique and novel features of the optics portion thereof as well as the reliable and high-speed operation of the microprocessor portion thereof, makes it possible to obtain measurements, to perform calculations, and either display or print results therefrom with heretofore unprecendented speed and accuracy. The possibility of operator error is further minimized by the predetermined set of instructions executed via the microprocessor portion thereof as well as instructions included therein for alerting the operator to any errors, malfunctions or other problems which arise during the course of operation of the instrument.

As a specific example, to which no limitation is intended, an exemplary program for the described microprocessor system is reproduced on the following pages. This program is in "machine language" or "object code".

```
M0000 = 1A 20 C0 B9 74 85 70 65
M0008 = B0 B1 B4 B8 27 20 27 21
M0010 = 27 24 27 25 27 0E B6 27
M0018 = 22 27 26 27 12 50 2A 20
M0020 = 00 17 30 94 FD 20 19 50
M0028 = 31 94 FE 30 94 FB 20 AE
M0030 = BB 73 6A 20 0C BC 20 8E
M0038 = BD 20 70 57 63 68 71 5C
M0040 = 70 62 5C 64 5D 5D 5D 5D
M0048 = 67 5D 20 FE 56 71 55 28
M0050 = 14 F6 2A 00 5D 28 00 62
M0058 = 28 00 66 90 50 76 79 38
M0060 = 38 3F 08 29 12 62 08 77
M0068 = 51 41 22 40 50 28 37 E0
M0070 = 41 22 80 50 28 37 E0 31
M0078 = 82 F0 63 68 71 FC 94 07
M0080 = 20 4C 50 28 37 E0 0C 08
M0088 = 67 6B 20 79 5E 20 50 5E
M0090 = 5E 7F F0 54 40 14 55 20
M0098 = 37 50 28 30 D6 45 25 00
M00A0 = 94 02 7A 54 28 30 D6 47
M00A8 = 21 70 57 0C 70 58 20 8E
M00B0 = 50 28 37 E0 28 31 30 64
M00B8 = 69 4C 21 30 22 04 5C 18
M00C0 = 90 FF 71 58 20 4A 50 90
M00C8 = E9 73 58 20 8D 50 28 37
M00D0 = E0 90 F2 20 4A 50 28 37
M00D8 = E0 20 8A 50 28 37 E0 26
M00E0 = 25 21 01 84 D8 28 36 93
M00E8 = 28 35 81 63 6B 70 5C 28
M00F0 = 35 AF 26 21 50 21 10 84
M00F8 = FA 7F F0 84 10 63 6B 4C
M0100 = 25 90 84 09 24 10 5C 28
M0108 = 35 AF 90 E7 63 6B 4C 14
M0110 = 50 71 55 20 FE 56 28 15
M0118 = 0B 48 22 10 58 29 34 72
M0120 = 63 6B 20 F0 FC 5C 28 35
M0128 = 76 64 28 36 6A 73 52 28
M0130 = 12 7A 63 6B 7F FC 13 50
M0138 = 13 C0 24 C2 56 71 55 64
M0140 = 28 15 6C 63 68 7F FC 50
M0148 = 4C 14 E0 84 06 4C 1F 5C
M0150 = 90 D5 28 12 5E 18 90 FF
M0158 = 70 58 62 68 7F FC 22 08
M0160 = 5C 28 0C 85 94 9D 20 10
M0168 = 58 28 0B 73 28 0B AD 28
M0170 = 0C AE 64 6B 70 CE 84 27
M0178 = 4C 14 94 26 48 22 20 58
M0180 = 20 10 5C 28 10 E0 84 1F
M0188 = 64 6A 20 10 CC 5C 25 9F
M0190 = 82 F2 78 50 28 00 87 48
M0198 = 22 40 58 18 90 FF 29 02
M01A0 = 15 28 10 E0 94 ED 64 6A
M01A8 = 4C 53 20 10 5C 28 10 E0
M01B0 = 64 6A 43 5C 62 68 94 2F
M01B8 = 4C 22 10 5C 28 10 99 28
M01C0 = 03 49 64 72 52 28 12 7A
M01C8 = 6F 20 10 FC 23 10 5C 63
M01D0 = 6C 70 5D 5D 20 10 5D 71
M01D8 = 5C 28 16 93 28 2E 30 63
M01E0 = 2A 20 7C 28 36 3A 48 21
M01E8 = 20 84 06 64 6A 20 10 5C
M01F0 = 28 10 E0 34 1E 64 6A 4C
M01F8 = 24 10 5C 25 9F 82 F2 48
M0200 = 21 10 84 0A 48 21 EF 58
M0208 = 28 0D 82 64 6A 20 10 5C
M0210 = 90 DF 28 10 99 28 03 49
M0218 = 28 02 D6 28 04 6E 67 6C
M0220 = 70 5C 20 10 F8 84 07 28
M0228 = 0B FF 28 04 9E 28 03 29
M0230 = 62 68 4C 21 30 23 30 84
M0238 = 04 29 02 BA 63 2A 20 A8
M0240 = 28 36 3A 64 6F 20 10 5E
M0248 = 2A 20 E4 16 5E 20 F0 8A
M0250 = 5E 70 5C 63 5D 5D 71 5D
M0258 = 72 5C 28 16 93 28 02 D6
M0260 = 62 2A 20 7C 28 36 6A 28
M0268 = 16 12 62 2A 20 A8 28 36
M0270 = 6A 28 16 12 28 02 E1 28
M0278 = 04 6E 67 6C 20 58 5C 20
M0280 = 10 F8 84 34 28 0C E4 2A
M0288 = 02 EC 28 0D 11 2A 20 D1
M0290 = 2C 2A 20 E4 16 51 16 52
M0298 = 41 14 50 94 06 2C 16 2C
M02A0 = 90 04 28 0C F5 7F F1 50
M02A8 = 28 0C F5 2C 15 2C 42 14
M02B0 = 50 28 0C F5 28 04 9E 28
M02B8 = 03 29 20 10 F8 84 10 20
M02C0 = 20 F8 84 04 29 01 F5 48
M02C8 = 21 EF 58 28 0D 82 20 20
M02D0 = F8 94 F2 29 02 15 74 50
```

```
M02D8 = 6C 64 4C 63 5D 30 94 FA    M04A8 = 0D 22 20 25 2A 20 DF 17
M02E0 = 1C 74 50 6C 63 4C 64 5D    M04B0 = 28 0C 31 62 68 4C 21 80
M02E8 = 30 94 FA 1C 07 00 40 20    M04B8 = 84 0A 2A 04 D6 28 0D 11
M02F0 = 20 2E 20 25 4D 10 7F 3A    M04C0 = 28 0C 31 62 68 4C 21 40
M02F8 = 10 17 08 28 36 D2 10 16    M04C8 = 84 0A 2A 04 E8 28 0D 11
M0300 = 15 65 6C 5D 10 16 14 5D    M04D0 = 28 0C 31 28 36 DA 10 00
M0308 = 70 5D 75 5D 67 6C 40 5C    M04D8 = 2A 2A 2A 44 45 56 49 41
M0310 = 28 30 8E 20 70 F7 57 28    M04E0 = 54 49 4F 4E 2A 2A 2A 20
M0318 = 03 43 84 0B 74 52 65 28    M04E8 = 10 00 2A 2A 4C 49 4D 49
M0320 = 12 7A 6D 4C 10 17 28 36    M04F0 = 54 53 20 45 52 52 4F 52
M0328 = DA 48 21 10 84 02 1C 71    M04F8 = 2A 2A 28 31 30 20 48 50
M0330 = 86 2A 20 80 08 28 36 1D    M0500 = 28 37 E0 64 6B 70 CE 84
M0338 = 48 22 40 58 1B 90 FF 43    M0508 = 1E 4C 14 94 0B 28 12 52
M0340 = 29 07 3F 48 22 80 58 90    M0510 = 48 22 40 58 1B 90 FF 28
M0348 = E7 08 28 36 D2 52 68 20    M0518 = 10 E0 84 08 78 50 28 00
M0350 = 1F FC 5C 2A 20 E1 16 50    M0520 = 87 90 EE 28 10 99 28 0C
M0358 = 21 02 15 EC 5C 71 F0 94    M0528 = B5 94 04 29 09 A6 2A 20
M0360 = 04 29 03 DF 2A 20 E9 7F    M0530 = E1 11 20 71 50 28 02 F5
M0368 = 8A 2A 20 00 13 13 8E 64    M0538 = 10 15 11 20 3E 50 29 02
M0370 = 28 36 6A 2A 20 EA 7F 8A    M0540 = FA 10 16 11 20 38 50 28
M0378 = 2A 20 00 13 13 8E 63 28    M0548 = 02 FA 10 16 11 2A 20 E1
M0380 = 36 6A 6F 29 10 EC 5C 28    M0550 = 72 8A 84 2A 2A 20 E4 65
M0388 = 16 93 28 2E 30 28 04 58    M0558 = 6F 74 5E 70 5E 16 5E 16
M0390 = 2A 20 E7 7F 8A 2A 20 00    M0560 = 5C 67 20 58 5C 28 30 8E
M0398 = 13 13 8E 64 90 06 17 54    M0568 = 20 70 F7 57 28 03 43 84
M03A0 = 29 06 8D 28 36 6A 2A 20    M0570 = 0D 74 52 65 28 12 7A 6D
M03A8 = E8 7F 8A 2A 20 00 13 13    M0578 = 4E 10 17 4C 17 2A 20 E6
M03B0 = 8E 63 28 36 6A 6F 20 10    M0580 = 11 20 5E 50 28 02 FA 2A
M03B8 = EC 5C 28 16 93 28 02 D6    M0588 = 20 E1 71 8A 94 73 20 77
M03C0 = 28 16 12 2A 20 EB 62 28    M0590 = 67 6C 5C 2A 20 50 65 28
M03C8 = 36 6A 28 16 12 64 2A 20    M0598 = 36 6A 6F 4C 21 1F 5C 6C
M03D0 = 50 28 36 6A 6F 4C 21 1F    M05A0 = 20 F0 FC 5C 28 30 8E 20
M03D8 = 5C 28 16 93 29 04 18 2A    M05A8 = 70 F7 57 28 03 43 84 08
M03E0 = 20 00 0E 2A 20 50 64 28    M05B0 = 2A 20 50 65 28 36 3A 64
M03E8 = 36 6A 6F 4C 21 1F 5C 6C    M05B8 = 6A 20 F0 FC 5C 64 6A 7F
M03F0 = 20 F0 FC 5C 11 63 6B 4C    M05C0 = FC 54 20 3C 50 28 30 D6
M03F8 = 14 1F 56 0F 62 28 36 6A    M05C8 = 2A 20 54 44 13 13 8E 65
M0400 = 0E 63 10 28 36 6A 11 6D    M05D0 = 28 36 6A 28 30 8E 20 70
M0408 = 70 CD CC 82 03 84 07 28    M05D8 = F7 57 28 03 43 84 0F 2A
M0410 = 16 12 28 16 93 36 94 E4    M05E0 = 20 54 64 6A 7F FC 13 13
M0418 = 2A 20 84 16 50 2A 20 E6    M05E8 = 8E 65 28 36 3A 63 6B 4E
M0420 = 62 68 4C 21 3F 5C 40 8D    M05F0 = 14 50 64 7F FC E0 84 05
M0428 = 82 05 4C 22 80 5C 64 72    M05F8 = 4C 1F 5C 90 C1 29 05 2E
M0430 = 52 28 12 7A 82 12 6F 4C    M0600 = 2A 20 E7 11 76 50 28 02
M0438 = 14 94 0D 2A 20 E2 6E 4C    M0608 = F5 10 16 11 20 5B 50 28
M0440 = 1F 8D 92 04 8D 92 0F 62    M0610 = 02 F5 10 16 11 20 4F 50
M0448 = 68 4C 22 40 5C 73 50 28    M0618 = 28 02 F5 10 16 11 20 66
M0450 = 00 87 28 03 29 28 36 DA    M0620 = 50 28 02 F5 20 77 67 6C
M0458 = 74 50 6C 63 4C 62 5D 30    M0628 = 5C 2A 20 50 65 28 36 6A
M0460 = 94 FA 1C 74 50 6C 64 4C    M0630 = 6F 4C 21 1F 5C 6C 4C 21
M0468 = 65 5D 30 94 FA 1C 08 28    M0638 = F0 5C 28 30 8E 20 70 F7
M0470 = 36 D2 62 68 78 FC 64 74    M0640 = 57 28 03 43 84 08 2A 20
M0478 = 84 02 73 52 28 12 7A 28    M0648 = 50 65 28 36 3A 20 7C 67
M0480 = 36 43 28 04 63 28 30 8E    M0650 = 6C 5C 2A 20 EB 65 28 36
M0488 = 28 31 30 20 70 F7 57 62    M0658 = 6A 28 30 8E 20 70 F7 57
M0490 = 68 20 80 FC 14 22 84 50    M0660 = 28 03 43 84 08 2A 20 EB
M0498 = 28 37 E0 28 36 DA 08 28    M0668 = 65 28 36 3A 29 05 2E 2A
M04A0 = 36 D2 2A 20 D8 64 2C 28    M0670 = 20 80 28 36 26 70 1F 0C
```

```
M0678 = 73 52 40 0B 4C 53 90 04    M0848 = 5C 71 B6 27 22 1B 90 FF
M0680 = 29 07 34 41 08 43 5C 30    M0850 = 26 20 51 26 21 21 0F 50
M0688 = 31 32 94 EF 1C 7F F8 25    M0858 = 62 28 35 6A 63 6A 3C 94
M0690 = 07 94 04 29 08 50 26 25    M0860 = ED 62 6D 4D 50 4D 51 66
M0698 = 50 48 21 10 72 84 02 71    M0868 = 7F F0 2A 08 9A 0E 8E 16
M06A0 = F0 94 22 70 27 22 48 21    M0870 = 5D 67 40 14 0F 8E 16 5D
M06A8 = 10 84 09 48 21 20 84 04    M0878 = 7F F1 0F 8E 16 5D 41 14
M06B0 = 29 33 5F 70 27 21 64 69    M0880 = 0F 8E 16 5C 90 A8 63 6B
M06B8 = 4C 21 FA 5C 72 50 28 00    M0888 = 7F FC 25 09 84 0A 4C 1F
M06C0 = 87 29 31 EE 26 21 21 10    M0890 = 5C 28 35 AF 29 08 21 29
M06C8 = 94 04 1B 90 FF 26 20 51    M0898 = 09 02 3F 06 5B 4F 66 6D
M06D0 = 26 21 21 0F 50 26 21 21    M08A0 = 7D 07 7F 6F 77 7C 39 5E
M06D8 = 10 84 F0 41 21 F0 C0 84    M08A8 = 79 71 62 68 77 FC 25 06
M06E0 = 06 1F 94 18 71 50 70 27    M08B0 = 94 2F 7D 50 28 07 E5 28
M06E8 = 22 63 6B 7F FC 2A 30 E2    M08B8 = 09 0E 26 20 52 26 21 21
M06F0 = 8E 16 67 6C 5C 28 00 87    M08C0 = 0F 50 28 07 DB 42 14 50
M06F8 = 29 34 72 63 6F 4E 18 C0    M08C8 = 28 07 D8 7F F2 50 28 07
M0700 = 82 09 1F 92 08 4E 18 C1    M08D0 = DB 20 20 50 28 07 E5 26
M0708 = 92 06 6F 40 5E 41 5E 6D    M08D8 = 24 25 C0 84 DB 29 08 2D
M0710 = 40 18 CE 82 09 1F 92 0B    M08E0 = 28 0C E4 2A 20 D0 74 54
M0718 = 41 18 CC 92 06 6D 40 5E    M08E8 = 28 09 0E 26 20 53 26 21
M0720 = 41 5C 62 28 35 6A 63 6A    M08F0 = 21 0F 50 28 09 1B 43 14
M0728 = 3C 94 07 70 27 22 29 34    M08F8 = 50 28 09 1B 7F F3 50 28
M0730 = 9F 1B 90 FF 70 B6 2A 20    M0900 = 09 1B 20 20 17 34 94 E1
M0738 = 80 28 36 26 70 14 0C 1E    M0908 = 28 0C 31 29 08 2D 26 21
M0740 = 20 AE 88 64 69 4E 50 4C    M0910 = 21 10 94 FB 26 21 21 10
M0748 = 1F 25 0A 94 02 71 5C 51    M0918 = 84 FB 1C 20 30 C0 25 39
M0750 = 20 36 CC 0B 70 81 A0 21    M0920 = 81 03 24 07 17 1C 08 2A
M0758 = 20 E1 80 4C 81 20 10 F7    M0928 = 20 96 28 36 1D 28 0C AE
M0760 = 94 04 1D 1B 1C 70 27 24    M0930 = 7F F8 25 01 94 06 2A 0D
M0768 = A0 21 0F B0 70 C0 94 04    M0938 = 84 90 0F 26 25 21 01 94
M0770 = 29 2E EB 29 36 ED 08 2A    M0940 = 06 2A 0D C6 90 04 2A 0D
M0778 = 20 D0 20 16 52 62 68 77    M0948 = D3 28 0D 11 28 0C 31 28
M0780 = FC 25 06 94 08 16 50 28    M0950 = 0C AE 63 6B 20 F0 FC 5C
M0788 = 07 E5 90 1E 20 20 27 25    M0958 = 28 0C E4 2A 20 D4 2C 63
M0790 = 28 07 BB 7A 54 16 18 55    M0960 = 68 7F FC 50 28 0C F5 28
M0798 = 21 01 13 15 27 25 28 07    M0968 = 35 76 64 28 36 6A 2A 20
M07A0 = BB 34 84 06 45 12 55 90    M0970 = D6 2C 28 0D 22 28 0C 31
M07A8 = F0 42 25 06 94 04 2A 07    M0978 = 63 6B 7F FC 50 4C 14 E0
M07B0 = B5 32 94 CA 0C 0D 0A 00    M0980 = 84 06 4C 1F 5C 90 D2 7F
M07B8 = 00 00 00 2C 2A 07 D1 77    M0988 = F8 25 03 84 10 28 0C AE
M07C0 = FC 24 FF 13 3E 16 50 16    M0990 = 28 0C E4 2A 0D EA 28 0D
M07C8 = 51 2C 31 94 FE 30 94 FB    M0998 = 11 28 0C 31 28 0D 82 2A
M07D0 = 1C 04 81 02 41 01 47 01    M09A0 = 20 96 28 36 26 0C 28 0B
M07D8 = 1D 01 09 20 30 C0 25 39    M09A8 = 73 64 6B 70 CC 84 40 28
M07E0 = 31 03 24 07 50 20 20 27    M09B0 = 0C E4 2A 0D F5 28 0D 11
M07E8 = 25 A4 A4 A0 7A 51 40 18    M09B8 = 2C 16 2C 64 6B 4C 14 94
M07F0 = 50 21 01 13 15 27 25 2B    M09C0 = 06 2C 16 2C 90 05 50 28
M07F8 = A4 31 94 06 40 12 50 90    M09C8 = 0C F5 7F FE 50 28 0C F5
M0800 = F1 1C 20 8D 50 28 37 E0    M09D0 = 28 0D 05 4C 14 50 28 0C
M0808 = 67 6C 76 5D 70 5D 5D 20    M09D8 = F5 28 0C 31 64 6B 4C 14
M0810 = 71 5C 28 35 81 63 6B 4C    M09E0 = 84 0D 28 0B AD 28 0B FF
M0818 = 21 F0 5C 2A 08 86 28 36    M09E8 = 28 0C 31 28 0C AE 28 0C
M0820 = E2 63 6B 7F FC 2A 08 9A    M09F0 = E4 2A 0F 17 28 0D 11 2A
M0828 = 8E 67 6D 16 5C 26 25 21    M09F8 = 20 E1 73 8A 50 28 0C F5
M0830 = 02 15 13 27 21 26 24 25    M0A00 = 28 0C 31 2A 20 E1 71 8A
M0838 = C0 94 04 29 08 AA 63 6A    M0A08 = 2A 0F 21 84 04 2A 0F 33
M0840 = 20 10 5C 62 6D 70 5D 5D    M0A10 = 28 0D 11 28 0C 31 2A 20
```

```
M0A18 = E1 72 8A 84 30 2A 0F 45    M0BE8 = 28 0D 11 2C 16 2C 64 6B
M0A20 = 28 0D 11 2A 20 DB 2C 2A    M0BF0 = 4C 14 50 28 0C F5 7F FC
M0A28 = 20 E4 16 51 14 50 28 0C    M0BF8 = 50 28 0C F5 29 0C 32 08
M0A30 = F5 7F F1 50 28 0C F5 28    M0C00 = 28 0C E4 64 6B 4C 14 84
M0A38 = 0D 05 16 14 50 28 0C F5    M0C08 = 17 6A 4C 14 24 FF 15 12
M0A40 = 28 0C 31 2A 0F 75 28 0D    M0C10 = 2A 0E CF 8E 2C 2A 20 D0
M0A48 = 11 28 0C 31 2A 0F 87 28    M0C18 = 2C 78 50 28 0D 1A 0C 2A
M0A50 = 0D 11 2A 20 E2 16 51 14    M0C20 = 0D AC 28 0D 11 2C 16 2C
M0A58 = 50 28 0C F5 7F F1 50 28    M0C28 = 64 6A 4C 14 50 28 0C F5
M0A60 = 0C F5 28 0C 31 2A 0F 97    M0C30 = 0C 08 28 0C B5 84 02 0C
M0A68 = 28 0D 11 2A 20 E3 16 51    M0C38 = 70 27 25 A0 21 10 84 3A
M0A70 = 14 50 28 0C F5 7F F1 50    M0C40 = 70 B6 27 22 27 26 47 21
M0A78 = 28 0C F5 28 0C 31 2A 0F    M0C48 = EF 57 2A 20 D0 20 11 56
M0A80 = 57 28 0D 11 2A 20 E6 16    M0C50 = 71 BE A0 21 0F 22 20 B0
M0A88 = 51 14 50 28 0C F5 7F F1    M0C58 = 70 52 53 1B 32 94 FE 33
M0A90 = 50 28 0C F5 28 0C 31 2A    M0C60 = 94 FB 1A 70 BE A0 21 0F
M0A98 = 20 E1 71 9A 84 53 2A 0F    M0C68 = B0 20 14 52 53 1B 32 94
M0AA0 = 67 28 0D 11 2A 20 E7 74    M0C70 = FE 33 94 FB 1A 47 22 10
M0AA8 = 51 7F 8A 50 28 0C F5 31    M0C78 = 57 7F F8 25 07 94 02 0C
M0AB0 = 94 F8 28 0C 31 28 0C E4    M0C80 = 62 68 77 FC 84 FA 25 07
M0AB8 = 2A 0F A7 28 0D 11 2A 20    M0C88 = 84 F6 29 07 77 0C A0 21
M0AC0 = 50 64 28 36 6A 6F 4C 21    M0C90 = 2F 50 20 20 B0 A1 51 16
M0AC8 = 1F 5C 2A 20 D9 2C 28 0D    M0C98 = 81 20 2C B0 A4 A4 A4 20
M0AD0 = 22 28 0C 31 28 0C E4 2A    M0CA0 = 20 80 A4 A4 A4 41 81 40
M0AD8 = 0F AE 28 0D 11 2A 20 EB    M0CA8 = 80 36 94 AD 90 85 03 28
M0AE0 = 64 28 36 6A 2A 20 D9 2C    M0CB0 = 0C E4 29 0C 32 0A 50 62
M0AE8 = 28 0D 22 28 0C 31 90 4F    M0CB8 = 68 77 FC 59 40 0B 84 09
M0AF0 = 64 6A 20 F0 FC 24 0A 5C    M0CC0 = 49 25 07 84 09 14 14 1C
M0AF8 = 64 6A 7F FC 1F 25 0B 94    M0CC8 = A0 21 10 94 03 1F 1C A0
M0B00 = 02 70 50 13 13 2A 20 50    M0CD0 = 21 0F 50 7C B0 A4 A4 A4
M0B08 = 8E 28 36 6A 28 0C E4 7F    M0CD8 = A0 21 10 40 B0 70 94 03
M0B10 = 6A FC 50 2A 20 D4 2C 28    M0CE0 = 13 1C 14 1C 2A 20 D0 20
M0B18 = 0C F5 2C 16 2C 28 0D 22    M0CE8 = 10 50 20 20 17 30 94 FD
M0B20 = 28 0C 31 63 6B 4E 14 50    M0CF0 = 2A 20 D0 2C 1C 20 30 C0
M0B28 = 64 7F FC E0 84 11 7F FC    M0CF8 = 25 39 81 03 24 07 2C 17
M0B30 = 25 0A 94 06 20 F0 FC 90    M0D00 = 2C 1C 40 90 FA 20 2E 90
M0B38 = 03 4C 1F 5C 90 6B 28 0C    M0D08 = F6 20 2D 90 F2 20 25 90
M0B40 = AE 28 0C E4 2A 0E 02 28    M0D10 = EE 16 50 16 2C 2A 20 D0
M0B48 = 0D 11 2C 16 2C 62 58 78    M0D18 = 8E 2C 16 2C 17 2C 30 94
M0B50 = FC 84 0B 28 0D 05 79 50    M0D20 = FA 1C 08 6F 4C 21 10 20
M0B58 = 28 0C F5 90 09 70 50 28    M0D28 = 2D 94 03 20 20 50 28 0D
M0B60 = 0C F5 28 0D 05 71 50 28    M0D30 = 02 7F FE 25 05 82 02 75
M0B68 = 0C F5 28 0C 31 28 0D 82    M0D38 = 54 52 24 FF 51 13 24 05
M0B70 = 29 05 2E 08 00 06 01 07    M0D40 = 53 70 C2 94 06 70 51 56
M0B78 = 28 0C AE 20 80 56 71 55    M0D48 = 90 2C 70 56 71 F6 94 05
M0B80 = 28 15 E9 28 09 9B 28 0C    M0D50 = 4C 14 90 03 7F FE 50 36
M0B88 = 31 20 A1 56 71 55 28 15    M0D58 = 70 C1 84 10 70 C0 94 0A
M0B90 = E9 28 0B 9B 28 0C 31 28    M0D60 = 31 20 20 50 28 0D 02 90
M0B98 = 0C AE 0D 20 10 50 2A 20    M0D68 = 06 70 51 28 0C F5 32 94
M0BA0 = D0 2C 2A 20 86 16 2C 17    M0D70 = DC 70 C3 84 0D 20 2E 50
M0BA8 = 2C 30 94 FA 1C 08 64 6B    M0D78 = 28 0D 02 43 52 70 53 90
M0BB0 = 4C 25 21 92 2E 14 84 2B    M0D80 = CC 0C 08 00 06 01 07 28
M0BB8 = 2A 0E 0F 11 24 FF 13 50    M0D88 = 0C AE 28 0C AE 2A 20 D0
M0BC0 = 13 13 C0 50 7F FC C0 50    M0D90 = 20 10 50 20 3D 17 30 94
M0BC8 = 15 51 40 14 50 41 CB 5B    M0D98 = FD 28 0C 31 28 0C AE 28
M0BD0 = 40 19 CA 5A 20 10 50 2A    M0DA0 = 0C AE 0D 07 03 50 52 4F
M0BD8 = 20 D0 2C 10 28 0D 1A 29    M0DA8 = 44 55 43 54 06 00 43 4F
M0BE0 = 0C 32 28 0C E4 2A 0D A3    M0DB0 = 4E 53 54 2E 10 00 43 41
```

```
M0DB8 = 4C 49 42 52 41 54 49 4F    M0F88 = 00 55 50 50 45 52 20 4C
M0DC0 = 4E 20 44 41 54 41 10 00    M0F90 = 49 4D 49 54 20 3D 20 0E
M0DC8 = 52 41 57 20 53 41 4D 50    M0F98 = 00 4C 4F 57 45 52 20 4C
M0DD0 = 4C 45 20 44 41 54 41 20    M0FA0 = 49 4D 49 54 20 3D 20 05
M0DD8 = 10 00 20 52 45 46 45 52    M0FA8 = 04 4B 28 41 29 3A 05 04
M0DE0 = 45 4E 43 45 20 44 41 54    M0FB0 = 4B 28 42 29 3A 20 8A 50
M0DE8 = 41 20 09 00 41 4E 41 4C    M0FB8 = 28 37 E0 20 8D 50 28 37
M0DF0 = 59 53 49 53 3A 08 00 43    M0FC0 = E0 20 41 50 28 37 E0 20
M0DF8 = 41 4C 49 42 52 41 54 49    M0FC8 = 87 50 28 37 E0 67 6D 70
M0E00 = 4F 4E 08 00 52 45 53 4F    M0FD0 = 5D 5D 5C CA 84 1B 2A 20
M0E08 = 4C 55 54 49 4F 4E 3A 20    M0FD8 = 86 20 10 50 20 20 17 30
M0E10 = 20 20 20 20 20 43 4F 52    M0FE0 = 94 FD 20 80 56 71 55 28
M0E18 = 4E 20 20 20 20 20 20 20    M0FE8 = 15 F6 20 A1 56 28 15 F6
M0E20 = 20 20 20 53 4F 59 42 45    M0FF0 = 28 06 73 20 80 56 71 55
M0E28 = 41 4E 53 20 20 20 20 48    M0FF8 = 28 15 E9 62 6B 70 5C 71
M0E30 = 52 44 20 52 20 57 4E 54    M1000 = 2A 20 84 17 20 7D 67 6C
M0E38 = 52 20 57 48 45 41 54 48    M1008 = 5C 63 6A 71 5C 48 22 80
M0E40 = 52 44 20 52 20 53 50 52    M1010 = 58 20 88 50 28 37 E0 2A
M0E48 = 47 20 57 48 45 41 54 53    M1018 = 10 8D 28 36 E2 20 3E 50
M0E50 = 46 54 20 52 20 57 4E 54    M1020 = 63 6A 4C 14 51 7F FC 54
M0E58 = 52 20 57 48 45 41 54 20    M1028 = 28 30 D6 41 54 28 30 D6
M0E60 = 20 20 20 20 20 4F 41 54    M1030 = 1B 90 FF 74 52 65 28 12
M0E68 = 53 20 20 20 20 20 20 20    M1038 = 7A 6D 4C 21 70 12 50 77
M0E70 = 20 53 4F 59 42 45 41 4E    M1040 = FC E0 50 25 19 92 04 24
M0E78 = 20 4D 45 41 4C 20 20 20    M1048 = 40 50 2A 20 84 16 8E 40
M0E80 = 20 20 20 20 42 41 52 4C    M1050 = 17 62 6B 70 CC 20 80 84
M0E88 = 45 59 20 20 20 20 20 20    M1058 = 03 20 A1 56 71 55 28 15
M0E90 = 20 20 20 20 20 52 59 45    M1060 = F6 28 31 13 63 6A 20 67
M0E98 = 20 20 20 20 20 20 20 20    M1068 = DC 5C 2A 20 84 16 2A 20
M0EA0 = 20 20 54 52 49 54 49 43    M1070 = 84 1F 25 11 84 04 17 90
M0EA8 = 41 4C 45 20 20 20 20 20    M1078 = 95 62 6B 70 CC 94 18 71
M0EB0 = 20 20 20 53 4F 52 47 48    M1080 = 5C 17 20 A1 56 71 55 28
M0EB8 = 55 4D 20 20 20 20 20 53    M1088 = 15 E9 29 10 0D 2A 20 84
M0EC0 = 55 4E 46 4C 4F 57 45 52    M1090 = 16 8E 16 50 90 CF 29 0F
M0EC8 = 20 53 45 45 44 53 20 4D    M1098 = F0 08 2A 20 99 28 36 1D
M0ED0 = 4F 49 53 54 55 52 45 50    M10A0 = 2A 20 E0 20 20 50 70 51
M0ED8 = 52 4F 54 45 49 4E 20 4F    M10A8 = 45 89 46 88 A4 17 C1 51
M0EE0 = 49 4C 2F 46 41 54 20 53    M10B0 = 46 1F 56 30 94 F5 70 89
M0EE8 = 54 41 52 43 48 20 20 46    M10B8 = 20 AB C1 84 0A 20 11 50
M0EF0 = 49 42 45 52 20 20 20 41    M10C0 = 28 00 87 1B 90 FF 28 10
M0EF8 = 53 48 20 20 20 20 20 43    M10C8 = D2 2A 20 50 28 15 AC 29
M0F00 = 4F 4E 53 54 2E 20 37 43    M10D0 = 12 A7 62 6B 4C 24 FF 13
M0F08 = 4F 4E 53 54 2E 20 38 43    M10D8 = 13 56 C6 56 70 19 55 1C
M0F10 = 4F 4E 53 54 2E 20 39 08    M10E0 = 70 56 71 54 72 55 64 45
M0F18 = 03 46 4F 52 4D 41 54 23    M10E8 = 89 46 B8 A4 18 1F 6B CE
M0F20 = 3D 10 00 20 4D 55 4C 54    M10F0 = 94 17 46 1F B8 A4 14 18
M0F28 = 49 2D 54 45 52 4D 20 45    M10F8 = 1F 50 4C 14 C0 94 0A 62
M0F30 = 51 2E 20 10 00 53 49 4E    M1100 = 69 45 5D 46 5D 44 5C 1C
M0F38 = 47 4C 45 20 54 45 52 4D    M1108 = 71 C4 54 46 24 20 56 92
M0F40 = 20 45 51 2E 20 10 00 41    M1110 = D7 71 F5 94 06 45 1F 55
M0F48 = 4C 53 4F 20 52 45 41 44    M1118 = 90 CE 45 25 03 94 05 74
M0F50 = 53 20 20 20 20 20 25 0E    M1120 = 55 90 C5 25 05 94 04 73
M0F58 = 00 4D 41 58 20 44 45 56    M1128 = 90 F7 1C 20 4B 50 28 37
M0F60 = 49 41 54 49 4F 4E 3D 0C    M1130 = E0 64 6A 4D 14 94 0B 28
M0F68 = 00 52 31 2C 52 32 2C 52    M1138 = 12 52 48 22 40 58 1B 90
M0F70 = 33 2C 52 34 3A 10 00 20    M1140 = FF 70 CC 84 F3 28 19 E0
M0F78 = 4D 4F 49 53 54 55 52 45    M1148 = 84 08 78 50 28 00 87 90
M0F80 = 20 42 41 53 49 53 20 0E    M1150 = EA 48 22 C0 58 2A 11 82
```

```
M1158 = 28 36 E2 28 10 D2 2A 20      M1328 = 40 13 13 8E 70 17 17 17
M1160 = 50 28 15 AC 2A 20 53 20      M1330 = 75 17 31 94 F8 73 52 77
M1168 = 80 8A 50 28 31 13 66 6F      M1338 = 53 7A 54 2A 20 E7 2C 2A
M1170 = 70 C0 20 3F 94 03 20 BF      M1340 = 20 54 11 70 88 94 13 88
M1178 = 5D 57 84 04 20 BF 5C 1B      M1348 = 94 1C 88 94 0D C2 84 0A
M1180 = 90 FF 2A 20 53 20 80 8C      M1350 = 32 16 2C 20 FF 17 2C 90
M1188 = 2A 20 53 17 2A 20 50 28      M1358 = 34 70 C3 94 0A 20 10 50
M1190 = 10 D2 28 15 CD 29 11 51      M1360 = 28 00 87 18 90 FF 10 16
M1198 = 2A 20 50 63 28 36 6A 6F      M1368 = 14 51 16 50 15 E1 2C 17
M11A0 = 4C 21 1F 5C 28 14 EB 28      M1370 = 2C 40 14 51 16 50 15 E1
M11A8 = 16 93 2A 20 53 16 21 80      M1378 = 2C 17 2C 40 14 51 16 50
M11B0 = 64 6F CC 5C 2A 20 50 28      M1380 = 21 10 E1 51 40 15 13 E1
M11B8 = 36 3A 90 D1 20 48 50 28      M1388 = 2C 17 2C 33 34 94 84 20
M11C0 = 37 E0 20 8A 50 28 37 E0      M1390 = 1F 50 70 2A 20 E0 88 30
M11C8 = 48 22 40 58 64 68 70 CE      M1398 = 94 FD 18 1F 24 55 17 1C
M11D0 = 94 07 28 12 52 1B 90 FF      M13A0 = 08 2A 20 85 40 59 70 53
M11D8 = 4C 14 84 F7 79 55 20 E0      M13A8 = 52 54 45 5A 46 5B 4B B8
M11E0 = 56 20 30 54 45 B9 46 B8      M13B0 = 7C CA 15 B9 72 85 70 B5
M11E8 = A4 18 84 29 34 46 24 E0      M13B8 = 74 85 A4 51 70 85 41 C3
M11F0 = 56 82 F2 71 F5 84 07 45      M13C0 = 53 71 F9 41 84 06 15 E4
M11F8 = 24 FF 55 90 E8 45 25 04      M13C8 = 17 90 02 54 48 18 88 7C
M1200 = 94 05 73 55 90 DF 81 04      M13D0 = CA 23 03 15 B9 72 B5 70
M1208 = 75 90 F9 20 13 50 28 00      M13D8 = 85 74 85 A4 51 70 85 41
M1210 = 87 1B 90 FF 62 69 45 5D      M13E0 = C2 52 48 1F 58 4A 19 5A
M1218 = 46 5D 44 5C 2A 12 25 28      M13E8 = 39 94 C4 7F F3 25 05 94
M1220 = 36 E2 1B 90 FF 2A 20 E0      M13F0 = 08 7F F2 25 05 94 1A 0C
M1228 = 64 68 4E 17 20 F0 FC 50      M13F8 = 7F F3 25 05 84 0A 20 12
M1230 = 7F 8A E0 2A 20 E1 17 28      M1400 = 50 28 00 87 18 90 FF A8
M1238 = 13 03 62 69 4D 55 4C 56      M1408 = 56 A9 14 21 03 55 90 92
M1240 = 28 14 9A 28 10 D2 2A 20      M1410 = 40 59 46 88 7C C5 15 B9
M1248 = 50 28 15 CD 28 12 5E 1B      M1418 = 72 B5 70 B5 74 B5 A4 54
M1250 = 90 FF 08 20 88 50 28 37      M1420 = 70 B5 46 18 56 73 E5 55
M1258 = E0 2A 12 9D 90 05 08 2A      M1428 = 28 14 3B 46 18 56 73 E5
M1260 = 12 A2 20 3B 50 75 51 40      M1430 = 55 46 1F 56 45 19 55 39
M1268 = 0B 16 5C 30 31 94 F9 47      M1438 = 94 D9 0C 70 27 25 46 B8
M1270 = 21 70 57 67 6F 4C 21 7F      M1440 = 45 15 B9 72 B5 74 B5 7C
M1278 = 5C 0C 08 28 17 01 7F FC      M1448 = B5 74 B5 70 B5 72 52 20
M1280 = 18 1F C2 81 04 24 FF 0C      M1450 = 90 53 72 B5 70 B5 33 94
M1288 = 7F FC 18 1F C2 84 0D 4C      M1458 = FA 32 94 F7 7C C5 15 B9
M1290 = 51 70 5C 28 16 86 41 1F      M1460 = 74 B5 70 B5 78 C5 15 B9
M1298 = 5C 90 EE 18 0C 73 50 5C      M1468 = 44 84 72 B5 74 B5 7C B5
M12A0 = 5E D3 5E 5C 54 58 B0 2A      M1470 = 74 B5 70 B5 20 28 53 72
M12A8 = 20 E1 71 8A 84 17 2A 20      M1478 = B5 70 B5 33 94 FA 70 B4
M12B0 = 53 20 80 8A 14 50 62 68      M1480 = 7C C5 15 B9 74 B5 A4 53
M12B8 = 20 F7 FC E0 5C 2A 20 99      M1488 = 70 B5 43 E4 21 0F 84 0A
M12C0 = 28 36 26 0C 2A 20 54 2C      M1490 = 20 14 50 28 00 87 18 90
M12C8 = 2A 20 E7 7A 52 16 25 FF      M1498 = FF 1C 70 27 25 08 2A 20
M12D0 = 94 0B 2C 70 17 17 17 75      M14A0 = E0 20 20 50 16 51 72 52
M12D8 = 17 2C 90 23 50 2C 15 17      M14A8 = 46 B8 45 B9 28 14 CD A4
M12E0 = 40 14 51 2C 16 50 2C 15      M14B0 = E1 84 0F 32 94 F7 70 B9
M12E8 = E1 17 40 14 51 2C 16 50      M14B8 = 20 14 50 28 00 87 18 90
M12F0 = 2C 15 E1 17 20 10 F0 51      M14C0 = FF 28 14 CD 70 89 46 1F
M12F8 = 40 14 12 E1 17 2C 32 94      M14C8 = 56 30 94 D9 0C 20 19 53
M1300 = CD 90 AC 2A 20 E1 71 8A      M14D0 = 71 85 41 84 20 85 54 73
M1308 = 84 0F 2A 20 EF 20 10 50      M14D8 = 85 71 85 34 94 FA 20 64
M1310 = 70 17 30 94 FD 29 13 8F      M14E0 = 54 34 94 FE 33 94 EE 70
M1318 = 63 6B 4C 14 25 09 84 16      M14E8 = B4 85 1C 74 50 6C 65 4C
M1320 = 50 18 24 0A 51 2A 20 58      M14F0 = 64 5D 30 94 FA 1C 08 28
```

```
M14F8 = 36 D2 72 50 28 13 A0 2A    M16C8 = 14 94 18 28 17 28 84 05
M1500 = 20 85 16 53 6B 21 F0 5C    M16D0 = 64 28 16 86 42 1F 52 40
M1508 = 28 36 DA 08 28 36 D2 63    M16D8 = 21 10 C3 5C 0C 40 14 84
M1510 = 6B 4C 14 18 24 06 54 28    M16E0 = 04 63 90 02 64 28 17 1E
M1518 = 15 23 4C 14 54 28 15 23    M16E8 = 70 C1 84 07 28 17 20 70
M1520 = 28 36 DA 08 28 14 3B 46    M16F0 = 90 0D 28 17 20 94 05 54
M1528 = 18 56 73 E5 55 28 14 3B    M16F8 = 28 17 2E 71 EC 15 C2 5C
M1530 = 46 18 56 73 E5 55 46 1F    M1700 = 09 6E 20 F0 FD 94 19 4C
M1538 = 56 45 19 55 0C 70 51 16    M1708 = 15 84 15 3E 73 50 4C 15
M1540 = 52 14 C1 51 7F F2 C1 51    M1710 = 5E 4D 14 EC 5E 30 94 F7
M1548 = 30 94 F5 7F F1 18 24 06    M1718 = 4D 4C 21 F0 5C 90 E3 1C
M1550 = 21 0F 51 1C 08 28 36 D2    M1720 = 6C 63 4C 24 66 64 DC 5D
M1558 = 76 50 28 13 A0 2A 20 85    M1728 = 4C 19 5C 8F F5 1C 71 51
M1560 = 6C 28 36 67 6C 4C 21 F0    M1730 = 6C 70 CC 94 04 C1 94 06
M1568 = 5C 28 36 DA 08 28 36 D2    M1738 = 13 D1 5C 70 51 4D 8F F2
M1570 = 6C 4C 21 F0 5C 2A 20 85    M1740 = 1C 08 70 55 45 1F 55 41
M1578 = 28 36 3A 2A 20 85 73 50    M1748 = C1 51 40 19 1E C0 50 82
M1580 = 28 15 3D 2A 20 85 16 E1    M1750 = 04 1D 92 F1 62 5C 73 5D
M1588 = 2A 20 85 17 2A 20 85 76    M1758 = 5D 45 15 5D 71 5C 41 53
M1590 = 50 71 F0 16 84 04 14 90    M1760 = 40 52 71 56 28 17 D2 20
M1598 = 03 21 0F 54 28 15 23 71    M1768 = 80 E0 50 73 C2 94 04 C3
M15A0 = F0 94 04 20 FF 8E 30 94    M1770 = 84 4C 41 18 1F 1E C3 55
M15A8 = E9 28 36 DA 08 0E 28 36    M1778 = 92 02 1E 40 18 1D 19 1E
M15B0 = D2 78 50 28 13 A0 0F 2C    M1780 = C2 54 82 0C 1D 82 09 28
M15B8 = 2A 20 85 74 50 16 2C 17    M1788 = 17 D2 46 1F 56 90 DD 44
M15C0 = 2C 30 94 FA 0F 16 21 F0    M1790 = 50 52 45 51 53 28 17 D2
M15C8 = 0F 17 28 36 DA 08 0E 28    M1798 = 20 80 E0 50 46 55 35 84
M15D0 = 36 D2 0F 16 21 F0 0F 17    M17A0 = 06 28 17 D2 90 F9 2A 2E
M15D8 = 0F 74 50 28 15 3D 0F 18    M17A8 = 00 46 24 FF 55 C5 C5 8E
M15E0 = E1 0F 17 0F 78 50 29 15    M17B0 = 6C 16 24 66 DC 5D 4C 19
M15E8 = 91 08 28 36 D2 20 21 50    M17B8 = 5C 8F F7 90 AF 63 6C 70
M15F0 = 28 13 A0 28 36 DA 08 18    M17C0 = 5D 20 50 5D 20 12 5D 73
M15F8 = 36 D2 2A 20 86 20 10 50    M17C8 = 5C 62 71 5C 28 17 01 29
M1600 = 28 15 3D 2A 20 85 41 15    M17D0 = 16 13 41 12 51 40 15 13
M1608 = 17 2A 20 85 20 21 50 29    M17D8 = 13 13 E1 51 40 12 50 1C
M1610 = 15 91 08 62 28 17 01 63    M17E0 = 03 21 30 84 05 67 28 15
M1618 = 28 17 01 66 6F 4C 63 69    M17E8 = 90 03 59 1D 60 28 20 87
M1620 = 5C 66 6C 70 5D 8F FE 5C    M17F0 = 51 28 20 87 0C 48 59 58
M1628 = 63 4C 62 CC 21 1F 52 6C    M17F8 = 67 4C 18 1F 66 CD 94 05
M1630 = 71 51 8F 03 90 2E 70 C1    M2E00 = 00 00 90 96 84 95 35 07
M1638 = 84 06 4C 21 0F 90 03 4D    M2E08 = 98 89 06 99 20 54 99 28
M1640 = 14 50 71 E1 51 0A 53 66    M2E10 = 77 99 68 88 99 35 94 99
M1648 = 28 16 86 70 C0 94 05 43    M2E18 = 18 97 99 59 98 99 30 99
M1650 = 0B 90 E0 6C 63 4C 24 66    M2E20 = 99 65 99 99 82 99 99 91
M1658 = 66 DC 5D 4C 19 5C 8F F5    M2E28 = 99 99 96 99 99 98 99 99
M1660 = 30 90 E9 66 70 CC 94 08    M2E30 = 08 64 6F 72 CC 5C 28 17
M1668 = 7F F2 84 04 32 90 04 28    M2E38 = 01 6E 4D 12 94 05 28 02
M1670 = 16 86 6C 66 4C 63 5D 8F    M2E40 = D6 0C 4C 56 70 5C 62 5C
M1678 = FB 42 5C 63 69 4C 66 6F    M2E48 = 63 6C 70 5D 8F FE 51 75
M1680 = 5C 63 09 29 17 01 6C 4C    M2E50 = 50 70 52 6C 63 4C 62 5D
M1688 = 14 5D 4E 15 EC 5D 8F F8    M2E58 = 8F FB 6C 18 64 20 66 CC
M1690 = 70 5C 1C 08 63 28 17 01    M2E60 = 62 DC 5D 4C 19 5C 8F F5
M1698 = 64 28 17 01 6F 4C 51 70    M2E68 = 70 5C 94 0D 6C 62 4C 63
M16A0 = 5C 63 4C 50 70 5C 7F F1    M2E70 = 5D 8F FB 71 C2 52 90 E3
M16A8 = 53 7F F0 52 18 1F C3 84    M2E78 = 40 12 24 34 0B 41 18 51
M16B0 = 16 91 0A 63 28 16 86 42    M2E80 = 42 84 05 15 5C 90 03 EC
M16B8 = 1F 52 90 F1 64 28 16 86    M2E88 = 5C 64 28 16 86 30 82 C2
M16C0 = 43 1F 53 42 90 E7 41 E0    M2E90 = 28 2E 86 46 21 10 52 7F
```

```
M2E38 = F6 25 33 92 09 18 24 04    M3068 = 69 4C 21 32 5E 70 27 22
M2E40 = 22 43 FF 5C 0C 51 6F 70    M3070 = 62 77 FC 84 07 20 8B 50
M2E48 = 5C 7F F6 24 FD 52 00 06    M3078 = 28 37 E0 0D 00 AC 00 C2
M2E50 = 31 07 28 12 7A 6F 20 10    M3080 = 04 FA 00 C9 11 2B 11 BC
M2E58 = F6 5C 0D 74 50 6C 66 4C    M3088 = 0F 85 08 02 00 D3 08 20
M2E60 = 63 5D 30 94 FA 1C 64 6E    M3090 = 37 50 20 2C 51 0B 75 53
M2E68 = 4D 51 70 CC 84 05 20 99    M3098 = 71 F3 94 06 4C 21 0F 90
M2E70 = 90 11 41 12 12 51 14 2A    M30A0 = 03 4D 14 54 0A 51 28 30
M2E78 = 2E E7 8E 16 50 7F F1 51    M30A8 = D6 41 08 33 94 EB 4C 51
M2E80 = 40 D1 2A 20 84 17 1C 66    M30B0 = 21 10 12 15 52 57 6F 20
M2E88 = 7C 98 AE 63 68 26 25 70    M30B8 = 7F FC E2 5C 7F F1 18 24
M2E90 = 81 02 71 5C 21 01 84 0F    M30C0 = 06 84 08 24 36 0B 4C 22
M2E98 = EC 5C 26 25 18 21 80 14    M30C8 = 80 5C 67 6B 4C 25 3F 94
M2F00 = 22 44 50 28 37 E0 26 25    M30D0 = 05 70 5E 9F F8 0C 40 0B
M2F08 = 21 04 84 0A 7F F8 84 06    M30D8 = 1F 50 2A 30 E2 44 8E 16
M2F10 = 70 51 29 30 4F 47 21 30    M30E0 = 5D 1C 3F 06 5B 4F 66 5D
M2F18 = 23 30 94 11 20 40 F7 94    M30E8 = 7D 07 7F 6F 00 64 59 4C
M2F20 = 0F 26 24 94 08 28 30 ED    M30F0 = 22 20 5C 2A 20 9F 20 64
M2F28 = 47 22 40 57 18 90 FF 2A    M30F8 = 17 47 21 9F 57 1C 64 69
M2F30 = 2F 53 7F 50 26 24 84 F5    M3100 = 4C 22 10 5C 2A 20 A0 20
M2F38 = 8D 84 06 30 82 FB 90 ED    M3108 = 0A 17 20 10 27 25 1C 74
M2F40 = 28 30 ED 40 51 24 F6 92    M3110 = F7 94 1D 66 6F 70 5D 67
M2F48 = 27 13 2A 2F 63 8E 16 06    M3118 = 5D 5D 5D 5D 6F 20 7F FC
M2F50 = 16 07 0D 41 C0 48 42 12    M3120 = 5C 20 70 F7 22 0C 57 65
M2F58 = 06 11 21 05 90 A0 84 13    M3128 = 6C 70 5D 5D 5D 75 5D 1C
M2F60 = 28 0C 22 2F AF 2F C0 31    M3130 = 08 20 3D 50 64 6A 4D 14
M2F68 = CB 2F D7 31 72 2F CE 72    M3138 = 51 4C 14 53 7F FC 52 70
M2F70 = F7 84 04 1B 90 FF 28 30    M3140 = C1 94 02 7A 54 28 30 D6
M2F78 = FE 28 31 0F 20 77 F7 57    M3148 = 42 54 28 30 D6 70 C3 94
M2F80 = 65 6E 70 CC 84 06 47 22    M3150 = 02 7A 54 28 30 D6 70 C1
M2F88 = 02 57 4C 15 5E 4D 14 EC    M3158 = 84 06 6D 4C 22 80 5C 20
M2F90 = 5E 4C 15 5E 4D 14 EC 5E    M3160 = 49 50 28 37 E0 70 C1 20
M2F98 = 41 15 5C 71 F7 84 08 6F    M3168 = 87 84 03 20 8F 50 28 37
M2FA0 = 3C 7F FC 94 05 47 22 02    M3170 = E0 0C 47 15 91 04 13 91
M2FA8 = 57 28 30 8E 18 90 FF 73    M3178 = 04 1B 90 FF 28 30 FE 74
M2FB0 = F7 94 FA 28 30 FE 28 31    M3180 = 52 65 28 12 7A 6C 4D 14
M2FB8 = 0F 47 22 81 21 F7 90 E9    M3188 = 52 4C 51 28 31 13 64 6A
M2FC0 = 28 30 FE 28 31 0F 65 6F    M3190 = 42 15 52 7F FC E2 5D 70
M2FC8 = 20 10 EC 5C 90 DC 29 30    M3198 = C2 84 05 70 C1 84 03 41
M2FD0 = FE 28 31 13 1B 90 FF 47    M31A0 = 5C 28 31 30 20 40 F8 84
M2FD8 = 15 91 D2 13 81 CF 28 30    M31A8 = D1 20 BF F8 58 20 80 50
M2FE0 = FE 70 C7 81 10 48 21 4F    M31B0 = 28 37 E0 7F F8 25 02 94
M2FE8 = 25 40 94 09 62 68 78 EC    M31B8 = 04 29 04 FA 91 04 29 01
M2FF0 = 5C 29 01 9E 65 74 52 28    M31C0 = 58 25 05 84 04 29 11 28
M2FF8 = 12 7A 6C 4D 14 52 5A 7F    M31C8 = 29 11 BC 48 21 80 84 AA
M3000 = FC 51 28 31 13 41 25 09    M31D0 = 20 7F F8 58 28 30 FE 10
M3008 = 94 22 62 68 70 C2 94 0E    M31D8 = 80 50 28 37 E0 7F F8 25
M3010 = 20 F8 FC 5C 20 83 50 28    M31E0 = 04 94 04 29 11 98 81 04
M3018 = 37 E0 1B 90 FF 20 F8 FC    M31E8 = 29 10 33 29 06 6F 79 27
M3020 = E2 5C 20 8B 50 28 37 E0    M31F0 = 21 64 69 4C 22 04 31 FE
M3028 = 1B 90 FF 70 C1 84 13 25    M31F8 = 5C 1B 90 FF 70 27 21 28
M3030 = 03 81 17 26 25 21 08 94    M3200 = 36 03 28 31 0F 67 6C 70
M3038 = 17 75 50 28 00 87 18 90    M3208 = 5C 70 B6 67 5C 20 46 50
M3040 = FF 26 25 21 08 94 F3 90    M3210 = 28 37 E0 20 84 50 28 37
M3048 = 07 26 25 21 0C 94 EB 48    M3218 = E0 7F F8 22 10 58 64 69
M3050 = 50 41 58 13 2A 30 7C 8E    M3220 = 4C 21 F7 5C 7F F8 25 03
M3058 = 16 06 16 07 28 00 66 28    M3228 = 84 0E 26 25 91 0A 20 46
M3060 = 31 30 67 6C 70 5D B6 64    M3230 = 50 28 37 E0 29 31 EE 26
```

```
M3238 = 25 21 01 94 04 29 06 AB    M3408 = 28 36 73 29 34 11 29 01
M3240 = 29 34 72 63 6B 20 F0 FC    M3410 = 58 63 6B 20 F0 FC 5C 28
M3248 = 5C 2A 20 48 74 17 17 17    M3418 = 35 76 65 28 36 6A 28 30
M3250 = 17 20 14 17 17 17 17 28    M3420 = 8E 63 6B 7F FC 54 28 30
M3258 = 35 76 64 28 36 6A 63 6B    M3428 = D6 2A 34 36 28 36 E2 20
M3260 = 7F FD 13 50 13 C0 24 C2    M3430 = 70 F7 57 1B 90 FF 63 6B
M3268 = 56 71 55 28 15 54 6F 20    M3438 = 7F FC 50 4C 14 E0 4C 94
M3270 = 13 5C 28 16 93 64 72 52    M3440 = 2E 65 6C 2A 20 84 16 50
M3278 = 28 12 7A 92 14 76 50 28    M3448 = 15 5D 40 14 5D 70 5D 75
M3280 = 00 87 20 3C 50 63 6B 7F    M3450 = 5D 28 30 8E 20 5E 67 6C
M3288 = FC 54 28 30 D6 29 32 09    M3458 = 5C 2A 34 66 28 36 E2 20
M3290 = 6E 4C 25 99 92 E8 2A 20    M3460 = 70 F7 57 1B 90 FF 63 6B
M3298 = 44 64 28 36 3A 63 28 36    M3468 = 20 F0 FC 5C 90 AA 1F 5C
M32A0 = 6A 28 36 34 28 16 93 64    M3470 = 90 A6 28 35 81 63 6B 20
M32A8 = 6F 20 10 FC 84 0B 2A 20    M3478 = F0 FC 5C 64 6F 70 5E 5E
M32B0 = 44 64 28 36 6A 28 36 3A    M3480 = 48 21 10 20 80 84 03 20
M32B8 = 64 2A 20 44 28 36 6A 74    M3488 = 20 63 6A 5C 71 27 22 62
M32C0 = 8E 63 28 36 6A 28 36 34    M3490 = 6D 70 5D 5D 5D 63 6F 5E
M32C8 = 28 16 93 64 6F 20 10 FC    M3498 = 5E 7F 5E 5C 1B 90 FF 70
M32D0 = 94 0D 2A 20 44 64 28 36    M34A0 = 27 22 63 6C 4C 13 1F 1E
M32D8 = 6A 74 8E 28 36 3A 63 6B    M34A8 = 6E CE 51 92 02 1E 4C 13
M32E0 = 7F FC 50 4C 14 E0 84 07    M34B0 = 1D 19 6F CC 50 64 6F 4E
M32E8 = 4C 1F 5C 29 32 57 64 2A    M34B8 = 18 C0 82 09 1F 92 0B 4C
M32F0 = 20 48 28 36 6A 28 36 34    M34C0 = 18 C1 92 06 6F 40 5E 41
M32F8 = 63 28 36 6A 28 16 93 64    M34C8 = 5C 48 21 10 73 84 02 71
M3300 = 72 52 28 12 7A 92 04 29    M34D0 = 50 62 6D 4C 12 5D 4E 15
M3308 = 32 7D 6E 4C 25 09 92 F8    M34D8 = 13 13 13 EC 5D 4C 12 5D
M3310 = 2A 20 28 2C 2A 20 00 20    M34E0 = 4E 15 13 13 13 EC 5D 4C
M3318 = 28 50 16 2C 17 2C 30 94    M34E8 = 12 5C 30 94 E6 28 35 76
M3320 = FA 48 21 20 94 1B 48 22    M34F0 = 62 6D 4D 17 4C 17 63 6B
M3328 = 20 58 20 4E 50 28 37 E0    M34F8 = 7F FC 50 4C 14 E0 84 0A
M3330 = 64 69 4C 22 10 5C 2A 20    M3500 = 4C 1F 5C 28 35 AF 29 34
M3338 = A0 20 C8 17 20 10 27 25    M3508 = 80 28 35 A0 26 21 81 09
M3340 = 7F F8 25 03 94 09 28 0C    M3510 = 79 50 28 00 87 29 34 72
M3348 = B5 94 0A 28 09 26 28 31    M3518 = 28 2E C6 48 21 10 84 11
M3350 = 0F 29 32 24 64 69 4C 22    M3520 = 2A 20 84 16 25 05 82 09
M3358 = 01 21 FB 5C 29 34 11 64    M3528 = 77 50 28 00 87 29 32 05
M3360 = 69 4C 22 0D 5C 2A 20 A1    M3530 = 63 6B 20 F0 FC 5C 28 35
M3368 = 70 17 20 28 17 48 21 DF    M3538 = 76 16 51 16 50 28 17 41
M3370 = 58 20 40 27 21 18 90 FF    M3540 = 28 35 76 63 28 36 3A 63
M3378 = 64 69 4C 21 F7 22 04 5C    M3548 = 6B 7F FC 50 4C 14 E0 84
M3380 = 20 40 27 21 70 B6 28 36    M3550 = 06 4C 1F 5C 90 E1 7F F8
M3388 = 03 74 F7 94 04 28 31 13    M3558 = 25 08 94 04 29 01 20 48
M3390 = 48 21 CF 58 20 46 50 28    M3560 = 21 10 84 04 29 32 43 29
M3398 = 37 E0 64 69 4C 21 FE 5C    M3568 = 33 A3 6D 41 CC 5D 40 19
M33A0 = 29 34 72 70 27 21 7F F8    M3570 = CC 5D 4C 19 5C 1C 63 6B
M33A8 = 25 03 94 0C 28 0C B5 94    M3578 = 7F FC 13 13 2A 20 00 8E
M33B0 = 04 28 09 26 29 34 11 63    M3580 = 1C 08 2A 20 A3 28 36 1D
M33B8 = 6B 20 F0 FC 5C 28 35 76    M3588 = 20 FA 50 26 21 81 0F 28
M33C0 = 64 28 36 6A 20 24 8E 63    M3590 = 35 C2 30 94 F7 79 50 28
M33C8 = 28 36 6A 28 36 34 28 16    M3598 = 00 87 1B 90 FF 29 35 E3
M33D0 = 93 64 73 52 28 12 7A 28    M35A0 = 63 6B 4C 14 13 24 0B 13
M33D8 = 36 43 28 35 76 64 28 36    M35A8 = 13 50 13 13 C0 90 03 20
M33E0 = 3A 63 6B 7F FC 50 4C 14    M35B0 = 14 50 08 2A 20 A3 28 36
M33E8 = E0 84 06 4C 1F 5C 90 CE    M35B8 = 1D 28 35 C2 30 94 FB 29
M33F0 = 7F F8 25 01 94 19 28 0C    M35C0 = 35 E3 26 21 21 40 22 20
M33F8 = B5 94 06 28 09 26 90 0C    M35C8 = 27 21 21 40 27 21 09 2A
M3400 = 62 68 77 FC 25 07 94 04    M35D0 = 20 99 28 36 1B 64 69 4C
```

```
M35D8 = 22 80 5C 2A 20 98 76 17
M35E0 = 18 90 FF 2A 35 FC 0E 2A
M35E8 = 20 9A 28 36 2F 64 69 4C
M35F0 = 22 80 5C 2A 20 98 20 FC
M35F8 = 17 1B 90 FF 2A 20 A3 28
M3600 = 36 26 0C 08 2A 20 9D 28
M3608 = 36 1D 64 69 4C 22 40 5C
M3610 = 2A 20 9C 20 C0 17 1B 90
M3618 = FF 41 17 40 17 00 17 01
M3620 = 17 1C 16 51 16 50 16 04
M3628 = 16 05 1C 41 17 40 17 02
M3630 = 17 03 17 1C 6F 20 10 EC
M3638 = 5C 1C 6C 74 50 4D 17 30
M3640 = 94 FC 1C 08 6F 4C 50 70
M3648 = 5C 6C 18 75 19 24 66 DC
M3650 = 5D 70 8F F9 92 07 19 5C
M3658 = 28 16 86 71 C0 5C 6C 4C
M3660 = 21 F0 5C 0C 6C 70 5D 73
M3668 = 90 03 6C 74 50 16 5D 30
M3670 = 94 FC 1C 08 63 6B 20 F0
M3678 = FC 5C 28 35 76 64 28 36
M3680 = 6A 6E 76 50 71 F0 94 05
M3688 = 4C 14 90 03 7F FE 81 20
M3690 = 12 51 52 53 A0 21 10 84
M3698 = 0C 31 94 F9 32 94 F6 33
M36A0 = 94 F3 90 17 20 20 80 20
M36A8 = 12 51 52 53 A0 21 10 94
M36B0 = 0D 31 94 F9 32 94 F6 33
M36B8 = 94 F3 70 80 0C 70 80 30
M36C0 = 94 C3 63 6B 7F FC 50 4C
M36C8 = 14 E0 84 06 4C 1F 5C 90
M36D0 = AA 0C 2A 20 82 00 17 01
M36D8 = 17 1C 2A 20 82 16 04 16
M36E0 = 05 0C 0E 2A 20 80 02 17
M36E8 = 03 17 71 86 1C 71 F1 84
M36F0 = 05 20 3F F0 50 20 80 F0
M36F8 = 84 1C 2A 20 98 20 FF 88
M3700 = 84 07 2A 20 98 17 90 0E
M3708 = 64 69 4C 21 7F 5C 2A 20
M3710 = 99 28 36 24 0C 20 40 F0
M3718 = 84 1C 2A 20 9C 20 FF 88
M3720 = 84 07 2A 20 9C 17 90 0E
M3728 = 64 69 4C 21 BF 5C 2A 20
M3730 = 9D 28 36 26 0C 20 20 F0
M3738 = 84 19 2A 20 9F 20 FF 88
M3740 = 84 07 2A 20 9F 17 90 0B
M3748 = 64 69 20 DF FC 5C 47 22
M3750 = 20 57 20 10 F0 84 18 2A
M3758 = 20 A0 20 FF 88 84 07 2A
M3760 = 20 A0 17 90 0A 64 69 20
M3768 = EF FC 5C 70 27 25 73 F0
M3770 = 84 27 2A 20 A1 20 FF 88
M3778 = 2A 20 A1 17 82 18 20 FF
M3780 = 88 2A 20 A2 17 82 12 74
M3788 = 50 28 00 87 64 69 4C 21
M3790 = F7 5C 70 27 21 29 31 EE
M3798 = 74 F0 84 25 26 25 21 01
M37A0 = 84 1F 7F F8 25 03 84 05
M37A8 = 26 25 81 15 64 69 4C 21
M37B0 = FB 5D 48 21 20 84 07 7F
M37B8 = FC 5C 28 31 30 29 31 FC
M37C0 = 71 F0 84 1A 26 25 21 02
M37C8 = 84 14 7F F8 25 03 84 05
M37D0 = 26 25 81 0A 54 69 4C 21
M37D8 = FE 5C 29 33 73 29 3E EB
M37E0 = A1 53 70 81 A0 21 2F 52
M37E8 = 21 20 E0 50 21 2F 80 40
M37F0 = 80 A4 A4 A4 40 21 2F 30
M37F8 = A4 A4 A4 42 80 43 51 1C
```

While the present invention has been described in detail with reference to specific embodiments thereof, it will be understood that various changes and modifications may be made therein by those skilled in the art, without departing from the spirit and scope of the invention as defined in the appended claims.

The invention is claimed as follows:

1. A commodity analysis instrument for measuring the quantity of a constituent present in a sample of a commodity comprising a sample receptacle for receiving said sample, a radiant energy source, means for rotating the sample receptacle so as to bring a substantially contiguous segments of the sample surface repeatedly into registry with the radiant energy source for providing reflected radiant energy therefrom, filter means including a plurality of filter elements and mounted between said sample receptacle and said radiant energy source, each of said filter elements passing a predetermined frequency of radiant energy, stepping means for sequentially moving each of said filter elements to a stationary position in registry with the rotating sample receptacle for a predetermined increment of time for providing said reflected radiant energy at each of said predetermined frequencies, chopper means mounted between said source of radiant energy and said filter means for passing said radiant energy through each filter element at a plurality of discrete intervals, sensor means adjacent said sample receptacle for receiving said reflected radiant energy at each said discrete interval and for providing electrical signals corresponding thereto and circuit means for receiving said electrical signals and providing an indication therefrom corresponding to the quantity of said constituent present in said sample.

2. A commodity analysis instrument according to claim 1 wherein said chopper means passes said radiant energy signals from said radiant energy source at a plurality of discrete intervals to each of said filter elements when it is in registry with said sample receptacle.

3. A commodity analysis instrument according to claim 1 further including means for providing relative movement between the axis of rotation of said sample receptacle and said sensor means for said reflected radiant energy to be received by said sensor means from one of a plurality of substantially annular portions of the surface of the sample.

4. A commodity analysis instrument according to claim 1 wherein said means for rotating said sample receptacle sand said sensor means includes motor means coupled for rotation of said sample receptacle.

5. A commodity analysis instrument according to claim 1 wherein said sample receptacle is mounted for rotation substantially about a central axis and wherein said sensor means is mounted in a stationary position above and to one side of said sample receptacle for sensing said reflected radiant energy from a generally circular section of the surface of said sample.

6. A commodity analysis instrument according to claim 4 wherein said sensor means is mounted in a stationary position for sensing said reflected radiant energy from a generally annular section of the surface of said sample.

7. A commodity analysis instrument according to claim 4 wherein said sample receptacle is mounted for rotation about an axis other than a central axis and said sensor means is mounted for receiving said reflected radiant energy from a generally annular section of the surface of said sample.

8. A commodity analysis instrument according to claim 1 wherein said chopper means comprises a generally opaque disc having a plurality of slots therethrough and further including motor means for rotating said disc.

9. A commodity analysis instrument according to claim 8 wherein said plurality of slots comprises four slots of substantially equal dimensions disposed symmetrically about a common radius of said disc.

10. A commodity analysis instrument according to claim 9 wherein said filter means comprises a filter disc, and said filter elements comprise a plurality of filters mounted in said filter disc and disposed symmetrically about a common radius thereof, substantially equal to the common radius of disposition of said slots in said chopper disc.

11. A commodity analysis instrument according to claim 10 wherein said stepping means includes motor means connected to rotate said filter disc.

12. A commodity analysis instrument according to claim 11 wherein said motor is adapted to rotate said filter disc in discrete steps for placing each of said filter elements into registry with said sample receptacle for said predetermined increment of time comprising substantially one second, and said second motor is adapted to rotate said chopper disc at substantially 1800 RPM for providing said plurality of discrete intervals of radiant energy through said slots to each of said filter elements and therethrough to said sample receptacle.

13. A commodity analysis instrument according to claim 12 further including drawer means for holding said sample receptacle and said first motor means and for selectively moving said sample receptacle into and out of registry with said radiant energy source.

14. A commodity analysis instrument according to claim 2 further including a housing for containing said filter means and said chopper means and a first temperature regulating means mounted in said housing for regulating the temperature thereof to maintain a substantially constant, predetermined temperature therein.

15. A commodity analysis instrument according to claim 14 further including a second temperature regulating means for regulating the temperature of said sensor means to a substantially constant, predetermined temperature.

16. A commodity analysis instrument according to claim 1 wherein said circuit means comprises a measurement and control circuit for receiving said electrical signals, for calculating the optical density of the sample therefrom, for applying a plurality of empirically determined constants to said calculated optical density to determine said quantity of constituent present in said sample and for producing said indication corresponding to said quantity of constituents present in said sample in accordance with said determination.

17. A commodity analysis instrument according to claim 16 wherein said measurement and control circuit further includes means for controlling, in accordance with predetermined instructions stored therein, said predetermined increment of time and said plurality of discrete intervals and, in a predetermined sequence, said receiving of said electrical signals, said calculating of said optical density, said applying of said constants and said indication producing.

18. A commodity analysis instrument according to claim 1 wherein said circuit means includes means for averaging the electrical signals received at each frequency so as to provide an output indicative of the average quantity of constituent present over the surface of the sample observed by the sensor.

19. An analysis instrument for measuring the quantity of a constituent present in a sample of grain comprising: a source of radiant energy for directing radiant energy upon the surface of said sample for providing reflected radiant energy therefrom, means interposed between said sample and said source of radiant energy for passing said radiant energy at each of a plurality of discrete frequencies for a predetermined increment of time and at a plurality of discrete intervals within each of said predetermined increments of time, sensor means for receiving said reflected radiant energy and producing electrical signals corresponding thereto, and measurement and control circuits for receiving said electrical signals, for calculating the optical density of the sample therefrom, and for applying a plurality of empirically determined constants to said calculated optical density to determine said quantity of a constituent present in said sample, and wherein said measurement and control circuits include memory means for storing said empirically determined constants, said memory means being of an alterable, non-volatile type, and said instrument further includes means including a control panel accessible to an operator for selectively supplementing and altering said empirical constants stored in said memory means.

20. An analysis instrument according to claim 19, wherein said measurement and control circuits include memory circuits coupled to said sensor means for receiving and storing said electrical signals.

21. An analysis instrument according to claim 19 wherein said measurement and control circuits include means for producing output signals corresponding to said quantity of said constituent determined to be present in said sample, and for controlling, in a predetermined fashion said predetermined increment of time and said plurality of discrete intervals and, in a predetermined sequence, said receiving of said electrical signals, said calculating of said optical density, said applying of said constants, and said output signal producing.

22. An analysis instrument according to claim 21, wherein said measurement and control circuits include a microprocessor for performing said calculating of said optical density and said application of said constants thereto and for performing said controlling in accordance with predetermined instructions for producing output signals corresponding to said quantity of constituent present in said sample.

23. An analysis instrument according to claim 19 further including a display panel and wherein said measurement and control circuits further include display circuits connected to said display panel for providing an observable indication of said quantity of said constituent present in said sample.

24. An analysis instrument in accordance with claim 20, further including position and timing circuits connected to said means for providing said radiant energy for said predetermined increment of time and at said plurality of discrete intervals and connected to said measurement and control circuits for providing position and timing signals thereto corresponding to said predetermined increment of time and to said plurality of discrete intervals.

25. An analysis instrument according to claim 24, wherein said measurement and control circuits include pre-amp and level circuits connected between said sensor means and said memory circuits for receiving said electrical signals from said sensor means and adjusting the level of said electrical signals with reference to ground and in accordance with a dark reference level.

26. An analysis instrument according to claim 25, wherein said measurement and control circuits include an input/output circuit connected to said pre-amp and level circuits for receiving said electrical signals, connected to said position and timing circuits for receiving said position and timing signals and providing said dark reference level in response to said electrical signals and said position and timing signals, and connected between said pre-amp and level circuits and said memory circuits for providing a predetermined portion of each of said electrical signals thereto in accordance with said timing signals to be stored in said memory circuits.

27. An analysis instrument according to claim 19 wherein said memory means for storing said empirically determined constants comprises at least one EAROM.

28. An analysis instrument according to claim 22, further including memory circuits for receiving and storing said electrical signals from said sensor means, and wherein said microprocessor includes a central processing unit for performing said calculating of optical density, said application of constants thereto, said controlling in accordance with said instructions and said producing of output signals, at least one peripheral storage unit connected to said central processing unit for storing said predetermined instructions and a static memory interface connected between said central processing unit and said memory circuits for storing said electrical signals for transmitting said electrical signals to said central processing unit as called for thereby.

29. An analysis instrument according to claim 28 wherein another peripheral storage unit is further connected to said memory means for said constants for selecting and transmitting said contants to said central processing unit as called for thereby.

30. An analysis instrument according to claim 29 wherein at least one further peripheral storage unit is also connected in said input/output circuit and to said memory circuits for storing said electrical signals for transmitting said electrical signals to said memory circuits to be stored therein.

31. An analysis instrument according to claim 30 further including erasable and programmable read only memory means connected to said static memory interface for selectively storing predetermined instructions to supplement said predetermined instructions stored in said peripheral storage units and to alter said predetermined instructions stored in said peripheral storage units.

32. An analysis instrument according to claim 22 wherein said mircoprocessor includes a central processing unit for performing said calculating of said optical density, said application of constants thereto, said controlling in accordance wih said predetermined instructions and said producing of output signals, erasable and programmable read only memory means for storing said set of predetermined instructions, a static memory interface connected between said central processing unit and said read only memory means for transmitting said predetermined instructions therefrom to said central processing unit as called for thereby, and at least one peripheral input/output units connected between said central processing unit and said memory means for said empirically determined constants for selecting and transmitting said empirically determined constants to said central processing unit as called for thereby.

33. An analysis instrument according to claim 22 further including memory circuits for receiving and storing said electrical signals from said sensor means, at least one other peripheral input/output unit connected in said input/output circuit and to said memory circuits for storing said electrical signals, for transmitting said electrical signals to said memory circuits to be stored therein.

34. An analysis instrument for measuring the quantity of a constituent present in a sample of a material comprising: means for producing a plurality of electrical signals corresponding to a function of the optical density of said sample, a microprocessor connected to said electrical signal producing means, said microprocessor operating in accordance wih a set of predetermined instructions for receiving said plurality of electrical signals, for calculating the optical density of the sample in accordance with said electrical signals, for applying a plurality of empirically determined constants to said calculated optical density to determine said quantity of constituent present in said sample, for producing output signals corresponding to said quantity of constituent present in said sample in accordance with said determination thereof, and for controlling, in a predetermined sequence, said receiving of electrical signals, said calculating of optical density, said applying of said constants and said producing of said output signals, alterable nonvolatile memory means for storing said empirically determined constants and means including a control panel accessible to an operator and including said microprocessor, for selectively supplementing and altering said empirical constants stored in said memory means.

* * * * *